United States Patent [19]
Margrey et al.

[11] Patent Number: 5,631,844
[45] Date of Patent: May 20, 1997

[54] INTERACTIVE REMOTE SAMPLE ANALYSIS SYSTEM

[75] Inventors: Keith S. Margrey; Robin A. Felder; James C. Boyd, all of Charlottesville; J. William Holman, Earlysville; John Savory, Keswick, all of Va.

[73] Assignee: University of Virginia, Charlottesville, Va.

[21] Appl. No.: 343,773

[22] Filed: Nov. 22, 1994

Related U.S. Application Data

[62] Division of Ser. No. 739,204, Jul. 30, 1991, Pat. No. 5,366,896.

[51] Int. Cl.$^6$ .......................... G01N 33/00; G01N 35/00
[52] U.S. Cl. ................................. 364/496; 436/43
[58] Field of Search ................... 364/496, 413.08, 364/413.04, 413.1, 413.11, 413.07, 224.5; 422/62, 64, 50; 369/24, 29; 395/200.09; 436/43, 48, 47, 50

[56] References Cited

U.S. PATENT DOCUMENTS 4,781,891 11/1988 Galle et al. ................... 422/64
4,996,703 2/1991 Gray .......................... 379/40

*Primary Examiner*—Emanuel T. Voeltz
*Assistant Examiner*—Tony M. Cole
*Attorney, Agent, or Firm*—Sheldon H. Parker

[57] ABSTRACT

An interactive multi-station medical specimen analysis system for simultaneously analyzing a medical specimen at remote locations and accessing, for evaluation, the results of each of the analyses at a central laboratory is disclosed. The system comprises a server for storing databases. A central laboratory, interacts with the dedicated computers through the server to review, evaluate and either accept or reject specimen analyses. Communication means connect the server with the plurality of dedicated computers, laboratory computer and a centralized mainframe. Analytical instrument to dedicated computer interface software interprets the instrument language into the computer program language and the computer program language into the instrument language. Dedicated computer interactive means request analytical tests, transmit the test results to the server databases and receive and display data from the server databases. Laboratory computer interactive means acquire and display test results from the server databases, review and accept or reject the test results and transmit the acceptance or rejection to the server databases.

3 Claims, 12 Drawing Sheets

INTERACTIVE REMOTE SAMPLE ANALYSIS SYSTEM

BACKGROUND OF THE INVENTION

Cross Reference to Related Applications

This application is a continuation-in-part to U.S. application Ser. No. 07/739,204, filed Jul. 30, 1991, issued Nov. 22, 1994 as U.S. Pat. No. 5,366,896.

FIELD OF THE INVENTION

The invention relates to an integrated analytical system which includes a remote analyzing instrument and a central monitoring station.

DESCRIPTION OF THE PRIOR ART

Dramatic improvements in industrial productivity and quality have been achieved with the application of computer related technology. Against this backdrop hospitals and hospital laboratories across the country have integrated computers into the hospital care system. Health care traditionally has been a difficult marketplace for automation because of the complexity of the procedures and the potential risks to human life if an error were to occur.

In confronting increasing pressure to reduce the cost of providing analytical results, many laboratories have centralized their services to conserve resources. By consolidating services, expensive equipment has less idle time and labor is used more cost effectively. However, centralization may adversely affect the sample-to-result turnaround time by increasing the distance of the centralized laboratory from the origin of the specimen. Frequently, analytical results must be obtained in a short time to provide information for rapid assessment of a situation so that corrective actions may be taken. In medical care, for example, the clinical state of a critically ill patient must be assessed and corrected before a life threatening condition occurs. Similarly, in the outpatient clinic, providing results of blood analysis to physicians while patients are still in the physicians' office is highly desirable because it obviates the need for a return appointment to discuss abnormal laboratory results. In industrial process control, real-time monitoring of the progress of chemical reactions by on-site analytical techniques prevents dangerous conditions or loss of products.

Up to now, improvements in the turnaround of results have been obtained either by dedicated rapid specimen transportation systems or by simplifications of analytical techniques that make the specimen analysis faster. Pneumatic tube systems, mobile carts, and human messengers have been used with some success to transport specimens rapidly to the central laboratory. However, these systems are expensive to install and maintain; and in some facilities retrofitting of pneumatic tube systems or cart systems is not possible.

Additionally, there has been much interest in simplifying analytical instruments so that non-technical employees can perform complex analysis. For example, physician's office laboratories have been equipped with a new generation of analyzers that can provide rapid results with minimal operator training. Unfortunately, the results provided by many of these simple analyzers are not as precise or accurate as the results obtained in the centralized laboratories. Furthermore, the adequacy of quality control has frequently been overlooked. New pending federal regulations require that only trained medical technologists perform laboratory tests. These regulations will prohibit the physician or paramedical personnel (e.g. nurse or respiratory therapist) from performing clinical laboratory tests.

A user interface indicates a software design that makes many of the complex codes for computerized instrument control and data input/output transparent to the user. Simple English language commands should be used to give instructions to a computer, analytical instrument and/or robot. Although many companies have developed simple-to-use computer, instrument and robotic-control languages accessible to most computer programmers, unfortunately the programming associated with communication with other devices remains incomplete.

Nationally, there has been an increasing trend toward performance of selected laboratory tests using whole blood analyzers located close to the critical care patient's bedside. This approach has the advantage of providing an average test turnaround time of 5 minutes. Up to now, this testing generally has been performed by individuals with minimal training in medical technology. Newly instituted Joint Commission of the American Hospitals Organization and College of American Pathologists ancillary testing regulations require a similar level of quality control as that required by larger laboratories offering similar services. Because most personnel working in intensive care settings have neither the experience nor desire to perform rigorous quality control, this function will be assumed by trained medical technologists from the clinical laboratory in many centers. Staffing these satellite whole blood analysis laboratories with medical technologists will result in much higher costs unless an automated alternative can be developed.

Remote technology could also find a use in laboratories peripheral to the medical center. The estimated 100,000 physicians office laboratories in the United States perform approximately 25% of total laboratory testing. Besides being profitable for physicians, the major incentive for performing laboratory tests in the physicians office is the rapid turnaround. Rapid analysis results in prompt initiation of treatment, reduction in patient stress, and a reduction in repeat office visits. The major criticism of physician office testing is the lack of adequate quality control. Proposed regulations recently issued by the Health Care Finance Administration (HCFA) to carry out the Clinical Laboratory Improvement Act of 1988 (CLIA) require each physicians' office laboratory to monitor and document quality assurance, proficiency testing, safety, and instrument maintenance. Employees must meet the qualifications set forth by the Department of Health and Human Services and be involved in a continuing education program. Robotics can provide many physicians with the laboratory services they require on site yet put the responsibility of monitoring quality, hiring and training qualified personnel, and maintaining instruments in the hands of a local commercial laboratory or hospital. Connection of the remote laboratory in the physicians office to the commercial laboratory could be through a telephone line.

Additional uses can be in the field of microbiology, as many microbiology tests have been reduced to simple devices which can be easily handled by robot. The remote laboratory can be configured to also include microbiology analysis.

The next major medical frontier is the use of molecular biology for identification and diagnosis of genetic-based diseases. Once the aberrant gene is identified, gene therapy eventually may allow replacement of defective genes. Molecular biology is already providing many new tests which are being used to identify various genetic diseases (e.g., cystic fibrosis and sickle cell anemia). There has been a rapid expansion in the number and variety and simplicity of analysis based on genetic markers. The remote laboratory can be used for rapid, on site testing based on molecular biology.

Hematology analysis are usually performed on heparinized whole blood specimens. The heparin (usually in the specimen tube before the blood is drawn into it) serves as an anticoagulant so that the blood remains free flowing. Hematologists are usually concerned with analysis such as white blood cell concentration, the number of subpopulations of white cells, red cell concentration and morphology gradients, and platelet concentrations.

U.S. Pat. No. 4,670,219, Nelson et al. discloses an analysis system having a first region in which sample materials are stored at an appropriate storage temperature and an analysis region which is maintained at a controlled and stabilized temperature higher than the temperature of the first region. The transfer mechanism includes a liquid handling probe that is mounted on a probe transport carriage, and a drive for moving the transport carriage between the first and second regions. The transport carriage includes a storage chamber connected to the liquid handling probe, thermal energy supplying means in heat exchange relation with the storage chamber, and thermal sensor means carried by the transport carriage. Means responsive to the thermal sensor supplies thermal energy to the transport carriage to maintain the storage chamber at substantially the same temperature as the analysis region.

U.S. Pat. No. 4,676,951, Armes et al. discloses an automatic system for analyzing specimens which have been selectively treated. The specimens are arranged in a plurality of specimen trays with each tray containing a plurality of specimens. A work station selectively moves the trays one at a time from the tower to selectively deliver reagent or analyze the specimen in the tray. A control system is adapted to sequentially actuate the work station to properly sequence the system so that the reagents are administered to the respective specimens and the specimens have been analyzed after a desired incubating period.

U.S. Pat. No. 4,781,891, Galle et al. discloses an automatic analyzing apparatus for effecting chemical analysis for various sample liquids such as blood, urine and the like, comprising a sample delivery pump for metering a sample liquid into a reaction cuvette, a reagent delivery pump for delivering to the reaction cuvette a given amount of a given reagent selected from a plurality of reagents contained in a reagent cassette, to form a test liquid, a feed mechanism for successively supplying reaction cuvettes along a circular reaction line, a plurality of photometering sections arranged along the reaction line for effecting a plurality of measurements for each test liquid at different time instances to product a plurality of results.

A major difficulty facing implementors of remote analytical stations in health care is the lack of electronic communications, software, or hardware standards in clinical instruments. Many clinical laboratory analyzers, for example, operate as discreet devices with only a RS-232C port for the output of analytical data. Remote, computerized operation of instruments requires an electronic communication standard that allows many of the instrument electronic functions be accessible to the host computer. For example, an analyzer which has been internally programmed to self-calibrate on a predetermined schedule should not initiate a calibration cycle at the same time as an irreplaceable medical specimen is being injected into the sampling port.

Point of care testing is an important component of caring for the critically ill patient. Rapid assessment of oxygen delivery, acid bases status, electrolytes and glucose are essential. Options for providing these services are rapid delivery of specimens to a central facility using a pneumatic tube system, staffing a satellite laboratory, or having on-site instrumentation. The first two approaches are extremely expensive. The third is a viable option but requires the application of new technologies such as "hand-held" analyzers. The expense of these devices is considerable being in the range of $10 per specimen analysis.

The laboratory disclosed herein is an alternative model to the large centralized laboratory facility. One of the major disadvantages of centralized laboratory facilities is the extended length of time to obtain analytical results. Long turnaround time can result in compromised patient care, particularly in intensive care units. A high cost specimen transportation system has been the traditional method to reduce specimen transit time.

The problems outlined above have been overcome through the instant invention which serves as an alternative to the centralized laboratory by providing analytical services near to where the specimen is obtained without substantially increasing the need for additional labor. The instant invention consists of a method to control commercially available analytical instruments via a computer interface linked to novel computer software. The analytical, electronic and mechanical performance of the laboratory is monitored remotely through electronic, radio or optical link. The automated remote laboratory provides extremely rapid turnaround, eliminates the cost of labor for specimen processing, reduces the risk from contaminated specimens, reduces staff training and results in improved patient care.

SUMMARY OF THE INVENTION

An interactive multi-station medical specimen analysis system for simultantously analyzing a medical specimen at remote locations and accessing for evaluation the results of each of the analyses at a central laboratory is disclosed. The system comprises a server for storing databases, including patient demographics and analysis results and for permitting automatic retrieval and storage of data on an interactive basis by a plurality of computers. A plurality of analytical instruments at remote locations each interacting with a dedicated computer, having a display, to activate and interact with the analytical instrument. The computer serves as an interface between the analytical instrument and the server. A central laboratory, having display means, computer to interacts with the dedicated computers through the server to review, evaluate and accept or reject specimen analyses. Communication means connect the server with the plurality of dedicated computers, laboratory computer and a centralized mainframe. An analytical instrument to dedicated computer interface interpret the instrument language into the computer program language and the computer program language into the instrument language. Dedicated computer interactive means request analytical tests, transmit the test results to the server databases and receive and display data from the server databases. Laboratory computer interactive means for acquire and display test results from the server databases, review and accept or reject the test results and transmit the acceptance or rejection to the server databases.

The server database can temporarily store files which consist of information requested from, or being transmitted to the mainframe.

BRIEF DESCRIPTION OF THE DRAWINGS

The objects and features of the invention will become more apparent from the following drawings when read in conjunction with the specification.

DESCRIPTION OF THE PREFERRED EMBODIMENTS

Figure 1:
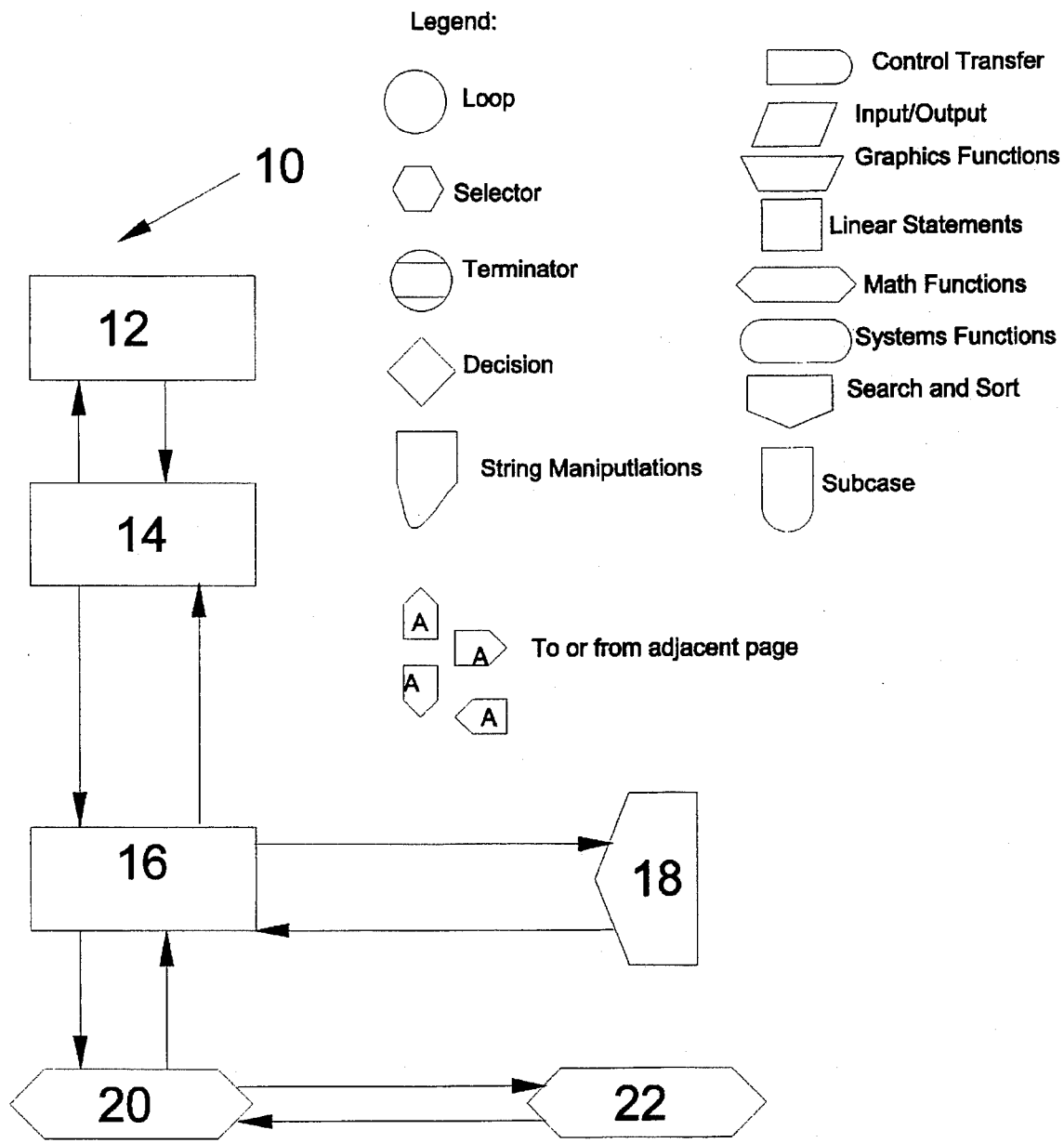
FIG. 1 is a flow diagram of the disclosed, interactive system.
Figure 2:
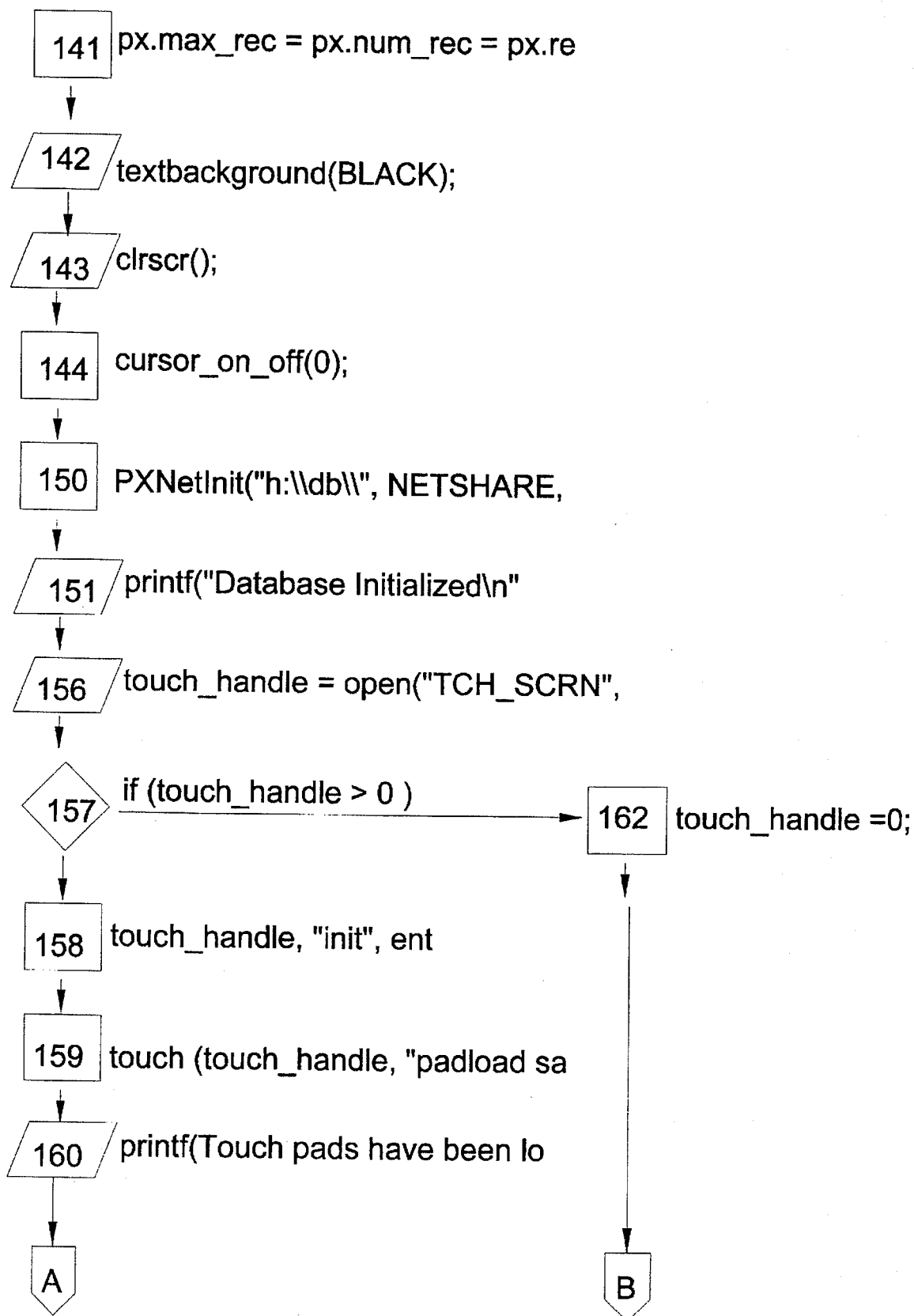
FIGS. 2 through 5 are flow diagrams of the laboratory unit.
Figure 3:
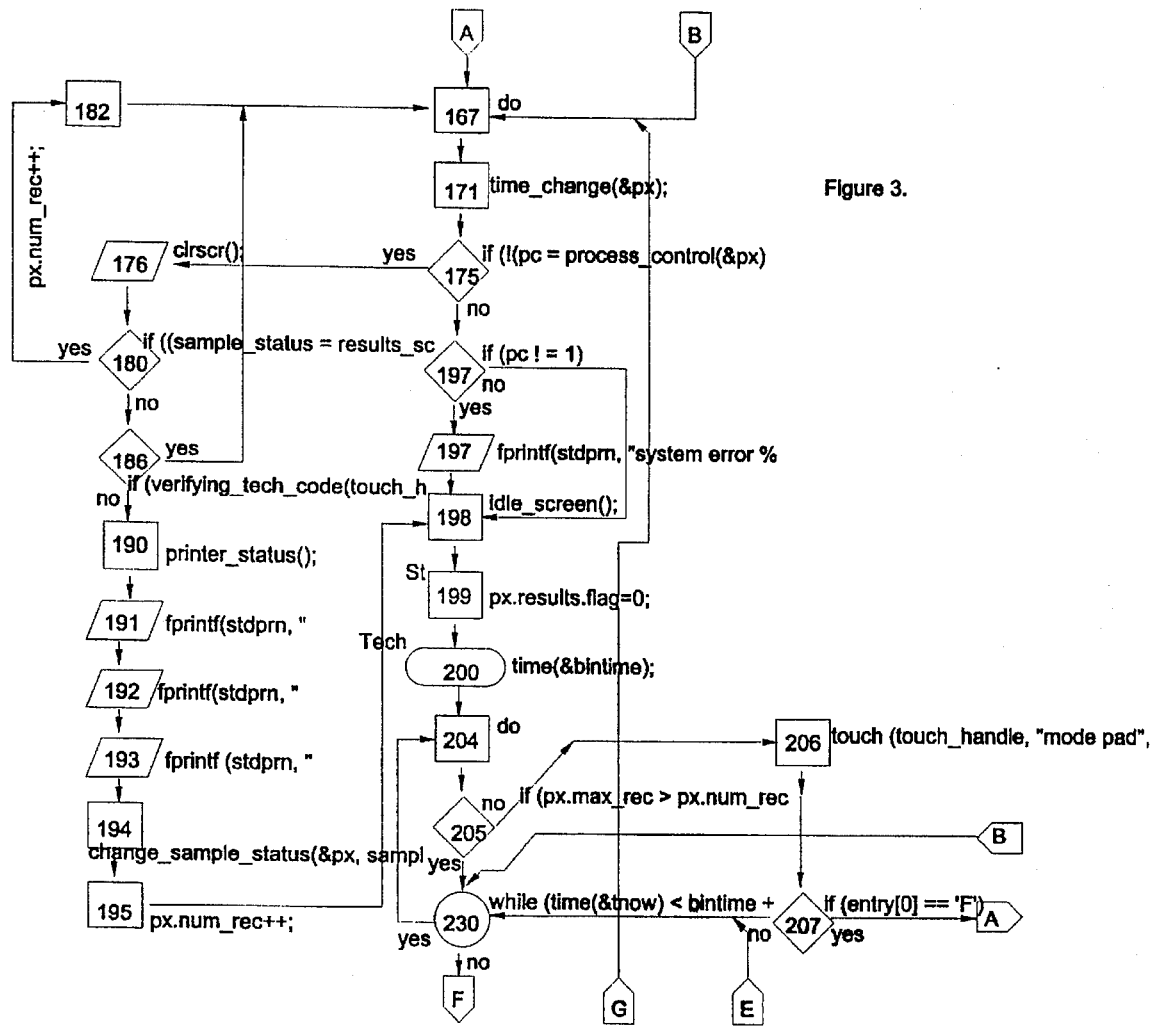
Figure 4:
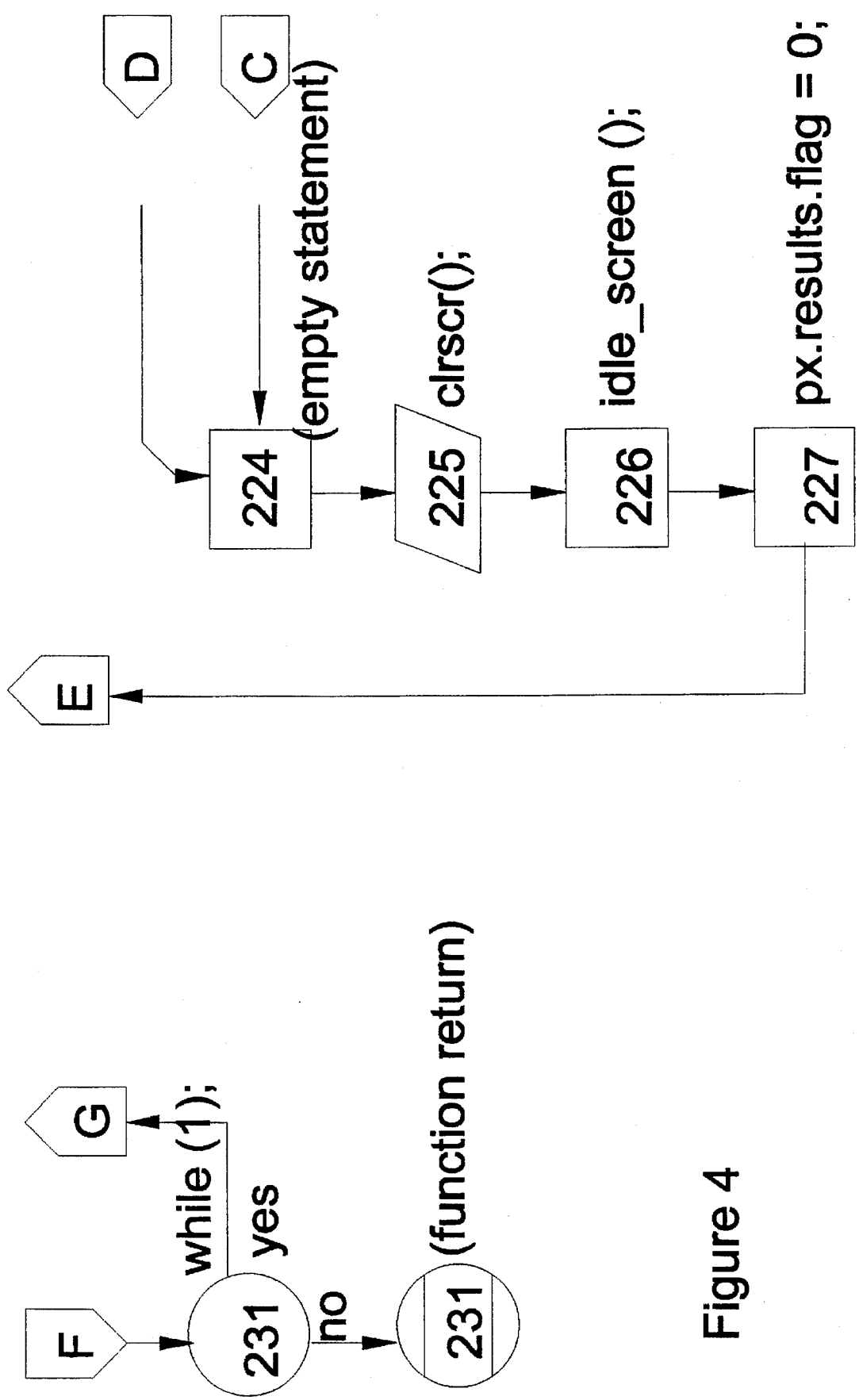
Figure 5:
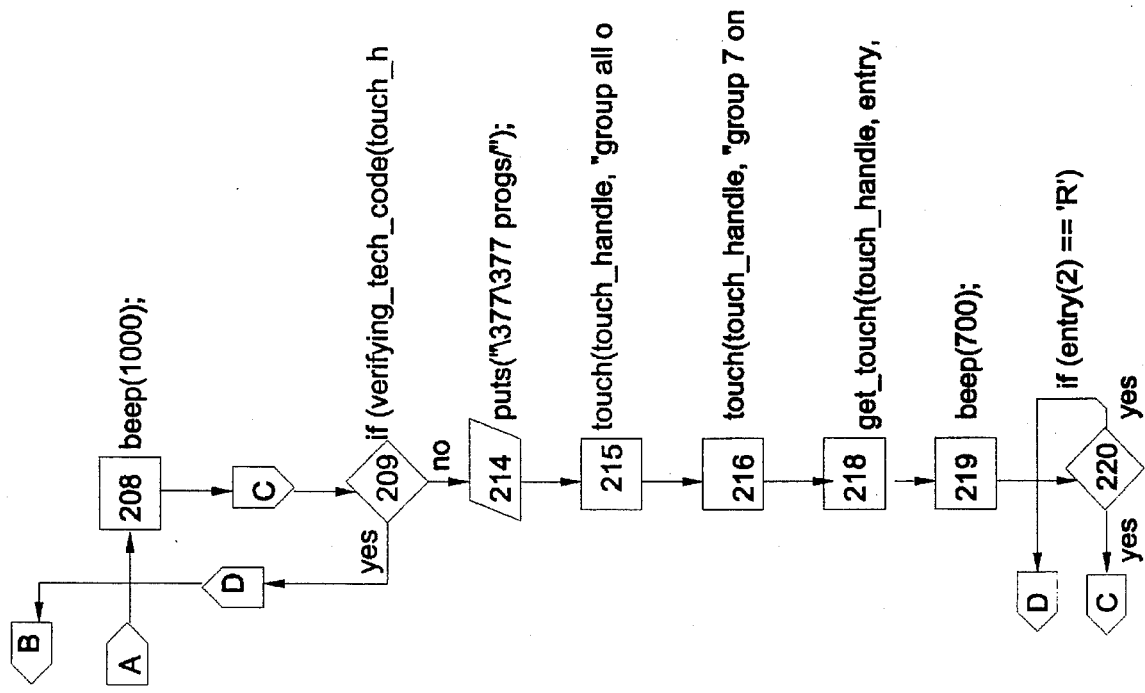
Figure 6:
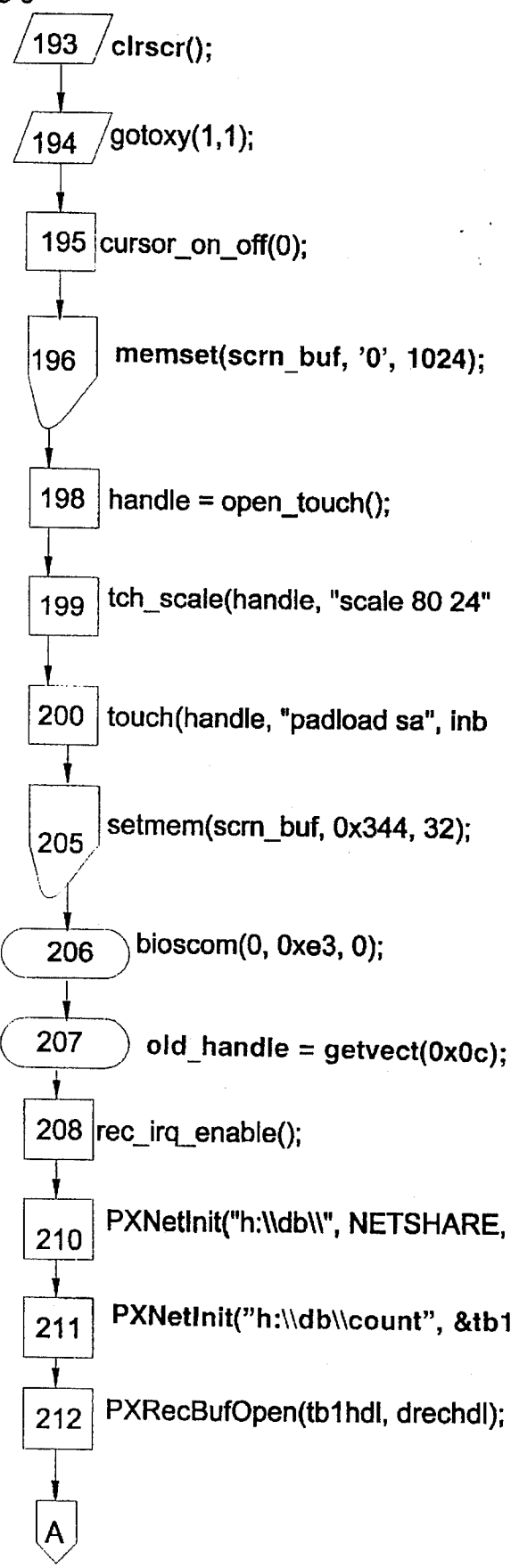
FIGS. 6 through 12 are flow diagrams of the analysis station.
Figure 7:
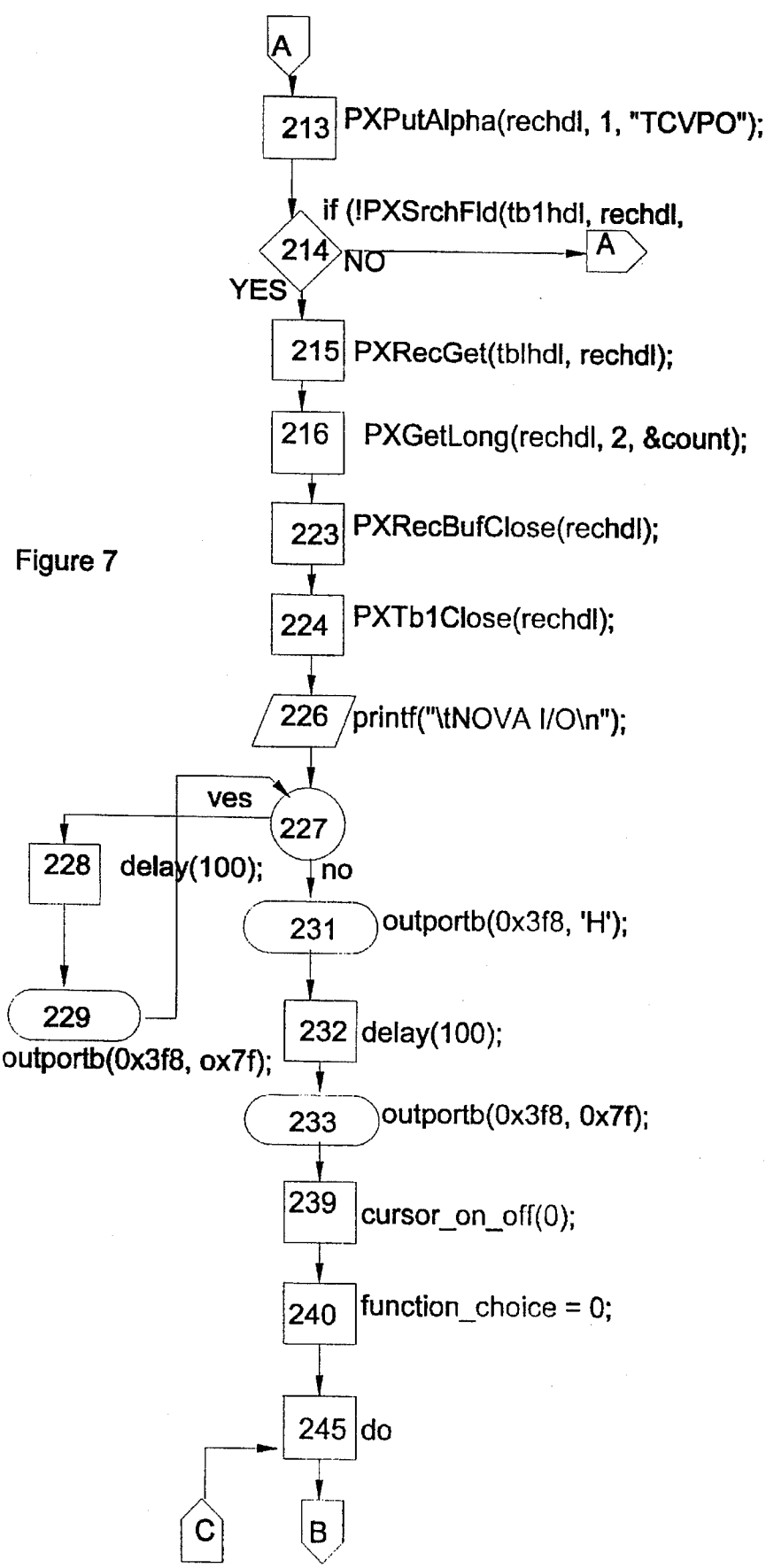
Figure 8:
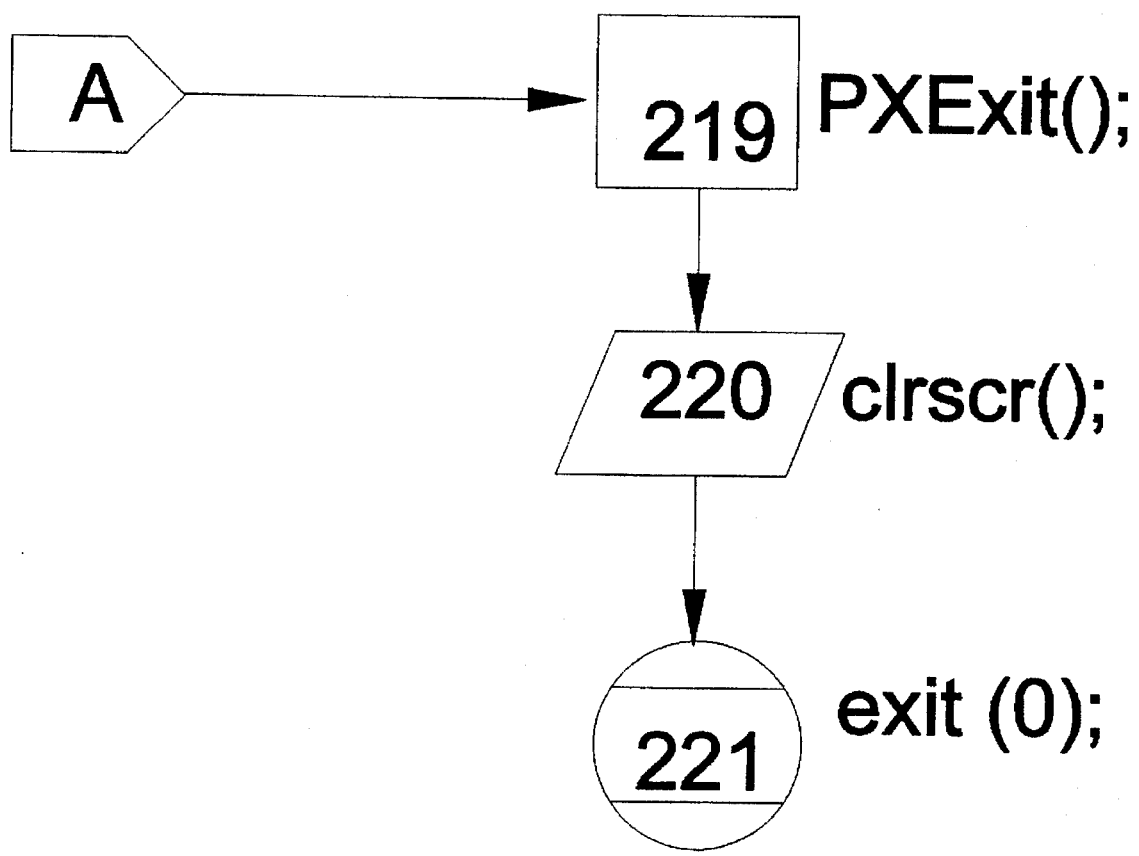
Figure 9:
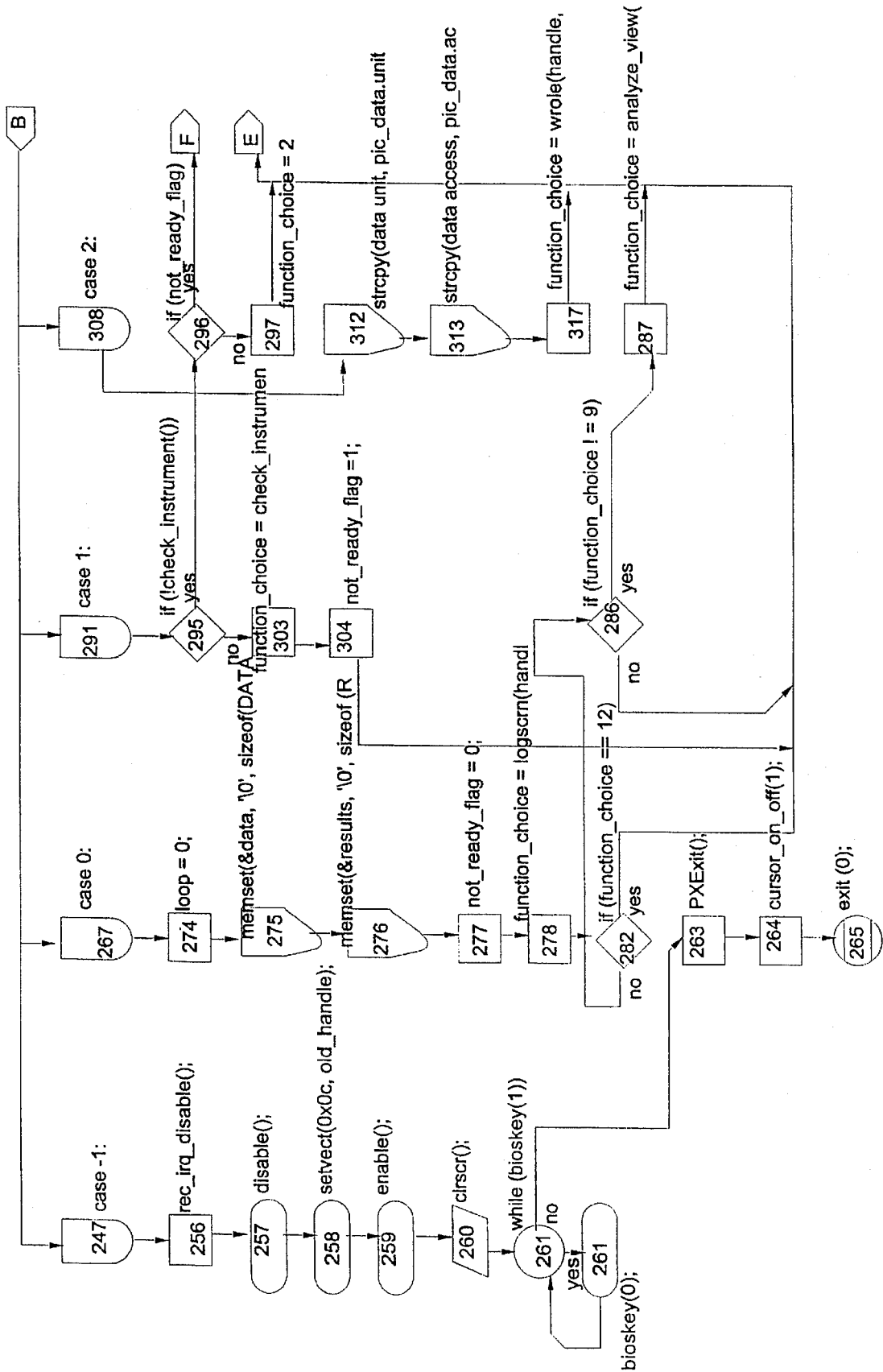
Figure 10:
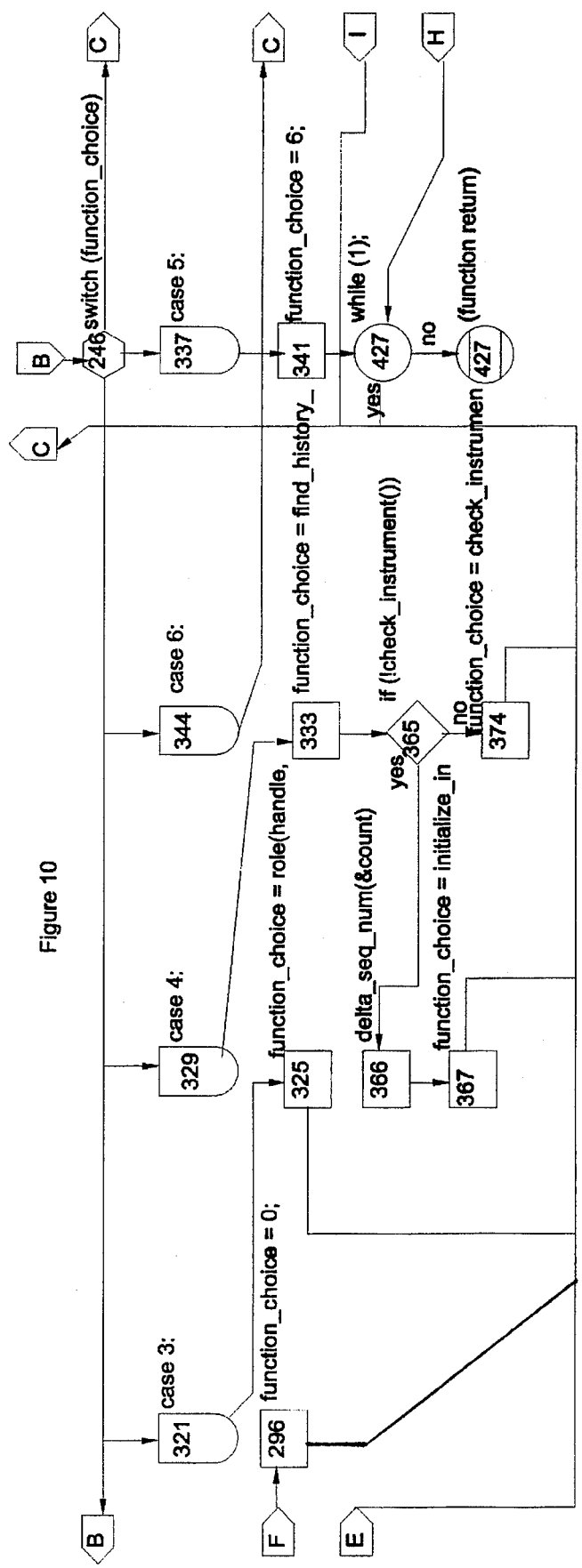
Figure 11:
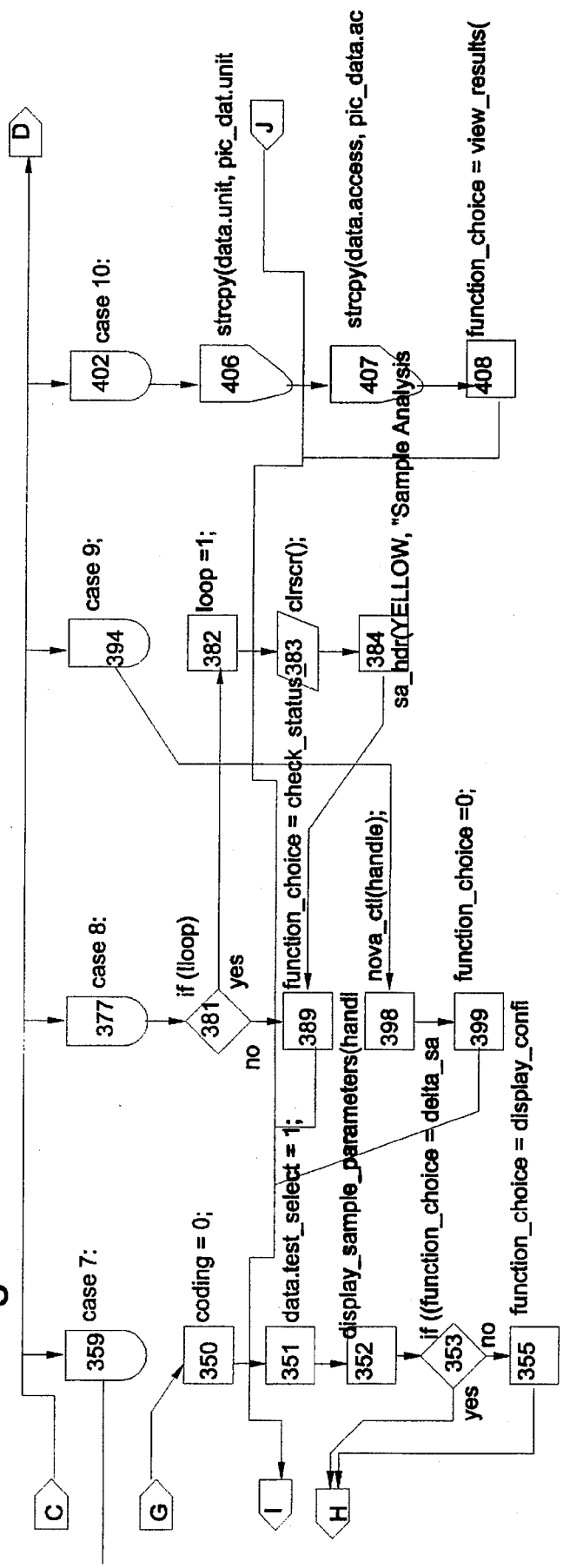
Figure 12:
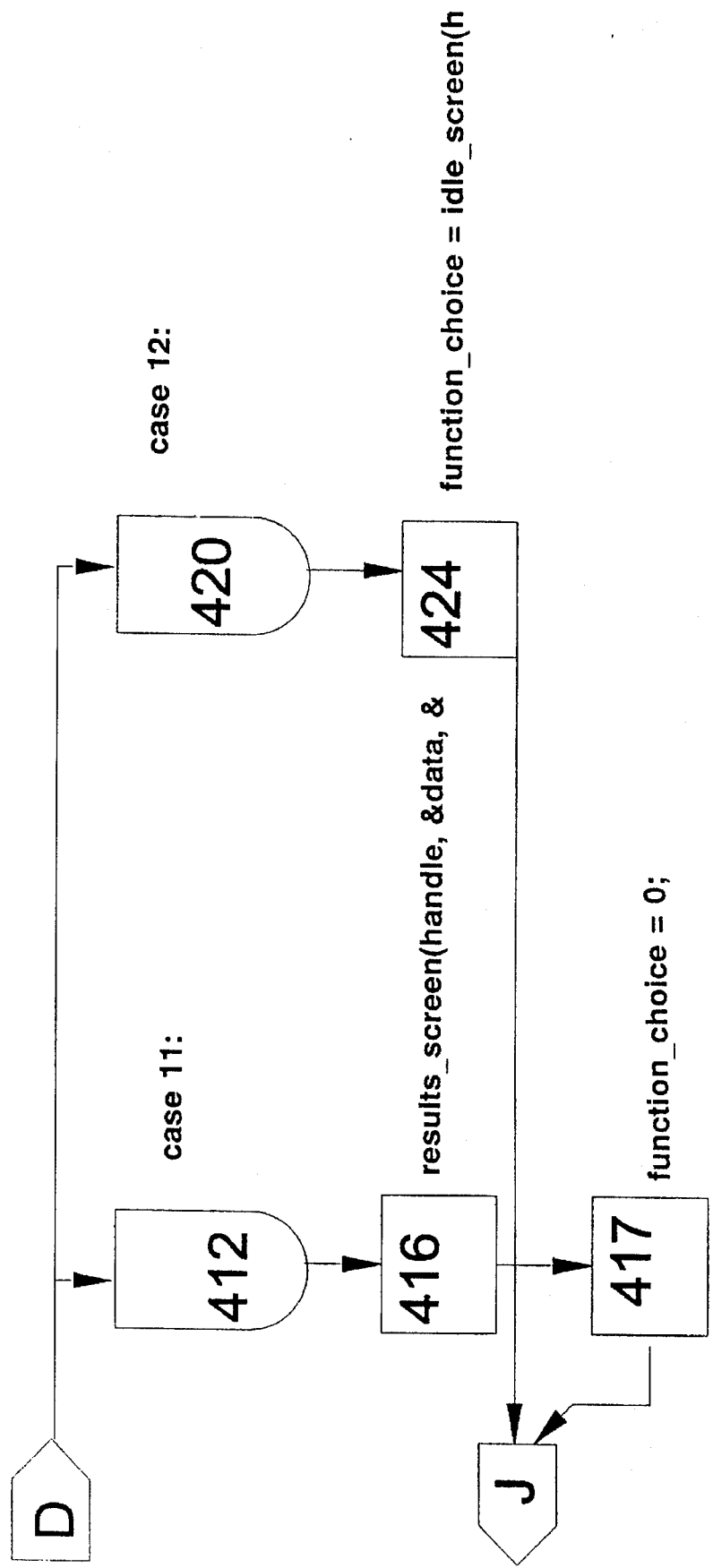

Although many laboratories have centralized critical care services to conserve resources, centralization has often been at the expense of providing optimal patient care. The instant disclosure combines the convenience of satellite Analysis Stations located in, or close to, a critical care unit with the optimal analysis benefits of a centralized laboratory. The Analysis Stations can, for example, provide whole blood analysis of blood gases ($pCO_2$, $pO_2$), pH, electrolytes ($Na^+$, $K^+$, $Cl^-$) glucose, and hemoglobin by utilizing conventional clinical laboratory instruments linked to the centralized Laboratory Unit via computer. A medical technologist in the Laboratory Unit has the ability not only to view the analysis results, but also the ability to control many functions of the Analysis Station. The individuals utilizing the Analysis Station need not be laboratorians as their sole responsibility is to introduce the specimen to the system in much the same way as it would be given to a messenger or placed in a pneumatic tube system for delivery to a central laboratory.

The interactive system has two distinct embodiments, with variations, which will be apparent to one skilled in the art, within each embodiment. In one embodiment, Analysis Stations consist of an analytical instrument and computer. These Stand Alone Analysis Stations are easy to use and relatively economical, the pricing being largely dependent upon the analysis instrument incorporated in the Station. The Stand Alone Analysis Station requires manual introduction of the specimen into the analyzer. In an alternate embodiment an automated system embodiment uses a robot arm to present the blood specimen to the analytical instrument. The original Automated Analysis Station is disclosed in full in U.S. Pat, No. 5,366,896 (formerly copending application Ser. No. 07/739,204) and is incorporated herein as though cited in full. The automated system disclosed herein is an embodiment thereof and therefore only an overview of the sequence of steps is set forth herein. Both the Stand Alone and Automated Analysis Stations are linked to the main Laboratory Unit via a computer network.

Monitors, preferably touch screen, are incorporated into the system both at the Analysis Station and the Laboratory Unit.

In order to clearly set forth the scope of invention, the following component definitions are provided.

Laboratory Unit

The Laboratory Unit consists of a computer, 286 or higher, preferably equipped with a color monitor. The computer can be provided with a small hard drive for storing the screen images and the corresponding program. Alternatively, both the screen images and program can be stored on the server and accessed directly therefrom. The commands are given to the program through any input system, such as touch screen or keyboard. The color monitor is beneficial to provide visual distinction between read-outs, emphasize problems, etc. For example, arterial specimens provide red numbers, and venous specimens blue numbers and flashing numbers indicate that results are out of the reference range. The last 10 analysis obtained on the patient can be displayed in tabular form to facilitate interpretation of out-of-range results or to establish trends. If a pending result is not verified within 10 seconds the satellite central computer sounds a loud alarm which requires user interaction to eliminate. The software program allows the medical technologist to view results and carry out the appropriate action. Patient results are sent from the Laboratory Unit to the network file server where they are stored in a results database.

Server

A dedicated micro-processor is utilized for running all required programs to operate the system. The acquisition of patient demographic information from the main hospital information system and return of completed laboratory test results to the main system is also run through the server. A Laboratory Information System interface serves to translate the patient information received from and sent to the hospital main computer system to the server. Interfacing with the main computer system allows for current patient demographics to be accessed to be used in conjunction with the instant system. The interface utilized can be a standard computer to computer interface meeting the American Society for Testing and Materials (ASTM) specifications, such as set forth in Designations: E 1381-91 and E 1394-91 which are incorporated herein by reference. Once approved, the results received from the analysis are sent to and stored in the hospital's main computer system, thereby further updating the patient's demographics.

Local Area Network (LAN)

Physical computer to computer communication is achieved through any standard commercially available hardware and software. An example of hard-wired networking is the ANSI/IEEE 802.3 (CSMA/CD) standard, utilized as the LAN communication protocol with Novell version 3.1 networking software and EtherNet LAN interface cards. Optical fibers, twisted pair, or coax cable are used to couple the network computers together. Computer to computer communication can also be achieved through satellite, telephone lines, TV cable networks, etc.

Analysis Station

Each Analysis Station consists of a computer equipped with a video monitor, preferably color, and input means. As stated heretofore, the input means can be a touch sensitive screen, keyboard or other input means used in the art. The computer must be equipped with two ports which are compatible with the analyzer and monitor. It is advantageous in many applications to provide a printer to provide hard copies of the screen results. Software has been written to display choices of patient demographics, analytical tests to be performed, and modifications to the outputted data (e.g. patient temperature and hemoglobin which influence the calculation of the results of the analysis) which may be selected by the user of the laboratory.

In the Stand Alone Analysis Station a user inserts the sample into the analytical instrument, allowing the instrument to aspirate the required amount of specimen.

In the Remote Analysis Station, the user places a sample on a receiving area, thereby activating the robotic arm to commence processing of the sample. The robot arm allows rapid entry of multiple specimens as well as totally unattended operation.

The arm used is a commercial laboratory robot (CRS, Plus, Toronto, Canada). Additional components of the robot include the robot controller and host microcomputer. In addition the robot comes equipped with gripper sensors which give feedback indication of the forces applied by the robot fingers. Gripper sensors provide simple touch sensing which can detect the presence or absence of an object in the robot end effectors.

The robot is programmed to perform simple "pick and place" operations on 3 mL plastic syringes containing whole blood, and also is trained to use several peripheral tools designed for complex procedures such as cap removal and replacement, specimen mixing, and air bubble removal (burper). The CRS robot arm is capable of a high degree of repetitive movement precision (repeatability of 0.05 mm). To maintain such precision an orientation device is incorporated into the design of the robot environment to allow the robot to recalibrate its location should it become disoriented.

One advantage to the Remote Analysis Station is the ability to include multiple analytical instruments within the reach of the robot. This allows for a wide variety of tests to be run on multiple analyzers with only one sample and a one time effort by the user.

The interactive system allows the user to select a specific analysis to be run from the analysis available on the particular instrument. Although only the specific analysis are displayed, the entire profile capable by the analysis instrument is actually measured on each sample. The running of the entire profile is advantageous in several ways. The interface is simpler to write, as the selected tests do not have to be sorted from the unselected tests. Although the unselected tests could be eliminated at the server, the accessibility of all tests capable of being run is an advantage. For example, in the event only a blood gas is initially requested, however subsequently it is decided that results on the remaining available tests are required, these test will be available. Other parameters such as $FlO_2$ and patient temperature can be adjusted and default values of no NFG ($FlO_2$ given, and $37°$) are incorporated for the convenience of the user.

The programs that run on the Analysis Station computer are all written in the computer language called "C". The compiler is called Turbo C, version 2.0 which takes the "C" source code and compiles it into an executable program. Paradox 4.0 is a commercial database program; Paradox Engines, version 2.0 is a set of functions called libraries that are used with the "C" source code. These functions allow the programmer to access the Paradox database files. No programs were written in Paradox. They were written in "C" using the Paradox Engine functions to access the Paradox databases.

The Analysis Stations can be located in a variety of locations within the same hospital which house the Laboratory Unit at various doctors offices, clinics or hospitals or a combination thereof.

Analyzer to Computer Interface

There are three basic areas in which instrument standardization is necessary: sample preparation and introduction, operator input of information to the analyzer, and output of information from the analyzer to the user. In order to standardize these areas interfaces are incorporated. An universal interface was disclosed in U.S. Ser. No. 07/739,204, which has been incorporated herein, wherein a system simplified communication between a microcomputer and clinical instrument by establishing a standardized bi-directional communications protocol. Both the universal interface and the dedicated interface operate on the same basic principle—translation of instrument codes to interactive program codes and vise versa.

Clinical analysis instruments, even if computer compatible, are not designed for interactive analysis. Hence, the need for standardization of data communications and analyzer interface hardware. The interface translates input commands to codes or actions recognizable by the analyzer. Features not normally available to the user, such as electrode real-time response and full instrument status, are also reported by the interface, thereby establishing a remote monitor and control mechanism for the interfaced instrument. The operating system controls the interface, which in turn commands and monitors the clinical analyzer. The server controls the information flow to the interface and provides (a) requests to the interface for instrument operation and status and (b) commands to the interface to initiate the desired instrument operation. This arrangement maintains complete instrument functionality as designed by the manufacturer while allowing remote monitoring and operation of the instrument.

The interface is designed to minimize modifications of the commercial analytical instrument. The analytical instrument control signals are translated, through use of a look-up table, into a standardized format on an erasable/programmable read only memory (EPROM) chip contained on an interface card. This format is compatible with signals used in the remote Analysis Stations. This translation allows rapid interfacing of a variety of analytical instruments which potentially could be incorporated into the laboratory unit. Furthermore, the interface card facilitates packaging of the instrument output into a format that simplifies communication software at the host computer. The interface permits remote control of all calibration cycles, chamber evacuation, washes and sampling mode, retrieval of patient and calibration results, initiation of instrument settings for the patient's temperature and hemoglobin concentration, barometric pressure, time, and date.

Standard electronic hardware is used in the design of both the universal and dedicated interfaces, which are based on Intel Corporation (Santa Clara, Calif.) integrated circuits, microprocessor, a peripheral interface adapter, universal synchronous/asynchronous receiver/transmitter, erasable programmable read-only memory, static random-access memory, and support circuitry compose the interface microcomputer.

A unique set of software commands, within the universal interface, is used for each clinical instrument to allow the instrument to be controlled by the interface. The instrument-specific software translates instrument data into a standardized string for transmission to a host computer. Alternatively, specific software can be written for each analytical instrument used as a "dedicated" interface. Although not as convenient as a universal interface, dedicated interfaces can be used to overcome specific hardware problems encountered in less compatible instruments.

In a universal analytical instrument interface, a standardized output string for each instrument is made up of an instrument identifier, a mode of operation, the instrument command, device real-time status, results, error checking, and a transmission terminator. The instrument identifier field holds a lead character and a two-digit number (e.g., Corning:

COI). The mode of operation can be a single ASCII character, ie. A—Automatic, C—Command, D—Diagnostic, E—Error, R—Results. The default mode is Command. If the interface detects an instrument operational error, the Error mode is indicated. The Diagnostic mode can be set by the host computer to enable routines on board the interface to assist in instrument evaluation and trouble shooting. The Automatic mode, also externally selectable, assists in the quality-control operation of the instrument. Both of the interfaces are capable of automatically testing calibration results and operations and, if an error is detected, a selected number of attempts to correct the malfunction are initiated.

The Command-field is a character selected from a standard command set developed for this interface. Use of a standard Command set for all target analyzers simplifies the interface/operating system instrument control routines. The Command set is divided into subsets that perform calibrations, retrieve data, set operation parameters, ascertain device status, and control manual instrument function. One set of commands for any instrument or group of instruments reduces the demands on the host computer for specific device evaluation. Instrument real-time status is an 11-character set and decoded to indicate full instrument operational status. Most target instrument functions can be indicated within this field.

Instrument results are within delimiting brackets to allow ease of extracting results. Any sequence of instrument results could be mimicked by other similar devices used with the interface. For example, if two different blood gas analyzers are controlled by an interface, both will report results in the same sequence, irrespective of the original manufacturer's design (pH, $pCO_2$, $pO_2$, etc). This sequencing allows the host computer to be unaffected by changes resulting from manufacturer design or user instrument selection, which simplifies instrument control and processing of results.

As an example of a dedicated interface, modifications to the Corning 178 blood gas analyzer were limited to removal of a switch logic board (board no. 7) and replacement with a connector card and custom cable. Commands that the blood gas analyzer used to initiate operation were loaded to a particular personality card memory location and an interrupt was triggered. Data as well as instrument operation were indicated from the memory output and, with proper decoding, a real-time status was returned. Use of the real-time scan gives the Laboratory Unit full monitoring of the blood gas analyzer and, in conjunction with the input Commands, complete control and remote monitoring of the analyzer. An added benefit offered by the real-time scan was monitoring of electrode response of the analyzer at any time. The addition of this scan, provided the ability to trouble shoot instrument errors from a remote site.

Analytical Instrument

Any commercially available computer compatible analytical instrument, such as the Nova Stat 5, can be placed in the Analysis Station because of the unique design of the interfaces, hardware, and software. The analytical instrument must, however, have the ability to be automated and capable of being interfaced, either with a universal or dedicated interface, with a computerized system. Currently available instruments are not generally manufactured to be interactive with computerized systems, however alterations can readily be made to interface these instruments with the instant system. Instruments which cannot be incorporated with the instant systems are those which require human input on a step by step basis. Instruments which do not have the capability to be totally automated, can be utilized with the system on a limited basis. It should be noted herein that although analytical instruments, such as a blood gas analyzer is being described herein, any medical instrument which can be made compatible with a computerized system can be controlled and monitored through the instant system.

The system, as disclosed herein, is referring to laboratory to remote instrument interaction. This interaction can be between the Laboratory Unit and multiple Stand Alone and/or Automated Analysis Stations instruments. However as each interaction takes the same route, for simplicity the interaction between the Laboratory Unit and a single Analysis Station will be described herein.

Many instruments used in the clinical Laboratory are designed to be autonomous, easy-to-operate devices. Provisions are made for sample introduction, user data input through a keypad or other peripheral device, and reporting instrument status and test data. Instrument operation is controlled by the user or by an internal computer that coordinates instrument operation. Each manufacturer of laboratory instrumentation follows its own protocol for device control commands and instrument communications. Often data from the analyzer is limited solely to final calibration set point reports and results for patients' samples. Most instruments will report derived data to an external device, such as a printer or host computer, according to established communications protocols (RS-232C, Electronic Industry Association Recommended Standard 232, version C).

Operational control and monitoring of an analyzer must not only include access to the data produced by the instrument but also allow for total peripheral control of the analyzer.

PROCESS SEQUENCE

Server

The server is a storage and manipulation device used in the standard network manner as well known in the prior art. The uniqueness lies in the software which enables the hardware to interact with the Analysis Stations and Laboratory Unit.

Laboratory Unit

1. The system hardware is checked for existence of monitoring equipment.

2. The database file access is established.

3. If 1 or 2 above do not meet the predetermined standards, the system is aborted. Errors can be displayed on the screen and a reset opportunity presented after error correction.

4. The Laboratory Unit program periodically checks the server to determine if unprocessed analysis results have been received from the analytical instrument. The time period between checks with the server can be set by the Medical Technician Operator and can vary based on time of day. If no results are present for the Operator's review, the save screen is initiated. If results are present for viewing, the program proceeds to the next Command.

5. Once an unprocessed test result is recognized in the Laboratory Unit, the result is retrieved by the Laboratory Unit.

6. Upon receipt of the unprocessed test result, a display is brought up onto the monitor showing the units where the sample originated. Simultaneously, an alarm is activated at periodic time intervals to alert the Operator. An audio alarm is generally utilized, however any type of appropriate alarm or combination can be used.

7. The alarm is deactivated upon Operator's input and the commencement of program activation.

8. Once acknowledged the test results are displayed on the screen displaying the test results in the programmed format. The amount of data on the screen can vary based on hospital policy, Operator's preference, etc. This can include a request for past test results or other patient information which has been incorporated within the program for access.

9. Operator's ID codes are requested to verify that the Operator reading the results is known to the system. If incorrect ID is entered, the system goes back to step 6.

10. The screen remains active until an indication of acceptance or rejection is received.

11. Upon acceptance of the test results, the Laboratory Unit program returns the accepted results to the appropriate database within the server. Once returned to the server, the test results are available to the Analysis Station on request basis. As an alternative, an indicator can be provided at the Analysis Station monitor to indicate the completion of the analysis review. Alternatively, a hard copy print out can be automatically provided once the test results are obtained by the server.

12. The accepted test results are transmitted to the hospital main computer database for storage.

13. Rejected test results are returned to the server and saved until manual or global deletion.

14. The system is them reset, returning to step (4).

Analysis Station

The Analysis Station preferably has accessible three modes, Analysis, Review and Maintenance.

Analysis Mode

1. Check system hardware for existence of monitor equipment.

2. Establish database file access (open database engines), and read "COUNT" database for Patient sample number.

3. Establish serial connection with analyzer

4. Initialize analyzer to standby mode

5. If any of steps (1)–(4) fail, the system will abort the remaining sequence and display the error reading on the screen.

6. Upon activation by user, ID is requested and can be, if desired, a double entry verification system.

7. The system waits for the user to enter the appropriate Login ID sequence. If interaction time is exceeded, the system returns to save screen. Although not critical, it is preferable to have a "save screen function" incorporated in the system to protect the monitor.

8. The user access and verify codes are tested for correctness. If either the access or verify code is incorrect, the system remains on the login screen to allow unlimited attempts to access the system. The system will go to the save screen at a predetermined time if there is no user interaction.

9. Screen displays Mode Selection based upon the user's ID codes. If the codes indicate an engineer or medical technologist is operating the system a Maintenance Mode will appear (Step 39). ID codes representing a user (nurse, aide, etc.) will display the analyze/review screen. An entry of Analysis proceeds to Step 10; and entry of Review proceeds to Step 29.

10. The system checks the analyzer to confirm that the instrument is ready for analysis. If it is not ready, an alarm is activated to advise the user that the system is not available. The screen goes to the login screen of Step 7.

11. The Analyze sample screen is displayed, enabling relevant commands (scroll up, down, enter, search by ID number, esc).

12. The screen displays a list of valid units from the "UNITS" database, defaulting to last selected unit by given user. The default unit follows the different access codes.

13. The system waits for the user to select the desired unit. In the event the user selects the ID option, the system goes to Step 26. If there is no interaction with the system the login screen is reactivated and the system returns to Step 7.

14. Once the unit is selected the user searches the patient roster database, "PATIENTS", for patients in the given unit.

15. The system displays the "Select Patient" screen, selected unit name and enables relevant commands (scroll up, down, enter, search by ID Number, esc).

16. The screen displays a list of valid patients for the selected unit.

17. The system waits for the user to select the desired patient. If the dead time is exceeded the system returns to the login screen at Step 7.

18. The system displays the patient demographics screen with relevant commands enabled (Patient temp, Fio2, Coding, test profile, enter, clear, esc).

19. The system displays the selected patient, ID number and location. Displays default values for temp (37.0° C.), fio2 (%), coding, test profile.

20. The system waits for the user to select the desired patient demographics. If interaction time is exceeded, the system returns to the login screen at Step 7.

21. Upon user pressing "Enter", the analyzer is prepared for analysis, the user is prompted to place valid sample in the docking port.

22. Once the analyzer probe is fully extended, a command to proceed with sample aspiration is sent. Upon sample retrieval, the system alerts the user to remove sample from the port. A patient sample number (an internal number generated by the software to provide a unique patient ID) is incremented and stored in the "COUNT" database.

23. Normal instrument function continues until the sample analysis is complete. Once operation is complete, the instrument is queried, by the system, for results and errors.

24. The results, patient demographics, and instrument errors are stored in the results database "RAW".

25. The instrument continues its normal analysis cycle of washing out. Displays "Instrument Washout". At the completion of the washout cycle, the system goes to the login screen at Step 7.

26. If the search by patient ID option is chosen in Step 13, the system displays the Search by ID screen and enables relevant commands (numeric pad, clear, enter).

27. The system prompts the user to enter desired ID. If no response from the user is entered within the specified time the system returns to the login screen at Step 7.

28. User enters the Patient ID and the system searches patient database "PATIENTS" for matching ID number. If the ID is present the system goes to Step 14. If the ID is not located the screen shows "Invalid ID" and allows re-entry of ID number.

Review Mode

29. The system displays the "review results" screen and enables relevant commands (scroll up, down, enter, search by ID number, esc).

30. A list of valid units in "UNITS" database is displayed, defaulting to the last selected unit by given user. The default unit follows the different access codes.

31. The system waits for the user to select desired unit. If the user selects to search by ID, the system goes to Step 42. If inactivation time is exceeded the screen returns to the login screen of Step 7.

32. The selected unit is used to search the patient roster database for patients in the given unit.

33. The system displays the "Select Patient" screen, selected unit name and enables relevant commands (scroll up, down, enter, search by ID Number, esc).

34. The system displays a list of valid patients for the selected unit.

35. The system waits for the user to select the desired patient. If interaction time is exceeded, the system returns to login screen at Step 7.

36. The patient results screen is displayed with relevant commands (print results, display previous 10 results, esc).

37. Patient results and demographics are displayed giving analysis results, pending or failed.

38. The system waits for user input. The user can chose to "clear" or "print and clear". If interaction time is exceeded, it returns to login screen at Step 7.

Maintenance Mode

39. The system displays instrument maintenance screen with relevant commands (all switches available on analyzer, esc.).

40. Wait for Operator input. If interaction time is exceeded the screen goes to login screen at Step 7.

Automated Analysis Station

The automated analysis station is disclosed in its entirety in the copending parent application. To maintain a continuity and to demonstrate the compatibility of the automated and stand alone systems, the following automated analytical sequence is set forth briefly as follows:

41. Steps 1 through 20 are same as Stand Alone Analysis Station.

42. The system requests the robot computer to open the receiving area door.

43. The system requests the user to place the sample in a single sample receptacle. If the sample is not received within the receptacle within the predetermined time, the system returns to Step 7.

44. Verification of the analysis and placement of the sample is requested by the system. If interaction time is exceeded, the system returns to login screen at Step 7.

45. Upon verification, the system closes the door and instructs the robot to begin the analytical sequence.

46. The robot lowers its actuators (fingers), grasps the syringe and moves it to a mixing chilling chamber.

47. Following a 30 second mixing chilling cycle, the syringe is removed from the mixer by the robot which then places it in a pneumatically driven uncapping device.

48. The system determines if there is sufficient sample volume for an accurate blood analysis. If all system checks are acceptable then the robot closes its end effectors to grasp the syringe at the correct location for accurate insertion into the instrument. In the event all system checks are not acceptable, the screen displays an error message and activates an audible alarm.

49. The system rechecks the readiness of the analysis instrument. If the instrument does not indicate "ready" the system displays an error message and activates the alarm.

50. Upon issuance of the ready mode, the robot places the syringe into the sample port of the instrument.

51. The instrument aspirates the required volume of the specimen and initiates the analysis.

52. The instrument sends a completed signal to the system instructing removal of the specimen.

53. The system directs the robot to position the syringe in the burper which ejects the air bubble by advancing the syringe plunger and simultaneously washing the tip.

54. The system returns the syringe to the decapping/capping station for recapping.

55. Once recapped, the syringe is returned to the mixer chiller to maintain specimen integrity.

56. Repeat of Steps 24–28 of Stand Alone Analysis Station.

57. Upon receipt of an acceptance from the Laboratory Unit the robot is directed to remove the syringe from storage for appropriate disposal.

58. Upon review, if the sample is not acceptable a retest can be ordered at which time Steps 47–56 are repeated.

Use of the Automated Analysis Station allows for a retesting using the same sample to be done at the discretion of the reviewing medical technologist.

FIG. 1 is a flow diagram of the interactive system 10. The Analysis Station 12 is provided with a CPU 14 as described in more detail heretofore. The flow of the information from Analysis Station 12 to Laboratory Unit 18 is identical whether the Analysis Station 12 is a Remote or Stand Alone unit. The data received from the CPU 14 is transmitted to the server 16 where it is processed. The server 16 contacts the hospital information system 22, through the LIS interface 20, to obtain patient information. The server 16's request is through use of the patient identification to obtain patient statistics required for analysis of the test results. Upon receipt of the patient information and calculation of values, the information is transmitted, upon request, to the Laboratory Unit 18. At the Laboratory Unit 18 the information is reviewed and accepted or rejected as described above. The results are sent back to the server 16 where they are "sorted". The rejected tests are sent back to the Analysis Station 12 where the user is notified of the rejection. The accepted results are sent to the Analysis Station 12 and to the hospital information system 22 where they are stored in the patients database.

FIGS. 2–5 illustrate, in flow diagrams, the program for the Laboratory Unit as described in the following code.

```
24      /*
        mas_sc.c version 1.0 8/94 Laboratory Unit
25      */
        #include <bios.h>
26      #include <conio.h>
        #include <dos.h>
27      #include <fcntl.h>
        #include <io.h>
28      #include <math.h>
        #include <pxengine.h>
29      #include <stdio.h>
        #include <stdlib.h>
30      #include <string.h>
        #include <sys\types.h>
31      #include <sys\stat.h>
        #include <time.h>
32      /*
        results structure
33              temp - patient temperature
                bp - barometric pressure in mmhg
34              ph - [hydrogen]
                pco2 - partial pressure of carbon dioxide in sample
35              po2 - partial pressure of oxygen in sample
                hct - sample hematocrit
```

```
              na - [Sodium]
              k - [Potassium]
              cl - [Cholride]
              ca - [Calcium]
              gluc - [Glucose]
              lac - [Lactate]
              sn - sequence number
              done_date - sample date complete
              ssn - social security number
              accees - access code
              patient_name -
              done_time - sample done time
              verify_time - sample verify time
              device_location - location of system
              status - sample status
              tech_number - technologist number
              verify - verify code
              profile - panel of tests run
              instrument_errors - errors present on analyzer
              unit - location of patient
              sample_type - artieral/venous
              fio2 - fraction of inhaled oxygen
              flag -
        */
              typedef struct {
                      double temp, ph, pco2, po2, hct, na, k, cl, ca, gluc, lac;
                      long sn, done_date;
                      char ssn[10], access[10];
                      char patient_name[20], done_time[9], verify_time[9];
                      char device_location[10], status[10] ,tech_number[10], verify[10];
                      char profile[20], instrument_errors[40], unit[10];
                      short sample_type, fio2;
                      unsigned flag:1;
              } RESULTS;
        /*
        previous_results structure
              temp - patient temperature
              ph - [hydrogen]
              pco2 - partial pressure of carbon dioxide in sample
              po2 - partial pressure of oxygen in sample
              hct - sample hematocrit
              na - [Sodium]
              k - [Potassium]
              cl - [Cholride]
              ca - [Calcium]
              gluc - [Glucose]
              lac - [Lactate]
              done_date - sample date complete
              done_time - sample done time
              status - sample status
              profile - panel of tests run
              sample_type - artieral/venous
        */
              typedef struct {
                      double ph, pco2, po2, hct, na, k, cl, ca, gluc, lac, temp;
                      long done_date;
                      char status[7], profile[20], done_time[9];
                      short sample_type;
              } PREVIOUS_RESULTS;
        /*
        time structure
              current_date - current file name
              long_time - time in seconds
              year
              month   self explanatory
              day
        */
              typedef struct {
                      char current_date[25];
                      long long_time;
```

```
1                  int year, month, day;
            } TIME;
2      /*
              date structure
3             previous_date - previous file date for review of results
       */
4             typedef struct {
                      char previous_date[25];
5             } DATE;
       /*
6             px structure
              total_records - count of results in uva_raw.db
7             num - current number of record processed
       */
8             typedef    struct {
                      RESULTS results;
9                     PREVIOUS_RESULTS previous_results[10];
                      DATE date;
10                    TIME time;
                      long max_rec, num_rec, num;
11                    unsigned tblhdl;
                      int total_records;
12            } PX;
       long pxtime(PX *);
13     char *status_name[] = {"????", "FAIL", "ACCEPT", "!!!!"};
       main()
14     {
              PX px;
15            time_t bintime, tnow;
              int    touch_handle = 0, pc, sample_status;
16            char entry[0x10];
              px.max_rec = px.num_rec = px.results.flag = 0;
17            textbackground(BLACK);
              clrscr();
18            cursor_on_off(0);
              /*
19                    initialize paradox operations
              */
20            PXNetInit("h:\\db\\", NETSHARE,"MAS_SC");
              printf("Database Initialized\n");
21            /* open touch handle for use and load pads*/
              touch_handle = open("TCH_SCRN", O_BINARY|O_RDWR, S_IWRITE);
22            if(touch_handle > 0){
                      touch(touch_handle, "init", entry);
23                    touch(touch_handle, "padload satcen", entry);
                      printf("Touch pads have been loaded\n");
24            }
              else   touch_handle = 0;
25            /*
                      main control loop
26            */
              do {
27                    /*
                              check for next access of lan files
28                    */
                      time_change(&px);
29                    /*
                              check file for new results
30                    */
                      if(!(pc = process_control(&px))){
31                            clrscr();
                              /*
32                                    display results and alert technologist
                              */
33                            if((sample_status =
                                      results_screen(&px, touch_handle)) < 0){
34                                    px.num_rec++;
                                      continue;
35                            }
                              if(verifying_tech_code(touch_handle, &px)) continue;
```

```
                        /*
                                sample verified by tech
                        */
                        printer_status();
                        fprintf(stdprn, "          Status: %s\n", status_name[sample_status]);
                        fprintf(stdprn," Tech Id: %s\n", px.results.tech_number);
                        fprintf(stdprn,"----------------------------------------\n\n\n\n\n\n\n");
                        change_sample_status(&px, sample_status);
                        px.num_rec++;
                }
                else if(pc != 1) fprintf(stdprn, "system error %d\n", pc);
                idle_screen();
                px.results.flag = 0;
                time(&bintime);
                /*
                        location for roster - not in place !!!
                */
                do{
                        if(px.max_rec > px.num_rec) break;
                        touch(touch_handle, "mode pad", entry);
                        if(entry[0] == 'F'){
                                beep(1000);
                                if(verifying_tech_code(touch_handle, &px)) break;
                                else{
                                        /*
                                                valid tech entry
                                        */
                                        puts("\377\377 progs/");
                                        touch(touch_handle,"group all off",entry);
                                        touch(touch_handle,"group 7 on",entry);

get_touch(touch_handle, entry, &px);
                                        beep(700);
                                        if(entry[2] == 'R'){
                                                /*
                                                        roster
                                                */
                                        }
                                        clrscr();
                                        idle_screen();
                                        px.results.flag = 0;
                                }
                        }
                }while(time(&tnow) < bintime + 15);
        } while(1);
}
/*
        NAME:       beep - alerts operator
        INPUT:      freq - desired frequency for beeper
        RETURN:     none
*/
beep(int freq)
{
        sound(freq);
        delay(75);
        nosound();
}
/*
        NAME:       calculate_gas_correction - temperature correction of gas values
        INPUT:      ph, pco2, po2, temp
        RETURN:     temperature corrected ph, pco2, po2
*/ calculate_gas_correction(double *ph, double *pco2,
                                              double *po2, double *temp)
{
        double x, y, z;
        if(*ph > 0.0) *ph -= (0.015 * (*temp - 37.0));
        if(*pco2 > 0.0) {
                *pco2 = *pco2 * pow(10,(0.019 * (*temp - 37.0)));
        }
        if(*po2 > 0.0) {
```

```
              z = exp(3.88 * log(*po2));
              x = 5.49e-11 * z + 0.071;
              y = 9.72e-09 * z + 2.30;
              *po2 = *po2 * exp(2.303 * (*temp - 37.0) * x/y);
       }
}/*
       NAME:      change_sample_status - changes sample status after tech hase responded
       INPUT:     new sample status
                  px structure for tech access code
       RETURN:    db record updated to proper status and tech code
*/change_sample_status(PX *px, int sample_status)
{
       char devloc[10], status[7], stat[10], *time_ptr;
       unsigned rechdl;
       long first_results_record_number;
       char *status_name[] = {"????", "FAIL", "ACCEPT"};
       pxtime(px);
       /*
              open uva_raw.db
       */
       PXTblOpen("h:\\db\\uva_raw", &px->tblhdl, 0, 1);
       PXRecBufOpen(px->tblhdl, &rechdl);
       /*
              search for proper sequence number
       */
       PXPutLong(rechdl, 5, px->results.sn);
       if(PXSrchFld(px->tblhdl, rechdl, 5, SEARCHFIRST) == PXSUCCESS) {
              PXRecNum(px->tblhdl, &first_results_record_number);
              PXRecGet(px->tblhdl, rechdl);
              /*
                     get status and device location
              */
              PXGetAlpha(rechdl, 23, 7, status);
              PXGetAlpha(rechdl, 19, 10, devloc);
              if(strstr(status,"DONE")){
                     /*
                            if done - change status
                     */
                     PXPutAlpha(rechdl, 23, status_name[sample_status]);
                     strcpy(px->results.status, status_name[sample_status]);
                     PXPutAlpha(rechdl, 24, px->results.tech_number);
                     PXPutAlpha(rechdl, 22, px->results.verify_time);
                     PXRecUpdate(px->tblhdl, rechdl);
              }
       }
       PXRecBufClose(rechdl);
       PXTblClose(px->tblhdl);
}
/*
       NAME:      check_valid_error - check instrument error for reporting
       INPUT:     error code to be tested
       RETURN:    0 - OK to display error
                  1 - do not display
*/
check_valid_error(char *error_code)
{
       char *errors[] = {"H0", NULL};
       int i = 0;
       while(errors[i]){
              if(!strcmp(error_code, errors[i++])) return(0);
       }
       return(1);
}
/*
       NAME:      copy_current_date_table - make a copy of raw to current date file
       INPUT:     uva_raw.db
       RETURN:    h:\\db\\uv_"current date".db
*/
copy_current_date_table(PX *px)
```

```
1   {
            yesterday(px);
2           PXTblCopy("h:\\db\\uva_raw", px->time.current_date);
            return(0);
3   }
    /*
4           NAME:       cursor_on_off - turn cursor off or on
                INPUT:      flag 0 - on; 1 = off
5           RETURN:     none
    */
6   cursor_on_off(int flag)
        {
7           union REGS xr;
            if(!flag){
8               xr.h.ah = 1;
                xr.h.ch = 0x20;
9               xr.h.cl = 0;
                int86(0x10, &xr, &xr);
10          }
            else{
11              xr.h.ah = 1;
                xr.h.ch = 7;
12              xr.h.cl = 8;
                int86(0x10, &xr, &xr);
13          }
            return(flag);
14  }
    /*
15          NAME:       delete_records - remove processed sample records from uva_raw.db
                INPUT:      uva_raw.db
16          RETURN:     cleared db
    */
17  delete_records(PX *px)
        {
18          int i, record_to_get = 1;
            long records_remaining, total_records;
19          char status[7];
            unsigned     tblhdl, rechdl;
20          /*
                        open uva_raw.db & get total # records
21          */
            PXTblOpen("h:\\db\\uva_raw", &tblhdl, 0, 1);
22          PXTblNRecs(tblhdl, &total_records);
            records_remaining = total_records;
23          PXRecBufOpen(tblhdl, &rechdl);
            gotoxy(45,24);
24          printf("Records remaining to delete:");
            for(i = 1; i <= total_records; i++, --records_remaining) {
25              /*
                        delete processed records
26              */
                PXRecGoto(tblhdl, record_to_get);
27              PXRecGet(tblhdl, rechdl);
                PXGetAlpha(rechdl, 23, 7, status);
28              gotoxy(74, 24);
                printf("%5d", records_remaining);
29              if((!strcmp(status, "ACCEPT")) || (!strcmp(status, "FAIL")))
    PXRecDelete(tblhdl);
30              else record_to_get++;
            }
31          PXRecBufClose(rechdl);
            PXTblClose(tblhdl);
32  }
    /*
33          NAME:       display_delta_check - displays the delta_check values
                INPUT:      results in px structure
34          RETURN:     none
    */
35  display_delta_check(PX *px)
        {
```

```
1       int text = RED, display_on = 0, prev_data = 0;
        char *month[]={"Jan","Feb","Mar","Apr","May","Jun",
2                                              "Jul","Aug","Sep","Oct","Nov","Dec"};
        /*
3               find previous accepted result for displayed patient
        */
4       while(prev_data <= px->total_records){
                if(!strncmp(px->previous_results[prev_data].status,"ACCEPT", 6)) break;
5               else prev_data++;
        }
6       /*
                decode date for display
7       */
        PXDateDecode(px->previous_results[prev_data].done_date, &px->time.month, &px-
8       >time.day, &px->time.year);
        if(!px->previous_results[prev_data].sample_type) text = LIGHTBLUE;
9       textcolor(text);
        /*
10              display delta hct if out of range
        */
11      if((px->results.hct > 0) && (px->previous_results[prev_data].hct > 0)) {
                if(abs(px->results.hct - px->previous_results[prev_data].hct) > 3.0) {
12                      gotoxy(11, 14);
                        cprintf("%3.0f", px->previous_results[prev_data].hct);
13                      display_on = 1;
                }
14      }
        /*
15              display delta na if out of range
        */
16      if((px->results.na > 0) && (px->previous_results[prev_data].na > 0)) {
                if(abs(px->results.na - px->previous_results[prev_data].na) > 10.0) {
17                      gotoxy(10, 15);
                        if(px->previous_results[prev_data].na > 0.0){
18                              cprintf("%5.1f", px->previous_results[prev_data].na);
                                display_on = 1;
19                      }
                        else{
20                              if(px->previous_results[prev_data].na == -2) cprintf("-2");
                                else cprintf("-1");
21                      }
                }
22      }
        /*
23              display delta k if out of range
        */
24      if((px->results.k > 0.0) && (px->previous_results[prev_data].k > 0.0)) {
                if(abs(px->results.k - px->previous_results[prev_data].k) >
25                                                              (px->results.k * 0.5))
        {
26                      gotoxy(10,16);
                        if(px->previous_results[prev_data].k > 0.0){
27                              cprintf("%4.1f",px->previous_results[prev_data].k);
                                display_on = 1;
28                      }
                        else{
29                              if(px->previous_results[prev_data].k == -2) cprintf("-2");
                                else cprintf("-1");
30                      }
                }
31      }
        /*
32              display delta cl if out of range
        */
33      if((px->results.cl > 0) && (px->previous_results[prev_data].cl > 0)) {
                if(abs(px->results.cl - px->previous_results[prev_data].cl) >
34                                                              (px->results.cl * 0.2))
        {
35                      gotoxy(10,17);
                        if(px->previous_results[prev_data].cl > 0.0){
```

```
                              cprintf("%4.0f",px->previous_results[prev_data].cl);
                              display_on = 1;
                 }
              else{
                    if(px->previous_results[prev_data].cl == -2) cprintf("-2");
                    else cprintf("-1");
              }
         }
    }
/*
         display delta gluc if out of range
*/
    if((px->results.gluc > 0) && (px->previous_results[prev_data].gluc > 0)) {
         if(abs(px->results.gluc - px->previous_results[prev_data].gluc) > 300.0) {
              gotoxy(10,19);
              if(px->previous_results[prev_data].gluc > 0.0){
                    cprintf("%4.0f",px->previous_results[prev_data].gluc);
                    display_on = 1;
              }
              else{
                    if(px->previous_results[prev_data].gluc == -2) cprintf("-2");
                    else cprintf("-1");
              }
         }
    }
    /* display date and time*/
    if(display_on){
         gotoxy(3,11);
         cprintf("%s%d", month[px->time.month - 1],
                                                          px->time.day);
         gotoxy(9,11);
         cprintf("%s",px->previous_results[prev_data].done_time);
    }
}
/*
    NAME:       display_instrument_errors - display error explanation from
nova_err.db
    INPUT:      nova_err.db
    RETURN:     displays text error messages on screen
*/
display_instrument_errors(PX *px)
{
    char tokens[] = "{}", *error_code, description[30], err[40];
    char error_type[10];
    int i, row = 11;
    TABLEHANDLE    tblhdl;
    RECORDHANDLE   rechdl;
    textcolor(YELLOW);
    PXTblOpen("h:\\satcen\\nova_err", &tblhdl, 0, 1);
    PXRecBufOpen(tblhdl, &rechdl);
    strcpy(err, px->results.instrument_errors);
    error_code = strtok(err, tokens);
    if(check_valid_error(error_code)){
         /* or code match and display*/
         PXPutAlpha(rechdl, 1, error_code);
         if(PXSrchFld(tblhdl, rechdl, 1, SEARCHFIRST) == PXSUCCESS) {
              PXRecGet(tblhdl, rechdl);
              PXGetAlpha(rechdl, 2, 30, description);
              PXGetAlpha(rechdl, 3, 10,         error_type);
              /*
                    if coding patient - alert tech
              */
              if (!strcmp(error_code,"CP")) {
                    textcolor(MAGENTA + BLINK);
                    for(i = 0; i < 5; i++) {
                         beep(800);
                         beep(400);
                    }
              }
              gotoxy(50, row);
```

```
                    cprintf("%s", description);
                    gotoxy(71, row++);
                    cprintf("%s", error_type);
                    if (!strcmp(error_code,"CP")) textcolor(YELLOW + !BLINK);
                }
        }
        /*
                continue search and display of instrument errors
        */
        while ((error_code = strtok(NULL, tokens)) != NULL) {
                if(check_valid_error(error_code)){
                        PXPutAlpha(rechdl, 1, error_code);
                        if(PXSrchFld(tblhdl, rechdl, 1, SEARCHFIRST) == PXSUCCESS) {
                                PXRecGet(tblhdl, rechdl);
                                PXGetAlpha(rechdl, 2, 30, description);
                                PXGetAlpha(rechdl, 3, 10, error_type);
                                /*
                                        alert tech if coding patient
                                */
                                if(!strcmp(error_code,"CP")) {
                                        textcolor(MAGENTA + BLINK);
                                        for(i = 0; i < 5; i++) {
                                                beep(800);
                                                beep(400);
                                        }
                                }
                                gotoxy(50, row);
                                cprintf("%s", description);
                                gotoxy(71, row++);
                                cprintf("%s", error_type);
                                if (!strcmp(error_code, "CP")) textcolor(YELLOW + !BLINK);
                        }
                }
        }
        PXRecBufClose(rechdl);
        PXTblClose(tblhdl);
}
/*
        NAME:       display_patient_info - displays patient demographics information INPUT:      patient data in px structure RETURN:     displays patient data
*/
display_patient_info(PX *px)
{
        textcolor(BLACK);
        textbackground(LIGHTGRAY);
        gotoxy(10, 7);
        cprintf("%s", px->results.patient_name);
        gotoxy(10, 8);
        cprintf("%s", px->results.ssn);
        gotoxy(34, 7);
        cprintf("%s", px->results.unit);
        gotoxy(43, 8);
        cprintf("%s", px->results.device_location);
        gotoxy(50, 7);
        cprintf("%-15s", px->results.access);
        gotoxy(56, 8);
        cprintf("%4.1f", px->results.temp);
        gotoxy(72, 7);
        cprintf("%s", px->results.done_time);
        gotoxy(72, 8);
        if(px->results.fio2 == -1) cprintf("NFG");
        else cprintf("%d %% ", px->results.fio2);
        gotoxy(20, 10);
        cprintf("%s", px->results.profile);
}
/*
        NAME:       display_previous_results - display previous 10 patient results
```

```
                INPUT:  previous storage in px structure
                RETURN:    10 previous patient results
        */
        display_previous_results(PX *px)
        {
                int text = RED, j, row;
                char *month[] = {"Jan","Feb","Mar","Apr","May","Jun",
                                 "Jul","Aug","Sep","Oct","Nov","Dec"};
                /*
                        display patient demographics and remove unit, seq number, time
                */
                display_patient_info(px);
                textcolor(WHITE);
                textbackground(LIGHTGRAY);
                gotoxy(40, 7);
                for(j=0;j<40;j++) putch(0x20);
                gotoxy(25, 8);
                for(j=0;j<55;j++) putch(0x20);
                gotoxy(20, 10);
                for(j=0;j<19;j++) putch(0x20);
                for (j = 0, row = 10; j < px->total_records; j++, row++) {
                        if(row == 11) row++;
                        /*
                                select color to display results yellow - failed
                                                                        blue - venous
                                                                        red - accepted
                        */
                        if(!strcmp(px->previous_results[j].status,"FAIL")) text = YELLOW;
                        else if(!px->previous_results[j].sample_type) text = LIGHTBLUE;
                        else    text = RED;
                        textcolor(text);
                        /*
                                display ph, pco2, po2 if requested
                        */
                        if(strstr(px->previous_results[j].profile, "BG") ||
                                strstr(px->previous_results[j].profile, "Blood")){
                                gotoxy(3, row);
                                if(px->previous_results[j].ph > 0.0) {
                                        if((px->previous_results[j].ph < 7.20)
                                                || (px->previous_results[j].ph > 7.60))
                                                        textcolor(text + BLINK);
                                        cprintf("%-5.2f", px->previous_results[j].ph);
                                        textcolor(text + !BLINK);
                                }
                                else{
                                        if(px->previous_results[j].ph == -2) cprintf("NA");
                                        else cprintf("QNS");
                                }
                                gotoxy(10, row);
                                if(px->previous_results[j].pco2 > 0.0) {
                                        if((px->previous_results[j].pco2 < 20.0)
                                                        || (px->previous_results[j].pco2 > 70.0))
                                                                                textcolor(text + BLINK);
                                        cprintf("%-6.1f", px->previous_results[j].pco2);
                                        textcolor(text + !BLINK);
                                }
                                else{
                                        if(px->previous_results[j].pco2 == -2) cprintf("NA");
                                        else cprintf("QNS");
                                }
                                gotoxy(16, row);
                                if(px->previous_results[j].po2 > 0.0) {
                                        if(px->previous_results[j].po2 < 40.0)
                                                                textcolor(text + BLINK);
                                        cprintf("%-6.1f", px->previous_results[j].po2);
                                        textcolor(text + !BLINK);
                                }
                                else{
                                        if(px->previous_results[j].po2 == -2) cprintf("NA");
```

```
                        else cprintf("QNS");
                }
        }
        /*
                display lytes if requested
        */
        if(strstr(px->previous_results[j].profile, "LYTES")){
                gotoxy(23, row);
                if(px->previous_results[j].hct > 0.0) {
                        if((px->previous_results[j].hct < 18)
                                || (px->previous_results[j].hct > 60))
                                                textcolor(text + BLINK);
                        if(px->previous_results[j].hct < 20.0) cprintf("NOT");
                        else cprintf("%3.0f", px->previous_results[j].hct);
                        textcolor(text + !BLINK);
                }
                else{
                        if(px->previous_results[j].hct == -2) cprintf("NA");
                        else cprintf("QNS");
                }
                gotoxy(28, row);
                if(px->previous_results[j].na > 0.0) {
                        if((px->previous_results[j].na < 120)
                                || (px->previous_results[j].na > 160))
                                                        textcolor(text + BLINK);
                        cprintf("%5.1f", px->previous_results[j].na);
                        textcolor(text + !BLINK);
                }
                else{
                        if(px->previous_results[j].na == -2) cprintf("NA");
                        else cprintf("QNS");
                }
                gotoxy(35, row);
                if(px->previous_results[j].k > 0.0) {
                        if((px->previous_results[j].k < 2.5)
                                || (px->previous_results[j].k > 5.9))
                                                        textcolor(text + BLINK);
                        cprintf("%3.1f", px->previous_results[j].k);
                        textcolor(text + !BLINK);
                }
                else{
                        if(px->previous_results[j].k == -2) cprintf("NA");
                        else cprintf("QNS");
                }
                gotoxy(40, row);
                if(px->previous_results[j].cl > 0.0)
                        cprintf("%4.1f", px->previous_results[j].cl);
                else{
                        if(px->previous_results[j].cl == -2) cprintf("NA");
                        else cprintf("QNS");
                }
                gotoxy(46, row);
                if(px->previous_results[j].ca > 0.0) {
                        if((px->previous_results[j].ca < 0.5)
                                || (px->previous_results[j].ca > 1.50))
                                                        textcolor(text+BLINK);
                        cprintf("%4.2f", px->previous_results[j].ca);
                        textcolor(text + !BLINK);
                }
                else{
                        if(px->previous_results[j].ca == -2) cprintf("NA");
                        else cprintf("QNS");
                }
                gotoxy(52, row);
                if(px->previous_results[j].gluc > 0.0){
                        if((px->previous_results[j].gluc < 40)
                                || (px->previous_results[j].gluc > 500))
                                                        textcolor(text+BLINK);
                        if(px->previous_results[j].gluc > 499.9) cprintf(" NOT");
                        else cprintf("%4.0f", px->previous_results[j].gluc);
```

```
                                textcolor(text + !BLINK);
                        }
                        else{
                                if(px->previous_results[j].gluc = = -2) cprintf("NA");
                                else cprintf("QNS");
                        }
        /*
                        gotoxy(56, row);
                        if(px->previous_results[j].lac > 0.0){
                                cprintf("%4.0f", px->previous_results[j].lac);
                        }
                        else{
                                if(px->previous_results[j].lac = = -2) cprintf(" NA");
                                else cprintf(" QNS");
                        }
        */
                }
                /*
                        decode date and time and display
                */
                PXDateDecode(px->previous_results[j].done_date,&px->time.month,
                                &px->time.day,&px->time.year);
                gotoxy(64, row);
                cprintf("%s %d", month[px->time.month - 1],
                                                                                        px->time.day);
                gotoxy(72, row);
                px->previous_results[j].done_time[5] = '\0';
                cprintf("%s", px->previous_results[j].done_time);
        }
}
/*
        NAME:           display results - display results, checks for linearity
        INPUT:          patient results in px structure
        RETURN:         displays results and linear checks
*/
display_results(PX *px)
{
        int text = RED, x = 20, flg = 0;
        if(!strncmp(px->results.patient_name, "NOVA HCT", 8)) flg = 1;
        /*
                display patient information
        */
        display_patient_info(px);
        textcolor(text);
        /*
                arterial/venous
        */
        gotoxy(5, 10);
        if(!px->results.sample_type) {
                text = LIGHTBLUE;
                cprintf("VENOUS");
        }
        else cprintf("ARTERIAL");
        /*
                display ph,pco2,po2 if requested
        */
        if(strstr(px->results.profile, "BG") ||
                strstr(px->results.profile, "Blood")){
                gotoxy(x, 11);
                if(!flg){
                        textcolor(WHITE);
                        cprintf("pH:");
                        textcolor(text);
                        if(px->results.ph > 0.0){
                                if((px->results.ph < 6.50)
                                        || (px->results.ph > 8.00)){
                                                                                        textcolor(text + BLINK);
                                }
                                gotoxy(x + 6, 11);
                                cprintf("%5.2f", px->results.ph);
```

```
                                    textcolor(text + !BLINK);
                                    linear_check(x, 11, px->results.ph, 6.50, 8.00);
                            }
                            else{
                                    qns_uncal(x, 11, px->results.ph);
                            }
                    }
                    gotoxy(x, 12);
                    if(!flg){
                            textcolor(WHITE);
                            cprintf("pCo2:       mmHg");
                            textcolor(text);
                            if(px->results.pco2 > 0.0){
                                    if((px->results.pco2 < 3.00)
                                        || (px->results.pco2 > 200.00)){
                                                            textcolor(text + BLINK);
                                    }
                                    gotoxy(x + 5, 12);
                                    cprintf("%5.1f", px->results.pco2);
                                    textcolor(text + !BLINK);
                                    linear_check(x, 12, px->results.pco2, 3.00, 200.00);
                            }
                            else{
                                    qns_uncal(x, 12, px->results.pco2);
                            }
                    }
                    gotoxy(x, 13);
                    if(!flg){
                            textcolor(WHITE);
                            cprintf("pO2:        mmHg");
                            textcolor(text);
                            if(px->results.po2 > 0.0){
                                    if((px->results.po2 < 0.00)
                                        || (px->results.po2 > 800.00)){
                                                            textcolor(text + BLINK);
                                    }
                                    gotoxy(x + 5, 13);
                                    cprintf("%5.1f", px->results.po2);
                                    textcolor(text + !BLINK);
                                    linear_check(x, 13, px->results.po2, 0.00, 800.00);
                            }
                            else{
                                    qns_uncal(x, 13, px->results.po2);
                            }
                    }
            }
            /*
                    display lytes if requested
            */
            if(strstr(px->results.profile, "LYTES")){
                    gotoxy(x, 14);
                    if(!flg){
                            textcolor(WHITE);
                            cprintf("Hct:        %");
                            textcolor(text);
                            if(px->results.hct > 0.0){
                                    if((px->results.hct < 12.00)
                                        || (px->results.hct > 70.00)){
                                                            textcolor(text + BLINK);
                                    }
                                    gotoxy(x + 5, 14);
                                    cprintf("%3.0f", px->results.hct);
                                    textcolor(text + !BLINK);
                                    linear_check(x, 14, px->results.hct, 12.00, 70.00);
                                    if((px->results.hct < 20.00)){
                                            textcolor(LIGHTBLUE|BLINK);
                                            gotoxy(x + 20, 14);
                                            cprintf("NOT");
                                    }
                            }
```

```
                else{
                        qns_uncal(x, 14, px->results.hct);
                }
        }
        gotoxy(x, 15);
        if(!flg){
                textcolor(WHITE);
                cprintf("Na:         mmol/L");
                textcolor(text);
                if(px->results.na > 0.0){
                        if((px->results.na < 80.00)
                                || (px->results.na > 200.00)){          textcolor(text + BLINK);
                        }
                        gotoxy(x + 5, 15);
                        cprintf("%3.0f", px->results.na);
                        textcolor(text + !BLINK);
                        linear_check(x, 15, px->results.na, 80.00, 200.00);
                }
                else{
                        qns_uncal(x, 15, px->results.na);
                }
        }
        gotoxy(x, 16);
        if(!flg){
                textcolor(WHITE);
                cprintf("K:          mmol/L");
                textcolor(text);
                if(px->results.k > 0.0){
                        if((px->results.k < 1.00)
                                || (px->results.k > 20.00)){            textcolor(text + BLINK);
                        }
                        gotoxy(x + 6, 16);
                        cprintf("%4.1f", px->results.k);
                        textcolor(text + !BLINK);
                        linear_check(x, 16, px->results.k, 1.00, 20.00);
                }
                else{
                        qns_uncal(x, 16, px->results.k);
                }
        }
        gotoxy(x, 17);
        if(!flg){
                textcolor(WHITE);
                cprintf("Cl:         mmol/L");
                textcolor(text);
                if(px->results.cl > 0.0){
                        gotoxy(x + 5, 17);
                        cprintf("%3.0f", px->results.cl);
                        linear_check(x, 17, px->results.cl, 50.00, 200.00);
                }
                else{
                        qns_uncal(x, 17, px->results.cl);
                }
        }
        gotoxy(x, 18);
        if(!flg){
                textcolor(WHITE);
                cprintf("Ca:         mmol/L");
                textcolor(text);
                if(px->results.ca > 0.0){
                        if((px->results.ca < 0.10)
                                || (px->results.ca > 4.90)){            textcolor(text + BLINK);
                        }
                        gotoxy(x + 7, 18);
                        cprintf("%4.2f", px->results.ca);
```

```
                                    textcolor(text + !BLINK);
                                    linear_check(x, 18, px->results.ca, 0.10, 4.90);
                    }
                    else{
                                    qns_uncal(x, 18, px->results.ca);
                    }
            }
            gotoxy(x, 19);
            if(!flg){
                            textcolor(WHITE);
                            cprintf("Gluc:        mg/dl");
                            textcolor(text);
                            if(px->results.gluc > 0.0){
                                    if((px->results.gluc < 15.00)
                                            || (px->results.gluc > 500.00)){
                                                                            textcolor(text +
BLINK);
                                    }
                                    gotoxy(x + 5, 19);
                                    cprintf("%3.0f", px->results.gluc);
                                    textcolor(text + !BLINK);
                                    linear_check(x, 19, px->results.gluc, 15.00, 500.00);
                                    if((px->results.gluc > 499.9)){
                                            gotoxy(x + 20, 19);
                                            textcolor(LIGHTBLUE|BLINK);
                                            cprintf(" NOT");
                                    }
                            }
                            else{
                                    qns_uncal(x, 19, px->results.gluc);
                            }
            }
/*
            gotoxy(x, 20);
            if(!flg){
                            textcolor(WHITE);
                            cprintf("Lac:         mmol/L");
                            textcolor(text);
                            if(px->results.lac > 0.0){
                                    if((px->results.lac < 2.00)
                                            || (px->results.lac > 8.00)){
                                                                            textcolor(text +
BLINK);
                                    }
                                    gotoxy(x + 6, 20);
                                    cprintf("%4.1f", px->results.lac);
                                    textcolor(text + !BLINK);
                                    linear_check(x, 20, px->results.lac, 2.00, 8.00);
                            }
                            else{
                                    qns_uncal(x, 20, px->results.lac);
                            }
            }
*/
    }
}
/*
            NAME:       get_data - load previous results structure
            INPUT:      results from uva_raw.db and previous db's
            RETURN:     previous results structure in px loaded
*/
get_data(PX *px, RECORDHANDLE recHandle)
{
            long seq_num;
            PXGetAlpha(recHandle, 23, 7, px->previous_results[px->total_records].status);
            PXGetAlpha(recHandle, 25, 20, px->previous_results[px->total_records].profile);
            PXGetLong(recHandle, 5, &seq_num);
            if(!strcmp(px->previous_results[px->total_records].status, "DONE")){
                    if(seq_num != px->results.sn) return(1);
            }
```

```
   PXGetDate(recHandle, 20, &px->previous_results[px->total_records].done_date);
   PXGetDoub(recHandle, 8, &px->previous_results[px->total_records].ph);
   PXGetDoub(recHandle, 9, &px->previous_results[px->total_records].pco2);
   PXGetDoub(recHandle, 10, &px->previous_results[px->total_records].po2);
   PXGetDoub(recHandle, 11, &px->previous_results[px->total_records].hct);
   PXGetDoub(recHandle, 12, &px->previous_results[px->total_records].na);
   PXGetDoub(recHandle, 13, &px->previous_results[px->total_records].k);
   PXGetDoub(recHandle, 14, &px->previous_results[px->total_records].cl);
   PXGetDoub(recHandle, 15, &px->previous_results[px->total_records].ca);
   PXGetDoub(recHandle, 16, &px->previous_results[px->total_records].gluc);
/* PXGetDoub(recHandle, 27, &px->previous_results[px->total_records].lac);*/
   PXGetDoub(recHandle, 7, &px->previous_results[px->total_records].temp);
   PXGetShort(recHandle, 17, &px->previous_results[px->total_records].sample_type);
   PXGetAlpha(recHandle, 21, 9, px->previous_results[px->total_records].done_time);
   if(px->results.temp != 37.0)
           calculate_gas_correction(
                   &px->previous_results[px->total_records].ph,
                   &px->previous_results[px->total_records].pco2,
                   &px->previous_results[px->total_records].po2,
                   &px->previous_results[px->total_records].temp);
   return(0);
}
/*
   NAME:    get_results - get current patient results
   INPUT:   uva_raw.db records
   RETURN:  px structure results loaded with current results
*/
get_results(PX *px)
{
   unsigned rechdl;
   long recNumber;
   PXRecBufOpen(px->tblhdl, &rechdl);
   PXRecGoto(px->tblhdl, px->num_rec);
   PXRecGet(px->tblhdl, rechdl);
   PXGetAlpha(rechdl, 23, 10, px->results.status);
   PXGetLong(rechdl, 5, &px->results.sn);
   PXGetAlpha(rechdl, 1, 35, px->results.patient_name);
   PXGetAlpha(rechdl, 2, 10, px->results.ssn);
   PXGetAlpha(rechdl, 4, 10, px->results.access);
   PXGetDate(rechdl, 20, &px->results.done_date);
   PXGetAlpha(rechdl, 21, 9, px->results.done_time);
   PXGetShort(rechdl, 17, &px->results.sample_type);
   PXGetShort(rechdl, 18, &px->results.fio2);
   PXGetAlpha(rechdl, 19, 8, px->results.device_location);
   PXGetAlpha(rechdl, 24, 10, px->results.tech_number);
   PXGetAlpha(rechdl, 3, 8, px->results.unit);
   PXGetAlpha(rechdl, 25, 20, px->results.profile);
   PXGetAlpha(rechdl, 26, 40, px->results.instrument_errors);
   PXGetDoub(rechdl, 7, &px->results.temp);
   PXGetDoub(rechdl, 8, &px->results.ph);
   PXGetDoub(rechdl, 9, &px->results.pco2);
   PXGetDoub(rechdl, 10, &px->results.po2);
   PXGetDoub(rechdl, 11, &px->results.hct);
   PXGetDoub(rechdl, 12, &px->results.na);
   PXGetDoub(rechdl, 13, &px->results.k);
   PXGetDoub(rechdl, 14, &px->results.cl);
   PXGetDoub(rechdl, 15, &px->results.ca);
   PXGetDoub(rechdl, 16, &px->results.gluc);
/* PXGetDoub(rechdl, 27, &px->results.lac);*/
   /*
        correct for temperature
   */
   if(px->results.temp != 37.0)
           calculate_gas_correction(&px->results.ph, &px->results.pco2, &px->results.po2, &px->results.temp);
   if(!strcmp(px->results.status, "ACCEPT")
      || !strcmp(px->results.status, "FAIL")) return(1);
   PXRecBufClose(rechdl);
   return(0);
}
```

```
/*
        NAME:      get_timed_touch - gets touch screen touch or times out in specified
time
        INPUT:     operator entry
        RETURN:    touch response
*/
get_timed_touch(int touch_handle, char *entry)
{
        long start_time, now_time;
        time(&start_time);
        do{
                touch(touch_handle, "mode pad", entry);
                if (time(&now_time) > (start_time + 30)) return(0);
        } while (entry[0] != 'F');
        return(1);
}
/*
        NAME:      get_touch - gets the operators touch
        INPUT:     operator entry
        RETURN:    touch response
*/
get_touch(int touch_handle, char *entry, PX *px)
{
        int i;
        long start_time, now_time;
        time(&start_time);
        do{
                touch(touch_handle, "mode pad", entry);
                if (time(&now_time) > (start_time + 30)){
                        for(i = 950; i > 350; i -= 50) beep(i);
                        start_time = now_time;
                }
        } while (entry[0] != 'F');
        return(0);
}
/*
        NAME:      idle_screen - display system idle to save the screen
        INPUT:     none
        RETURN:    none
*/
idle_screen()
{
        int    random_row, random_column, random_color;
        clrscr();
        randomize();
        random_row = random(50) + 1;
        random_column = random(22) + 1;
        random_color = random(16);
        if(random_color < 9) {
                if(random_color < 7) random_color = random_color + 9;
                else {
                        random_color = random_color + 7;
                }
        }
        gotoxy(random_row, random_column);
        textcolor(random_color);
        cprintf("++ SATCEN SYSTEM IDLE ++");
}
/*
        NAME:      linear_check - instrument linearity check of results
        INPUT:     results
                   lo value
                   hi value
        RETURN:    displays L or H if outside given range
*/
linear_check(int x, int y, double result, double lo, double hi)
{
        gotoxy(x + 11, y);
        textcolor(LIGHTBLUE);
        if(result < lo) cprintf(" L");
```

```
        else if(result > hi) cprintf(" H");
}
/*
        NAME:       previous_reuslts_for_history_number - get previous results for
selected history number
        INPUT:      uva_raw.db and previous db
        RETURN:     previous results in px structure
*/
previous_results_for_history_number(PX *px)
{
        long      file_cnt;
        int       j, day = 0, exist;
        char      string_time[26], temp_ssn[10];
        time_t    bintime;
        unsigned  tblhdl, rechdl;
        px->total_records = 0;
        memset(px->previous_results, '\0', sizeof(px->previous_results));
        strcpy(px->date[0].previous_date, "h:\\db\\uva_raw");
        time(&bintime);
        /*
                make names of 5 previous days files
        */
        for (j = 1; j < 6; j++) {
                bintime -= (86400L);
                strcpy(string_time, ctime(&bintime));
                strcpy(px->date[j].previous_date, "h:\\db\\uv_");
                strncat(px->date[j].previous_date, &string_time[4],3);
                strncat(px->date[j].previous_date, &string_time[8],2);
        }
        do{
                PXTblExist(px->date[day].previous_date, &exist);
                if(exist) {
                        PXTblOpen(px->date[day].previous_date, &tblhdl, 0, 0);
                        PXRecBufOpen(tblhdl, &rechdl);
                        PXRecLast(tblhdl);
                        PXRecNum(tblhdl, &file_cnt);
                        while(file_cnt){
                                PXRecGet(tblhdl, rechdl);
                                PXGetAlpha(rechdl, 2, 10, temp_ssn);
                                if(!strcmp(px->results.ssn, temp_ssn)){
                                        if(!get_data(px, rechdl)) px->total_records++;
                                }
                                if(px->total_records >= 10) break;
                                file_cnt--;
                                PXRecPrev(tblhdl);
                        }
                        PXRecBufClose(rechdl);
                        PXTblClose(tblhdl);
                }
        } while((px->total_records < 9) && (++day < 6));
}
/*
        NAME:       print_lin_lim - print linear limit on results
        INPUT:      value to test
                    lo range
                    hi range
        RETURN:     prints L or H if result is out of range
*/
print_lin_lim(double value, double lo, double hi)
{
        char text = ' ';
        if(value < lo) text = 'L';
        else if(value > hi) text = 'H';
        fprintf(stdprn,"%c%c%c %c%c%c%c\n",
                0x0e, 0x1b, 0x34, text, 0x1b, 0x35, 0x14);
}
/*
        NAME:       print_results - print patient results
        INPUT:      px structure patient results
        RETURN:     prints current patient results
```

```
*/
print_results(PX *px)
{
        struct date date;
        struct time dtime;
        int month, day, year;
        float hco3, hb, be;
        if(px->results.flag) return(0);
        printer_status();
        gettime(&dtime);
        getdate(&date);
        fprintf(stdprn,"\n--------------------------------------\n");
        fprintf(stdprn,"University of Virginia Medical Center\n");
        fprintf(stdprn, "Charlottesville, Virginia\n");
        fprintf(stdprn, "Central Reporting Station\n\n");
        fprintf(stdprn, "Report Time: %02d:%02d:%02d  %02d/%02d/%02d\n\n",
                        dtime.ti_hour, dtime.ti_min, dtime.ti_sec,
                        date.da_mon, date.da_day, date.da_year);
        if(!strcmp(px->results.status,"REDONE")) {
                fprintf(stdprn,"     ***** REPEATED RESULTS *****\n\n");
        }
        fprintf(stdprn,"%15s %s\n", "PATIENT NAME:", px->results.patient_name);
        fprintf(stdprn,"%15s %s\n", "SSN:", px->results.ssn);
        fprintf(stdprn,"%15s %s\n", "UNIT:", px->results.unit);
        fprintf(stdprn,"%15s %ld\n", "SEQ NUMBER:", px->results.sn);
        PXDateDecode(px->results.done_date, &month, &day, &year);
        fprintf(stdprn,"%15s %d/%d/%d\n", "ANALYSIS DATE:", month, day, year);
        fprintf(stdprn,"%15s %s\n", "ANALYSIS TIME:", px->results.done_time);
        fprintf(stdprn,"%15s %s\n", "USER ID :", px->results.access);
        fprintf(stdprn,"%25s %s\n", "INSTRUMENT LOCATION:", px->results.device_location);
        fprintf(stdprn,"%25s %4.1f C\n", "PATIENT TEMPERATURE:", px->results.temp);
        if(px->results.sample_type){
                fprintf(stdprn,"%25s %s", "SAMPLE TYPE:", "arterial\n\n");
        }
        else {
                fprintf(stdprn,"%25s %s", "SAMPLE TYPE:", "venous\n\n");
        }
        fprintf(stdprn,"         %s\n\n", px->results.profile);
        if(px->results.ph > 0.0) {
                fprintf(stdprn,"%20s %6.2f", "pH:", px->results.ph);
                print_lin_lim(px->results.ph, 6.50, 8.00);
        }
        else {
                if(px->results.ph == -1.0)
                        fprintf(stdprn,"%20s %-6s\n", "pH:", "QNS");
                else fprintf(stdprn,"%20s %-6s\n", "pH:", "NA");
        }
        if(px->results.pco2 > 0.0) {
                fprintf(stdprn,"%20s %5.1f  mmHg", "pCO2:", px->results.pco2);
                print_lin_lim(px->results.pco2, 3.00, 200.00);
        }
        else {
                if(px->results.pco2 == -1.0)  fprintf(stdprn,"%20s %-6s mmHg\n",
                                "pCO2:", "QNS");
                        else fprintf(stdprn,"%20s %-6s mmHg\n", "pCO2:", "NA");
        }
        if(px->results.po2 > 0.0) {
                fprintf(stdprn,"%20s %5.1f  mmHg", "pO2:", px->results.po2);
                print_lin_lim(px->results.po2, 0.00, 800.00);
        }
        else {
                if(px->results.po2 == -1.0)  fprintf(stdprn,"%20s %-6s mmHg\n",
                                "pO2:", "QNS");
                        else fprintf(stdprn,"%20s %-6s mmHg\n", "pO2:", "NA");
        }
        if((px->results.ph <= 0.0) || (px->results.pco2 <= 0.0)){
                fprintf(stdprn,"%20s %s", "HCO3:", "NA\n");
                fprintf(stdprn,"%20s %s", "BE:", "NA\n");
        }
```

```
        else {
                hco3 = (0.031 * px->results.pco2) *
                                pow(10.0,(px->results.ph - 6.1));
                fprintf(stdprn,"%20s %5.1f  mmol/L\n", "HCO3:", hco3);
                if(px->results.hct > 0.0){
                        hb = px->results.hct/3.0;
                        if((px->results.ph > 0.0) && (px->results.pco2 > 0.0)){
                                be = ((1 - 0.0136 * hb) * (hco3 - 24.0) + (7.7 + 1.43 * hb)
                                                                                                                        * (px->results.ph - 7.4));
                                fprintf(stdprn,"%20s %5.1f  mmol/L\n", "BE:", be);
                        }
                }
                else{
                        fprintf(stdprn,"%20s %s", "BE:", "NA\n");
                }
        }
        if(px->results.fio2 > 0.0) fprintf(stdprn,"\n%20s %3d   \%\n\n", "FiO2:",
                                                                        px->results.fio2);
        else fprintf(stdprn, "%20s %-6s \%\n\n", "FiO2:", "NFG");
        if(px->results.na > 0.0){
                fprintf(stdprn,"%20s %-6.0f mmol/L", "Na:", px->results.na);
                print_lin_lim(px->results.na, 80.00, 200.00);
        }
        else if(px->results.na == -2.0) fprintf(stdprn,"%20s %-6s mmol/L\n",
                                                                        "Na:", "NA");
                else fprintf(stdprn,"%20s %-6s mmol/L\n", "Na:", "QNS");
        if(px->results.k > 0.0){
                fprintf(stdprn,"%20s %5.1f  mmol/L", "K:", px->results.k);
                print_lin_lim(px->results.k, 1.00, 20.00);
        }
        else if(px->results.k == -2.0) fprintf(stdprn,"%20s %-6s mmol/L\n",
                                                                        "K:", "NA");
                else fprintf(stdprn,"%20s %-6s mmol/L\n", "K:", "QNS");
        if(px->results.cl > 0.0){
                fprintf(stdprn,"%20s %3.0f    mmol/L", "Cl:", px->results.cl);
                print_lin_lim(px->results.cl, 50.00, 200.00);
        }
        else if(px->results.cl == -2.0) fprintf(stdprn,"%20s %-6s mmol/L\n",
                                                                        "Cl:", "NA");
                else fprintf(stdprn,"%20s %-6s mmol/L\n", "Cl:", "QNS");
        if(px->results.ca > 0.0){
                fprintf(stdprn,"%20s %6.2f mmol/L", "Ca++:", px->results.ca);
                print_lin_lim(px->results.ca, 0.10, 4.90);
        }
        else if(px->results.ca == -2.0) fprintf(stdprn,"%20s %-6s mmol/l\n",
                                                                        "Ca++:", "NA");
                else fprintf(stdprn,"%20s %-6s mmol/l\n", "Ca++:", "QNS");
        if(px->results.gluc > 0.0){
                fprintf(stdprn,"%20s %3.0f  mg/dl", "Glucose:", px->results.gluc);
                print_lin_lim(px->results.gluc, 15, 500);
        }
        else if(px->results.gluc == -2.0) fprintf(stdprn,"%20s %-6s mg/dl\n",
                                                                        "Glucose:", "NA");
                else fprintf(stdprn,"%20s %-6s mg/dl\n", "Glucose:", "QNS");
/*
        if(px->results.lac > 0.0){
                fprintf(stdprn,"%20s %4.1f  mmol/L", "Lactate:", px->results.lac);
                print_lin_lim(px->results.lac, 2.00, 8.00);
        }
        else if(px->results.lac == -2.0) fprintf(stdprn,"%20s %-6s mmol/L\n",
                                                                        "Lactate:", "NA");
                else fprintf(stdprn,"%20s %-6s mmol/L\n", "Lactate:", "QNS");
*/
        if(px->results.hct > 0.0){
                fprintf(stdprn,"%20s %3.0f    %", "hct:", px->results.hct);
                print_lin_lim(px->results.hct, 12.00, 70.00);
                fprintf(stdprn, "\n");
        }
        else if(px->results.hct == -2.0) fprintf(stdprn,"%20s %-6s %\n\n",
```

```
                                                        "hct:", "NA");
        else fprintf(stdprn,"%20s %-6s %\n\n", "hct:", "QNS");
fprintf(stdprn,"%20s %s\n\n", "INSTRUMENT ERROR:",
                                                        px->results.instrument_errors);
}
/*
        NAME:      printer_status - checks printer status for ready
        INPUT:     none
        RETURN:    none
*/
printer_status(void)
{
        int printer_status;
        textbackground(BLACK);
        textcolor(LIGHTRED + BLINK);
        printer_status = biosprint(2,' ',0);
        while (printer_status != 144) {
                printer_status = biosprint(2,' ',0);
                switch (printer_status) {
                        case 0:
                                gotoxy(24, 1);
                                cprintf(" Printer off line, press SEL/ALARM on printer.");
                                break;
                        case 40:
                                gotoxy(24, 1);
                                cprintf(" Printer out of paper, add paper.");
                                break;
                        case 200:
                                gotoxy(24, 1);
                                cprintf(" Printer is off, turn printer on.");
                                break;
                }
        }
        return(printer_status);
}
/*
        NAME:      process_control - tests record status for processing
        INPUT:     patient results in px structure
        RETURN:    0 if patient result is pending - status = DONE
                   1 if no patients available
*/
process_control(PX *px)
{
        int err, ret = 1;
        long rec;
        if(px->max_rec > px->num_rec) return(0);
        PXTblOpen("h:\\db\\uva_raw", &px->tblhdl, 0, 1);
        ret = status_search(px);
        PXTblClose(px->tblhdl);
        return(ret);
}
/*
        NAME:      pxtime - paradox time makes time a string HH:MM:SS
        INPUT:     px structure verify_time
        RETURN:    string time
*/
long pxtime(PX *px)
{
        struct time dtime;
        char temp[4];
        long total;
        gettime(&dtime);
        memset(px->results.verify_time, '\0', 10);
        itoa(dtime.ti_hour, temp, 10);
        if(dtime.ti_hour < 10){
                strcpy(px->results.verify_time, "0");
                strcat(px->results.verify_time, temp);
        }
        else{
                strcpy(px->results.verify_time, temp);
```

```
                }
                strcat(px->results.verify_time,":");
                itoa(dtime.ti_min, temp, 10);
                if(dtime.ti_min < 10){
                        strcat(px->results.verify_time, "0");
                }
                strcat(px->results.verify_time, temp);
                strcat(px->results.verify_time,":");
                itoa(dtime.ti_sec, temp, 10);
                if(dtime.ti_sec < 10){
                        strcat(px->results.verify_time, "0");
                }
                strcat(px->results.verify_time, temp);
                total = (dtime.ti_hour * 3600l) + (dtime.ti_min * 60) + dtime.ti_sec;
                return(total);
        }
        /*
                NAME:        qns_uncal - quantity not sufficient and uncalibrated displays ap-
        propriate string for error
                INPUT:       screen x & y location
                             value to test
                RETURN:      displayed value
        */
        qns_uncal(int x, int y, double value)
        {
                gotoxy(x + 7, y);
                textcolor(BLACK);
                if(value == -2) cprintf("NA");
                else     cprintf("QNS");
        }
        /*
                NAME:        results_screen - alerts operator to pending result
                                              gets previous results
                                              gets current results
                INPUT:       uva_raw.db and previous db's
                RETURN:      in px structure current and previous results
        */
        results_screen(PX *px, int touch_handle)
        {
                char    entry[0x10];
                int     i, j, sample_status = 0, exit;
                long    start_time, now_time;
                PXTblOpen("h:\\db\\uva_raw", &px->tblhdl, 0, 1);
                /*
                        get current results
                */
                if(get_results(px)){
                        PXTblClose(px->tblhdl);
                        return(-1);
                }
                /*
                        get previous results
                */
                previous_results_for_history_number(px);
                PXTblClose(px->tblhdl);
                /*
                        alert operator
                */
                for(j = 1000; j > 500; j -= 50) beep(j);
                /*
                        display location of results
                */
                textcolor(YELLOW);
                gotoxy(10,8);
                cprintf("These results are from:");
                gotoxy(18,12);
                cprintf("%s",px->results.device_location);
                gotoxy(9,23);
                cprintf("touch screen for results");
                touch(touch_handle,"group all off",entry);
```

```
1    touch(touch_handle,"group 0 on",entry);
     get_touch(touch_handle, entry, px);
2    beep(700);
     puts ("\377\377satcen/");
3    touch(touch_handle,"group all off",entry);
     touch(touch_handle,"group 1 on",entry);
4    /*
             display patinet results
5    */
     display_results(px);
6    /*
             check for errors and delta checks
7    */
     if(!strstr(px->results.profile, "Blood")) display_delta_check(px);
8    display_instrument_errors(px);
     /*
9            print results
     */
10   print_results(px);
     /*
11           process operator touch input
     */
12   do {
             get_touch(touch_handle, entry, px);
13           switch(entry[2]) {
                     case 'F':
14                           /*
                                     failed sample
15                           */
                             beep(500); beep(400);
16                           sample_status = 1;
                             break;
17                   case 'A':
                             /*
18                                   accept
                             */
19                           beep(600); beep(800);
                             sample_status = 2;
20                           break;
                     case 'P':
21                           /*
                                     previous results
22                           */
                             beep(700);
23                           exit = 1;
                             puts ("\377\377previous/");
24                           display_previous_results(px);
                             touch(touch_handle,"group all off",entry);
25                           touch(touch_handle,"group 3 on",entry);
                             do {
26                                   time(&start_time);
                                     do {
27                                           touch(touch_handle, "mode pad", entry);
                                             if(time(&now_time) > (start_time + 30)) {
28                                                   exit = 0;
                                                     entry[0] = 'F';
29                                           }
                                     } while(entry[0] != 'F');
30                                   switch(entry[2]) {
                                             case 'C':
31                                                   /*
                                                             current results
32                                                   */
                                                     beep(700);
33                                                   if(touch_handle)
     touch(touch_handle,"group 3 off",entry);
34                                                           exit = 0;
                                             }
35                           } while(exit);
                             puts("\377\377satcen/");
```

```
                    touch(touch_handle,"group 1 on",entry);
                    /*
                            redisplay current results,errors, delta checks
                    */
                    display_results(px);
                    if(!strstr(px->results.profile, "Blood"))
                                                    display_delta_check(px);
                    display_instrument_errors(px);
                    break;
            }
    } while (!sample_status);
    return(sample_status);
}
/*
    NAME:       search - database for desired status
    INPUT:      selected status
    RETURN:     0 if selected status found and result record number
                1 if not
*/
search(char *status, unsigned tblhdl, long *rec_cnt)
{
    unsigned    rechdl;
    int ret = 1;
    PXRecBufOpen(tblhdl, &rechdl);
    PXPutAlpha(rechdl, 23, status);
    if(PXSrchFld(tblhdl, rechdl, 23, SEARCHFIRST) == PXSUCCESS){
            PXRecNum(tblhdl, rec_cnt);
            ret = 0;
    }
    PXRecBufClose(rechdl);
    return(ret);
}
/*
    NAME:       status_search - search status and get max number of results records
    INPUT:      uva_raw.db records
    RETURN:     0 if DONE found
                1 if not
*/
status_search(PX *px)
{
    PXTblNRecs(px->tblhdl, &px->max_rec);
    if(!search("DONE", px->tblhdl, &px->num_rec)) return(0);
    return(1);
}
/*
    NAME:       tech_input - get technologist touch entry
    INPUT:      touch entry
    RETURN:     px structure access and verify code
*/
tech_input(int mode, int touch_handle, PX *px)
{
    char entry[0x10];
    int count = 0, row = 3, col = 65, length = 6;
    do {
            if(!get_timed_touch(touch_handle, entry)) return(0);
            if(strncmp(&entry[2], "NONE", 4)){
                    switch(entry[2]) {
                        case '@':
                                /*
                                        clear entry
                                */
                                beep(850);
                                textbackground(BLACK);
                                gotoxy(64, 3);
                                cprintf("            ");
                                col = col - count;
                                count = 0;
                                px->results.tech_number[0] = '\0';
                                break;
                        case '!':
```

```
                                        /*
1                                               enter
2                                        */
                                        beep(600);
3                                       beep(800);
                                        break;
4                               default:
                                        /*
5                                               char entry
                                        */
6                                       beep(700);
                                        if(count < length){
7                                               gotoxy(col++,row);
                                                px->results.tech_number[count++] = entry[2];
8                                               if(mode){
                                                        cprintf ("%c", px-
9     >results.tech_number[count-1]);
                                                }
10                                              else{
                                                        cprintf("*");
11                                              }
                                        }
12                                      else    beep(550);
                                        break;
13                              }
                        }
14              } while (entry[2] != '!');
                if(count) px->results.tech_number[count] = '\0';
15              return(0);
        }
16      /*
                NAME:           time_change - tests time of day for database fabrication and clears
17      raw db of processed files
                INPUT:  system time
18              RETURN:         new day file if past selected time
        */
19      time_change(PX *px)
        {
20              static int time_flag = 0;
                struct tm *tnow;
21              int Exist;
                time_t bintime;
22              time(&bintime);
                tnow = localtime(&bintime);
23              if(7 > tnow->tm_hour){
                        if(time_flag) time_flag = 0;
24              }
                else if(!time_flag){
25                      time_flag = 1;
                        yesterday(px);
26                      PXTblExist(px->time.current_date, &Exist);
                        if(!Exist){
27                              clrscr();
                                if(!copy_current_date_table(px)){
28                                      delete_records(px);
                                }
29              }
                }
30      }
        /*
31              NAME:           touch - touch screen entry routine
                INPUT:          str command for touch driver
32              RETURN:         inbuf - resultant touch entry
        */
33      touch(int touch_handle, char *str, char *inbuf)
        {
34              char string[0x20], term[2] = {0x0d, NULL};
                char *pt;
35              pt = inbuf;
                if(bioskey(1)){
```

```
         strset(inbuf, 'F');
         inbuf[2] = bioskey(0);
         if(inbuf[2] > 0x5a) inbuf[2] &= 0xdf;
         if(inbuf[2] == 0x1b){
                 PXExit();
                 cursor_on_off(1);
                 textcolor(LIGHTGRAY);
                 textbackground(BLACK);
                 clrscr();
                 exit(0);
         }
         return(1);
 }
 else if(!touch_handle){
         strcpy(inbuf, "    NONE");
         return(0);
 }
 strcpy(string, str);
 strcat(string, term);
 if(write(touch_handle, string, strlen(string)) == -1) {
         perror("write|");
         close(touch_handle);
         exit(0);
 }
 if(read(touch_handle, inbuf, 0x20) == -1) {
         perror("read|");
         close(touch_handle);
         exit(0);
 }
 while(*pt++ != 0x0d);
 *pt = NULL;
 if(inbuf[0] == 'E') {
         printf("ERROR - %s\n", inbuf);
 }
}
/*
    NAME:       verifying_tech_code - allows operator to enter access and verify
code for checking
    INPUT:      px structure
    RETURN:  0 if OK
                   1 if error
*/
verifying_tech_code(int touch_handle, PX *px)
{
    char entry[10], temp_tech[10], auth[5];
    int i = 0;
    TABLEHANDLE    tblhdl;
    RECORDHANDLE   rechdl;
    /*
        pop screen for tech input
    */
    textbackground(BLACK);
    clrscr();
    puts("\377\377keys/");
    puts("\377\377techinfo/");
    puts("\377\377alphakey/");
    touch(touch_handle,"group all off", entry);
    touch(touch_handle,"group 5 on", entry);
    touch(touch_handle,"group 8 on", entry);
    textbackground(BLACK);
    textcolor(WHITE);
    /*
        open uva_acc.db for access check
    */
    PXTblOpen("h:\\db\\uva_acc", &tblhdl, 0, 1);
    PXRecBufOpen(tblhdl, &rechdl);
    do {
        gotoxy(13, 4);
        textcolor(YELLOW);
        cprintf("Enter your Tech ACCESS Code");
```

```
1   strset(px->results.tech_number, '\0');
    /*
2           operator entry of tech access code
    */
3   tech_input(1, touch_handle, px);
    if(!strlen(px->results.tech_number)){
4           PXRecBufClose(rechdl);
            PXTblClose(tblhdl);
5           px->results.flag = 1;
            return(1);
6   }
    strcpy(temp_tech, px->results.tech_number);
7   gotoxy(10, 4);
    textcolor(YELLOW|BLINK);
8   cprintf("Enter your Tech VERIFICATION Code");
    puts("\377\377 keys/");
9   textcolor(WHITE);
    strset(px->results.tech_number, '\0');
10  /*
            operator entry of tech verify code
11  */
    tech_input(0, touch_handle, px);
12  if(!strlen(px->results.tech_number)){
            PXRecBufClose(rechdl);
13          PXTblClose(tblhdl);
            px->results.flag = 1;
14          return(1);
    }
15  strcpy(px->results.verify, px->results.tech_number);
    strcpy(px->results.tech_number, temp_tech);
16  /*
            search for access code match
17  */
    PXPutAlpha(rechdl, 1, px->results.tech_number);
18  PXSrchFld(tblhdl, rechdl, 1, SEARCHFIRST);
    PXRecGet(tblhdl, rechdl);
19  PXGetAlpha(rechdl, 4, 5, auth);
    /*
20          if authority = 0, user cannot verify results at SATCEN
    */
21  if(auth[0] == '0'){
            px->results.flag = 1;
22          clrscr();
            sound(1500);
23          gotoxy(20,10);
            cprintf("Not a valid authority code - reenter");
24          sleep(1);
            nosound();
25          sleep(1);
            PXRecBufClose(rechdl);
26          PXTblClose(tblhdl);
            return(1);
27  }
    PXGetAlpha(rechdl, 2, 10, temp_tech);
28  if(strcmp(px->results.verify, temp_tech)){
            gotoxy(8, 4);
29          textcolor(LIGHTRED|BLINK);
            cprintf("  ACCESS/VERIFY CODES DO NOT MATCH   ");
30          beep(1000);
            sleep(2);
31          PXRecBufClose(rechdl);
            PXTblClose(tblhdl);
32          px->results.flag = 1;
            return(1);
33  }
    } while(!(strlen(px->results.tech_number)));
34  px->results.flag = 0;
    PXRecBufClose(rechdl);
35  PXTblClose(tblhdl);
    return(0);
```

```
1   }
    /*
2           NAME:       yesterday - forms yesterday's date as a file name
            INPUT:      px structure
3           RETURN:     px datetime loaded
    */
4   yesterday(PX *px)
    {
5           char string_time[40];
            time_t tm;
6           time(&tm);
            tm = tm - 86400l;
7           strcpy(string_time, ctime(&tm));
            strcpy(px->time.current_date, "h:\\db\\uv_");
8           strncat(px->time.current_date, &string_time[4], 3);
            strncat(px->time.current_date, &string_time[8], 2);
9   }
```

FIGS. 6–12 illustrate, in flow diagrams, the program for the Analysis Station as described in the following code.

```
/*
        mas_sa.c
        version 1.0
        9/94
*/
#include <asynch_1.h>
#include <bios.h>
#include <conio.h>
#include <dos.h>
#include <fcntl.h>
#include <io.h>
#include <math.h>
#include <mem.h>
#include <pxengine.h>
#include <stdio.h>
#include <stdlib.h>
#include <string.h>
#include <sys\types.h>
#include <sys\stat.h>
#include <time.h>
/*
        Results structure
        bp = barometric pressure in mmhg
        ph = [hydrogen]
        pco2 = partial pressure of carbon dioxide in sample
        po2 = partial pressure of oxygen in sample
        hct = sample hematocrit
        na = [Sodium]
        k = [Potassium]
        cl = [Cholride]
        ca = [Calcium]
        gluc = [Glucose]
        lac = [Lactate]
*/
typedef     struct{
        double bp, ph, pco2, po2, hct, na, k, cl, ca, gluc, lac;
        long sn;
        char ssn[10];
} RESULTS_DATA;
/*
        Demographics structure
        nme = patient name
        loc = patient location within hospital
        ssn = Social Security Number
*/
typedef struct {
        char nme[20], loc[10], ssn[10];
} DEMOGRAPHICS;
/*
```

```
 1          Data structure
            all doubles as listed above in results
 2          sn = sequence number of sample - internally generated
            time = time of sample
 3          date = date sample was run
            month
 4          day         self explanatory
            year
 5          abort_flag = if sample sequence was aborted
            unit = location of patient within hospital
 6          pat = patient name
            access = user access code to enter system
 7          ssn = Social Security Number
            string_time = time as an HH:MM:SS of sample completion
 8          devloc = device location within hospital
            status = status of sample (DONE, ACCEPT, FAIL)
 9          errors = instrument errors - see nova_err.db for list
            profile = profile of tests (Blood Gas, Bg + Lytes + Gluc, Lytes + Gluc)
10          fio2 = fraction of inhaled oxygen
            type = sample type (arterial, venous)
11          test_select =
      */
12          typedef struct {
                    double temp, bp, ph, pco2, po2, hct, na, k, cl, ca, gluc, lac;
13                  long sn, time, date;
                    int     month, day, year, abort_flag;
14                  char unit[10], pat[20], access[10], ssn[10];
                    char string_time[10], devloc[10], status[10], errors[40];
15                  char profile[20];
                    short fio2, type, test_select;
16          } DATA;

17    /*
            Calculated structure
18          ph = hydrogen ion concentration of sample pH
            pco2 = partial pressure of carbon dioxide in sample
19          po2 = partial pressure of oxygen in sample
            hct = sample hematocrit
20          na = [Sodium]
            k = [Potassium]
21          cl = [Cholride]
            ca = [Calcium]
22          gluc = [Glucose]
            lac = [Lactate]
23          be_ecf = [base excess extra cellular fluid]
            be_b = [base excess blood]
24          hco3 = [bicarbonate]
            tco2 = [total carbon dioxide]
25          o2sat = [oxygen saturation]
            o2ct = [oxygen content]
26          nca = normalized [Calcium]
            hb = hemoglobin
27    */
            typedef struct {
28                  double ph, pco2, po2, hct, na, k, cl, ca, gluc, lac;
                    double be_ecf, be_b, hco3, tco2, o2sat, o2ct, nca, hb;
29          } CALCULATED;
      /*
30          Pic data structure
            access = user access code to system
31          verify = user verify code to system
            name = user name
32          auth = authority of system useage
            ssn = Social security Number
33          unit = last unit requested by user
            phone = telephone number of user
34          time = time successful usage of access code completed
            tblhdl = Paradox table handle
35    */
            typedef struct {
```

```
 1              char access[10], verify[10], name[20], auth[5], ssn[10];
                char unit[10], phone[15];
 2              long time;
                unsigned tblhdl;
 3          } PIC_DATA;
    /* Units structure
 4          location = name of unit
    */
 5          typedef     struct{
                char location[10];
 6          } UNITS;
    /*
 7          Ttime structure
    */
 8          typedef struct{
                struct time dtime;
 9              char        time[20];
            }TTIME;
10  void interrupt irq_func(void);
    void interrupt (*old_handle)();
11  long pxtime(TTIME *);
    /* redefine stack length for Paradox */
12  extern unsigned _stklen = 0x3000;
    /* screen buffer for NOVA analyzer */
13  unsigned char scrn_buf[0x344];
    TTIME       ttime;
14  /* colors valid for system idle screen */
    int sel_color[] = {LIGHTRED, LIGHTBLUE, LIGHTGREEN};
15  /* panels of anlaytes used by NOVA 9 */
    char *test_sel[] = {"Blood gas", "BG + Elec/Glu/Lac", "Elec/Glu/Lac"};
16  /* screen headers for data retreival from NOVA analyzer */
    char *scrn_header[] = {"Acc. ", "I.D.", "BP", "pH", "PCO",
17                          "PO", "Hct","Na", "K", "Cl", "Ca", "Glu", NULL};
    main(){
18          int function_choice, not_ready_flag, handle, i, loop, coding;
            int count, send_Nova_MIS_number;
19          char scrn_id[10], inbuf[32];
            PIC_DATA pic_data;
20          RESULTS_DATA results;
            DATA data;
21          CALCULATED cal;
            DEMOGRAPHICS pat_rec[40];
22          UNITS units[40];
            clrscr();
23          gotoxy(1,1);
            cursor_on_off(0);
24          memset(scrn_buf, '\0', 1024);
            handle = open_touch();
25          tch_scale(handle, "scale 80 24");
            touch(handle, "padload sa", inbuf);
26      /*
            - initialize nova analyzer to ready/not ready screen
27      */
        setmem(scrn_buf, 0x344, 32);
28      bioscom(0, 0xe3, 0);
        old_handle = getvect(0x0c);
29      rec_irq_enable();
        PXNetInit("h:\\db\\", NETSHARE, "MAS_SA");
30      PXTblOpen("h:\\db\\count", &tblhdl, 0, 1);
        PXRecBufOpen(tblhdl, &rechdl);
31      PXPutAlpha(rechdl, 1, "TCVPO");
        if(!PXSrchFld(tblhdl, rechdl, 1, SEARCHFIRST)){
32          PXRecGet(tblhdl, rechdl);
            PXGetLong(rechdl, 2, &count);
33      }
        else{
34          PXExit();
            clrscr();
35          exit(0);
        }
```

```
PXRecBufClose(rechdl);
PXTblClose(tblhdl);
printf("\tNOVA I/O\n");
for(i = 0; i < 4; i++) {
        delay(100);
        outportb(0x3f8, 0x7f);
}
outportb(0x3f8, 'H');
delay(100);
outportb(0x3f8, 0x7f);
/*
        - turn cursor off
        - set function choice to beginning of operation
*/
cursor_on_off(0);
function_choice = 0;
/*
        main body do loop that controls operation
*/
do {
        switch(function_choice) {
                case -1:
                        /*
                                - disable nova analyzer irq
                                - return original irq vectors
                                - clear keyboard buffer
                                - disable paradox network
                                - turn cursor on
                                - exit program
                        */
                        rec_irq_disable();
                        disable();
                        setvect(0x0c, old_handle);
                        enable();
                        clrscr();
                        while(bioskey(1)) bioskey(0);
                        PXExit();
                        cursor_on_off(1);
                        exit(0);
                case 0:
                        /*
                                - set data structure to null
                                - set results structure to null
                                - clears not ready flag for analyzer
                                - user access/verify code entry function (logscrn)
                        */
                        loop = 0;
                        memset(&data, '\0', sizeof(DATA));
                        memset(&results, '\0', sizeof(RESULTS_DATA));
                        not_ready_flag = 0;
                        function_choice = logscrn(handle, &data, &pic_data);
                        /*
                                - 12 - timeout of screen
                        */
                        if(function_choice == 12) break;
                        /*
                                - 9 - select review results, maintanance, exit, analyze sample
                        */
                        if(function_choice != 9){
                                function_choice = analyze_view(handle, &pic_data);
                        }
                        break;
                case 1:
                        /*
                                - check instrument for ready/ not ready status
                        */
                        if(!check_instrument()){
                                if(not_ready_flag) function_choice = 0;
                                else     function_choice = 2;
```

```
}
else {
        /*
                instrument evaluation - ready for analysis
        */
                function_choice = check_instrument_error(handle);
                not_ready_flag = 1;
        }
        break;
case 2:
        /*
                pic data unit and access moved to data structure for use
                in wrole
        */
        strcpy(data.unit, pic_data.unit);
        strcpy(data.access, pic_data.access);
        /*
                wrole retrieves list of valid units
        */
        function_choice =
                wrole(handle, &data, units);
        break;
case 3:
        /*
                role retrieves list of valid patients for selected unit
        */
        function_choice =
                role(handle, &data, pat_rec);
        break;
case 4:
        /*
                find history number searchs uva_pats database for
                selected history number
        */
        function_choice =
                find_history_number(handle, &data);
        break;
case 5:
        /*
                nop - proceed to 6
        */
        function_choice = 6;
        break;
case 6:
        /*
                display sample parameters - displays user selectable
                sample parameters
                - test select defaults to all tests
                display confirm parameters - displays user selected
                parameters for confirmation
        */
        coding = 0;
        data.test_select = 1;
        display_sample_parameters(handle, &data, count);
        if((function_choice = delta_sample_parameters(handle,
                &coding, &data, count)) != 0) break;
        function_choice = display_confirm_parameters(handle,
                coding, &data, &count);
        break;
case 7:
        /*
                - check analyzer for ready/not ready
                - delta sequence number increments sequence number in
                uva_cnt.db for selected unit
                - initialize instrument for sample operation
        */
        if(!check_instrument()){
                delta_seq_num(&count);
                function_choice =
```

```
                initialize_instrument(&send_Nova_MIS_number,
                                                                            &pic_data);
                        }
                        /*
                                retrieve instrument errors
                        */
                        else function_choice = check_instrument_error(handle);
                        break;

case 8:
                        /*
                                display standalone header
                        */
                        if(!loop){
                                loop = 1;
                                clrscr();
                                sa_hdr(YELLOW, "Sample Analysis Sequence");
                        }
                        /*
                                wait for analyzer to complete operation - retrieve results
                        */
                        function_choice =
check_status_of_instrument(&send_Nova_MIS_number,
                                        &results, &data, scrn_id, count);
                        break;
                    case 9:
                        /*
                                manual operation of nova analyzer
                        */
                        nova_ctl(handle);
                        function_choice = 0;
                        break;
                    case 10:
                        /*
                                retrieve previous results for selected patients
                        */
                        strcpy(data.unit, pic_data.unit);
                        strcpy(data.access, pic_data.access);
                        function_choice =
                                view_results(handle, pat_rec, &data, units);
                        break;
                    case 11:
                        /*
                                display results
                        */
                        results_screen(handle, &data, &cal, count);
                        function_choice = 0;
                        break;
                    case 12:
                        /*
                                system idle
                        */
                        function_choice = idle_screen(handle);
                        break;
                    }
            } while(1);
        }
        /*
            NAME:       access search - searches uva_acc.db for valid user access/verify code
            INPUT:      pic_data structure access & verify
            RETURNS:    0 if access/verify match in databse
                        1 if no match
                        authority code for system operation
            DELTA:      time of last usage of selected access/verify code
        */
        access_search(PIC_DATA *pic_data)
        {
```

```
1        TABLEHANDLE    tblhdl;
         RECORDHANDLE   rechdl;
2        char tmp_ver[10];
         PXTblOpen("h:\\db\\uva_acc", &tblhdl, 0, 0);
3        PXRecBufOpen(tblhdl, &rechdl);
         if(search_access(tblhdl, rechdl, pic_data) != PXSUCCESS){
4                PXRecBufClose(rechdl);
                 PXTblClose(tblhdl);
5                return(1);
         }
6        PXRecGet(tblhdl, rechdl);
         PXGetAlpha(rechdl, 2, 10, tmp_ver);
7        if(strcmp(pic_data->verify, tmp_ver)){
                 PXRecBufClose(rechdl);
8                PXTblClose(tblhdl);
                 return(1);
9        }
         time(&pic_data->time);
10       PXPutLong(rechdl, 8, pic_data->time);
         get_unit_auth(rechdl, pic_data);
11       get_search_data(rechdl, pic_data);
         PXRecBufClose(rechdl);
12       return(0);
         }
13       /*
         NAME:         analyze_view - displays a selection of review results, maintenance,
14       exit, analyze
         INPUT:        user touch or keypad select
15                     authority code used for manipulating screen display
         RETURN:       next operation of system
16       */
         analyze_view(unsigned handle, PIC_DATA *pic_data)
17       {
                 char entry[0x10];
18               sa_scrn(YELLOW, "Review Results & Analyze Sample", LIGHTRED, "Select opera-
         tion desired");
19               puts("\377\377re_ana/");
                 puts("\377\377esc/");
20               touch(handle,"group all off",entry);
                 touch(handle,"group 14 on",entry);
21               touch(handle,"group 15 on",entry);
         gotoxy(1,1);
22               switch(pic_data->auth[0])
                         {
23                       case '3':
                                 touch(handle, "group 17 on", entry);
24                               puts("\377\377exit/");
                         case '2':
25                       case '1':
                                 touch(handle, "group 16 on", entry);
26                               puts("\377\377main/");
                                 break;
27                       }
                 if(!touch_choice('F', entry, handle)){
28                       switch(entry[2]) {
                                 case 'A':
29                                       beep(850);
                                         return(1);
30                               case 'M':
                                         beep(400);
31                                       return(9);
                                 case 'R':
32                                       beep(800);
                                         return(10);
33                               case 'S':
                                         beep(440);
34                                       return(-1);
                                 case 'X':
35                                       beep(800);
                                 }
```

```
         }
         return(0);
    }
    /*
         NAME:      beep - sounds given frequency to user
         INPUT:     none
         RETURN:    none
    */
    beep(int freq)
    {
         sound(freq);
         delay(75);
         nosound();
    }
    /*
         NAME:      calculated_results - calculates the desired values from the measured
    analytes
         INPUT:     data structure with measured analyte
         RETURN:    calculated structure
    */
    calculated_results(DATA *data, CALCULATED *cal)
    {
         double N;
         cal->ph = data->ph;
         cal->pco2 = data->pco2;
         cal->po2 = data->po2;
         cal->hct = data->hct;
         cal->na = data->na;
         cal->k = data->k;
         cal->cl = data->cl;
         cal->ca = data->ca;
         cal->gluc = data->gluc;
         cal->lac = data->lac;
         /*
              bicarbonate
         */
         cal->hco3 = (0.031 * cal->pco2) * pow(10.0, (cal->ph - 6.1));
         /*
              hemoglobin
         */
         if(strcmp(data->profile, "Elec/Glu/Lac"))cal->hb = cal->hct/3.0;
         else cal->hb = 15.0;
         /*
              base excess blood
         */
         cal->be_b = ((1 - 0.0136 * cal->hb) * (cal->hco3 - 24.0) +
                     (7.7 + 1.43 * cal->hb) * (cal->ph - 7.4));
         N = cal->po2 * pow(10, (0.48 * (cal->ph - 7.4) - 0.0013 * cal->be_b));
         /*
              oxygen saturation
         */
         cal->o2sat = ((pow(N, 4) - 15.0 * pow(N, 3) + 2045.0 * pow(N, 2) + 2000.0 * N)/
                      (pow(N, 4) - 15.0 * pow(N, 3) + 2400.0 * pow(N, 2) -
                       3.1e4 * N + (2.4e6))) * 100;
         /*
              base excess extracellular fluid
         */
         cal->be_ecf = cal->hco3 - 25.0 + 16.2 * (cal->ph - 7.40);
         /*
              oxygen content
         */
         cal->o2ct = 1.39 * cal->hb * (cal->o2sat/100.0) + 0.003 * cal->po2;
         /*
              total carbon dioxide
         */
         cal->tco2 = cal->hco3 + (0.031 * cal->pco2);
         /*
              normalized calcium
         */
         cal->nca = cal->ca * pow(10.0,(-0.178 * (7.4 - cal->ph)));
```

```
    }
/*
        NAME:       calcpd - calculator pad used to change numerical values of user selec-
table sample parameters
        INPUT:      user interaction with touch driver
        RETURN:     returns user selected value to temp, fio2
*/
calcpd(int row, int handle, DATA *data)
{
        const length = 3;
        char  fld[5], entry[0x10];
        int Fio, count = 0, col = 29, display_window = 64;
        float temp;
        /*
                put up screens and enable touch targets
        */
        puts ("\377\377keys/");
        puts ("\377\377esc/");
        touch(handle, "group all off", entry);
        touch(handle, "group 1 on", entry);
        touch(handle, "group 15 on", entry);
        gotoxy(col, row);
        /*
                clear default values displayed
        */
        if(row == 15) cprintf("___");
        else    cprintf("__._");
        strcpy(fld," ");
        /*
                get user touch
        */
        do {
                if(touch_choice('F', entry, handle))            return(12);
                textcolor(WHITE);
OUT_OF_RANGE:
                switch(entry[2]) {
                        case '@':
                                /*
                                        clear user input
                                */
                                beep(850);
                                count = 0;
                                col = 29;
                                strcpy(fld," ");
                                gotoxy(col,row);
                                if(row == 15) cprintf ("___");
                                else cprintf("__._");
                                display_window = 64;
                                gotoxy(display_window, 3);
                                cprintf("         ");
                                break;
                        case '!':
                                /*
                                        enter user number
                                */
                                beep(800);
                                if(row == 15){
                                        Fio = atoi(fld);
                                        if((Fio < 20) || (Fio > 100)){
                                                entry[2] = '@';
                                                goto OUT_OF_RANGE;
                                        }
                                }
                                else {
                                        /*
                                                test user input for valid temp selected
                                        */
                                        temp = atof(fld);
                                        if(temp < 25.0 || temp > 45.0){
                                                entry[2] = '@';
```

```
                                            goto OUT_OF_RANGE;
                                    }
                            display_window = 64;
                            gotoxy(display_window, 3);
                            cprintf("              ");
                            break;
                    case 'X':
                            /*
                                    escape
                            */
                            beep(950);
                            return(6);
                    default:
                            /*
                                    display user selected input
                            */
                            beep(700);
                            if(count < length) {
                                    if((col == 31) & (row == 13)) {
                                            col++;
                                    }
                                    gotoxy (col++,row);
                                    cprintf ("%c", entry[2]);
                                    if((display_window == 66) & (row == 13)) {
                                            count++;
                                            gotoxy(display_window++, 3);
                                            cprintf(".");
                                            fld[2] = 0x2e;
                                            gotoxy(display_window++, 3);
                                            cprintf("%c",fld[count++] = entry[2]);
                                    }
                                    else {
                                            gotoxy(display_window++, 3);
                                            cprintf("%c",fld[count++] = entry[2]);
                                    }
                            }
                            else    beep(600);
                            break;
                    }
            } while(entry[2] != '!');
            if(count) {
                    fld[count] = '\0';
            }
            /*
                    temperature
            */
            if(row == 13) {
                    if(!strcmp(fld,"     ")) {
                            data->temp = 37.0;
                            gotoxy(29,row);
                            cprintf("37.0");
                    }
                    else {
                            data->temp = atof(fld);
                    }
            }
            /*
                    fio2
            */
            if(row == 15) {
                    if(!strcmp(fld,"     ")) {
                            data->fio2 = -1;
                            gotoxy(29,row);
                            cprintf("NFG ");
                    }
                    else data->fio2 = atoi(fld);
            }
            return(0);
    }
```

```c
/*
        NAME:       check_cal_status - checks instrument calibration status
        INPUT:      screen buffer
        RETURN:     seconds to completion of calibration
*/
check_cal_status()
{
        char *temp;
        if(!strstr(scrn_buf, "Gas Cal in Progress") == NULL ||
                !strstr(scrn_buf, "Auto-Cal in Progress") == NULL ||
                !strstr(scrn_buf, "Elec/Glu/Lac Cal in Progress") == NULL ||
                !strstr(scrn_buf, "Ph + Hct Cal in Progress") == NULL ||
                !strstr(scrn_buf, "Full Cal in Progress") == NULL){
                        if((temp = strstr(scrn_buf, "Seconds to Completion")) != NULL){
                                temp -= 5;
                                temp[4] = NULL;
                                return(atoi(temp));
                        }
        }
        return(0);
}
/*
        NAME:       check_instrument - checks analyzer for ready or system idle screen
        INPUT:      screen buffer
        RETURN:     0 if ready for operation
                    1 if not ready
*/
check_instrument()
{
        if (strstr(scrn_buf,"READY FOR ANALYSIS") || strstr(scrn_buf, "System Idle"))
return(0);
        else return(1);
}
/*
        NAME:       check_instrument_error - checks analyzer if present and if it is busy
        INPUT:      screen buffer
        RETURN:     indication on the screen of error
                        or
                    continues operation no error
*/
check_instrument_error(int handle)
{
        char entry[0x14];
        static int loop = 0;
        /*
                enable escape key only
        */
        touch(handle, "mode pad", entry);
        if(entry[2] == 'X'){
                beep(800);
                loop = 0;
                return(0);
        }
        /*
                check calibration in progress or sequence aborted - stop user operations
        */
        if(!strstr(scrn_buf, "Auto-Cal in Progress") == NULL ||
                !strstr(scrn_buf, "Gas Cal I in Progress") == NULL ||
                !strstr(scrn_buf, "Gas Cal in Progress") == NULL ||
                !strstr(scrn_buf, "Full Cal in Progress") == NULL ||
                !strstr(scrn_buf, "Elec/Glu/Lac Cal in Progress") == NULL ||
                !strstr(scrn_buf, "Ph + Hct Cal in Progress") == NULL ||
                !strstr(scrn_buf, "SEQUENCE ABORTED") == NULL) {
                        if(!loop){
                                loop = 1;
                                clrscr();
                                sa_hdr(LIGHTRED, "Instrument Busy");
                                puts("\377\377csc/");
                                if(handle){
                                        touch(handle, "group all off", entry);
```

```
                              touch(handle, "group 15 on", entry);
                    }
         }
         delay(500);
         /*
                    display nova
         */
         display_nova();
         return(1);
    }
    else{
         /*
                    analyzer error
         */
         clrscr();
         sa_hdr(YELLOW, "Analysis in Progress");
         puts("\377\377 screwed/");
         sound(1000);
         sleep(3);
         nosound();
         loop = 0;
         return(0);
    }
}
/*
    NAME:        check_status_of_instrument
                 - checks analyzer for calibration in progress
                 - checks if instrument is busy washing out
                 - clears patient data screen
                 - retrieves sample data and errors
                 - exits patient results screen
                 - alerts user to remove sample from port
                 - tests for QNS or aborted sequence
                 - puts data into database
    INPUT:       screen buffer
    RETURN:      next operation for main case statement
*/
check_status_of_instrument(int *send_Nova_MIS_number, RESULTS_DATA *results,
                DATA *data, char *scrn_id, long count)
{
    static int   i = 0, samp_snd = 0;
    int j = 0, the_return, send_this_back = 8;
    if(strstr(scrn_buf,"Acc. #") == NULL){
         display_nova();
         i = 0;
    }
    else {
         if (!i){
             /*
                         sequence completion - show user
             */
             window(10, 6, 57, 25);
             clrscr();
             textcolor(WHITE);
             gotoxy(10, 9);
             cprintf("INSTRUMENT IS WASHING OUT");
             i = 1;
             window(1, 1, 80, 25);
         }
    }
    /*
         escape from patient data screen
    */
    if(!strstr(scrn_buf, "Press CLEAR to Exit") == NULL){
         outportb(0x3f8, 0x7f);
         delay(100);
         send_this_back = 0;
    }
    /*
         wait for proper analysis screen
```

```
*/
if(!strstr(scrn_buf, "Press ANALYZE When Ready") == NULL) return(8);
delay(800);
/*
        clear from patient data screen
*/
if(!strstr(scrn_buf, "PATIENT DATA") == NULL) {
        while(!strstr(scrn_buf, "Press CLEAR to Abort")){
                display_nova();
                outportb(0x3f8, 0x7f);
                sleep(1);
        }
        sa_hdr(YELLOW, "Sample Analysis Sequence");
        *send_Nova_MIS_number = 0;
        send_this_back = 8;
}
/*
        alert user to remove sample from port
*/
if(!strstr(scrn_buf, "Analysis in Progress") == NULL){
        if(!samp_snd){
                sa_hdr(YELLOW, "Remove sample from port");
                sound(1000);
                delay(250);
                sound(500);
                delay(250);
                nosound();
                samp_snd = 1;
        }
        return(8);
}
/*
        sample abort sequence
*/
if(strstr(scrn_buf,"9C INSUFFICIENT SAMP") || strstr(scrn_buf, "SEQUENCE ABORT")) {
        sound(1000);
        clrscr();
        sa_hdr(YELLOW, "Sample Aborted");
        load_abort(results);
        display_nova();
        /*
                get instrument errors
        */
        the_return = sequence_errors(scrn_id, data->errors, scrn_buf);
        for(j = 0; the_return && j < 3; j++){
                the_return = sequence_errors(scrn_id, data->errors, scrn_buf);
        }
        if(j >= 3){
                strcat(data->errors,"Unable to retrieve errors}");
        }
        /*
                put abortive data into database
        */
        put_results_into_database(results, data, count);
        nosound();
        sleep(1);
        return(1);
}
/*
        clear from gas calibration
*/
if(!strstr(scrn_buf,"Gas Cal I in Progress") == NULL) {
        if(!(*send_Nova_MIS_number)) outportb(0x3f8,'D');
        return(0);
}
/*
        check for calibration operations
*/
if(!strstr(scrn_buf, "Gas Cal I in Progress") == NULL ||
```

```
            !strstr(scrn_buf, "Auto-Cal in Progress") == NULL ||
            !strstr(scrn_buf, "Elec/Glu/Lac Cal in Progress") == NULL ||
            !strstr(scrn_buf, "Ph + Hct Cal in Progress") == NULL ||
            !strstr(scrn_buf, "Full Cal in Progress") == NULL ||
            !strstr(scrn_buf, "READY FOR ANALYSIS") == NULL) {
                    return(0);
    }
    /*
            sequence aborted
    */
    if(!strstr(scrn_buf, "SEQUENCE ABORT") == NULL) return(1);
    /*
            sequence termination with user notification
    */
    if(!strstr(scrn_buf,"PATIENT RESULTS at") == NULL) {
            if(!(*send_Nova_MIS_number)) {
                    window(10,6,60,25);
                    clrscr();
                    textcolor(WHITE);
                    gotoxy(10, 9);
                    cprintf("INSTRUMENT IS WASHING OUT");
                    window(1,1,80,25);
                    samp_snd = 0;
                    sleep(3);
                    /*
                            get results from analyzer
                    */
                    get_results_from_screen_buffer(results);
                    /*
                            get instrument errors
                    */
                    the_return = sequence_errors(scrn_id, data->errors, scrn_buf);
                    for(j = 0; the_return && j < 3; j++){
                            the_return = sequence_errors(scrn_id, data->errors,
scrn_buf);
                    }
                    if(j >= 3){
                            strcat(data->errors,"Unable to retrieve errors}");
                    }
                    /*
                            put results into database
                    */
                    put_results_into_database(results, data, count);
                    *send_Nova_MIS_number = 1;
            }
            send_this_back = 8;
    }
    return(send_this_back);
}
/*
    NAME:       cursor_on_off turns cursor off and on
    INPUT:      flag = 0 off; flag = 1 on
    RETURN:     none
*/
cursor_on_off(int flag)
{
    union REGS xr;
    if(!flag){
            xr.h.ah = 1;
            xr.h.ch = 0x20;
            xr.h.cl = 0;
            int86(0x10, &xr, &xr);
    }
    else{
            xr.h.ah = 1;
            xr.h.ch = 7;
            xr.h.cl = 8;
            int86(0x10, &xr, &xr);
    }
}
```

```
 1    /*
            NAME:     data header - displays patient name, sequence number, date and time
 2          INPUT:    data structure and sequence count
            RETURN:   none
 3    */
      data_header(DATA *data, long count)
 4    {
              gotoxy(30, 3);
 5            cprintf("%s", data->pat);
              gotoxy(63, 3);
 6            cprintf("%ld", count);
              gotoxy(10, 6);
 7            cprintf("%s", data->string_time);
              gotoxy(6, 7);
 8            cprintf("%d/%d/%d", data->month, data->day, data->year);
      }
 9    /*
            NAME:     date_time - displays previous sample date and time
10          INPUT:    row - display row
            RETURN:   none
11    */
      date_time(int row, DATA *data)
12    {
              gotoxy(67, row);
13            data->string_time[5] = '\0';
              cprintf("%s", data->string_time);
14            gotoxy(75, row);
              cprintf("%d/%d", data->month, data->day);
15    }
      /*
16          NAME:     display_sample_parameters - displays and changes sample parameters
            INPUT:    user touch entry
17                    sequence number
            RETURN:   parameters in data structure temp, fio2
18    */
      delta_sample_parameters(int handle, int *coding, DATA *data, long count)
19    {
              char entry[0x10];
20            do {
                  if(touch_choice('F', entry, handle)) return(0);
21                beep(800);
                  switch(entry[2]) {
22                    case '@':
                          /*
23                                default values
                          */
24                        textcolor(YELLOW);
                          gotoxy(21, 7);
25                        cprintf("%s", data->pat);
                          gotoxy(21, 8);
26                        cprintf("%s", data->ssn);
                          gotoxy(21, 9);
27                        cprintf("%ld", count);
                          gotoxy(21, 10);
28                        cprintf("%s", data->unit);
                          textcolor(LIGHTGRAY);
29                        gotoxy(6, 13);
                          cprintf("Patient temperature:   ");
30                        data->temp = 37.0;
                          gotoxy(6, 15);
31                        cprintf("Patient FiO2 (in %%):  ");
                          data->fio2 = -1;
32                        gotoxy(6, 17);
                          cprintf("Arterial or venous:    ");
33                        textcolor(LIGHTRED);
                          cprintf("arterial");
34                        data->type = 1;
                          gotoxy(6, 19);
35                        textcolor(LIGHTGRAY);
                          cprintf("Selected Tests:        ");
```

```
                          data->test_select = 1;
                          gotoxy(29, 19);
                          cprintf("                ");
                          gotoxy(29, 19);
                          textcolor(sel_color[data->test_select]);
                          cprintf(test_sel[data->test_select]);
                          gotoxy(42, 7);
                          cputs("       ");
                          *coding = 0;
                          textcolor(YELLOW);
                          gotoxy(29, 13);
                          cprintf("37.0 C");
                          gotoxy(29, 15);
                          cprintf("NFG    %%");
                          break;
                    case 'H':
                          /*
                                  fio2
                          */
                          sa_hdr(YELLOW, "Patient Parameters");
                          calcpd (15, handle, data);
                          touch(handle, "group all off", entry);
                          puts("\377\377clrkeys/");
                          puts("\377\377ccr/");
gotoxy(1,1);
                          puts("\377\377params/");
                          puts ("\377\377esc/");
                          touch(handle, "group 9 on", entry);
                          touch(handle, "group 15 on", entry);
                          entry[2] = '\0';
                          break;
                    case 'C':
                          /*
                                  coding select
                          */
                          gotoxy(42, 7);
                          if(!*coding){
                                  textattr(LIGHTRED + BLINK);
                                  cputs("CODING");
                                  *coding = 1;
                                  textcolor(YELLOW);
                          }
                          else {
                                  cputs("       ");
                                  *coding = 0;
                          }
                          break;
                    case 'S':
                          /*
                                  test select
                          */
                          if(data->test_select++ == 2)
                                  data->test_select = 0;
                          gotoxy(29, 19);
                          cprintf("             ");
                          gotoxy(29, 19);
                          textcolor(sel_color[data->test_select]);
                          cprintf(test_sel[data->test_select]);
                          break;
                    case 'T':
                          /*
                                  temperature
                          */
                          sa_hdr(YELLOW, "Patient Parameters");
                          calcpd(13, handle, data);
                          puts("\377\377clrkeys/");
                          puts("\377\377ccr/");
gotoxy(1,1);
                          puts("\377\377params/");
                          puts ("\377\377esc/");
```

```
                        touch(handle, "group all off", entry);
                        touch(handle, "group 9 on", entry);
                        touch(handle, "group 15 on", entry);
                        entry[2] = '\0';
                        break;
                case 'V':
                        /*
                                sample type aterial,venous
                        */
                        gotoxy (29, 17);
                        if(!data->type) {
                                textcolor(LIGHTRED);
                                cprintf ("arterial");
                                data->type = 1;
                        }
                        else {
                                textcolor(LIGHTBLUE);
                                cprintf ("venous ");
                                data->type = 0;
                        }
                        textcolor(YELLOW);
                        break;
                case 'X':
                        /*
                                escape
                        */
                        beep(950);
                        return(3);
                }
        } while(entry[2] != '!');
        return(0);
}
/*
        NAME:       delta_seq_num - changes sample sequence number and saves to
uva_cnt.db
        INPUT:      count
        RETURN:     count + 1 to uva_cnt.db at approriate unit
*/
delta_seq_num(long *count)
{
        TABLEHANDLE tblhdl, rechdl;
        if((*count)++ >= 49999l) *count = 40000l;
        PXTblOpen("h:\\db\\uva_cnt", &tblhdl, 0, 1);
        PXRecBufOpen(tblhdl, &rechdl);
        PXPutAlpha(rechdl, 1, "TCVPO");
        if(!PXSrchFld(tblhdl, rechdl, 1, SEARCHFIRST)){
                PXRecGet(tblhdl, rechdl);
                PXPutLong(rechdl, 2, *count);
                PXRecUpdate(tblhdl, rechdl);
        }
        PXRecBufClose(rechdl);
        PXTblClose(tblhdl);
        return(6);
}
/*
        NAME:       display_confirm_parameters - displays confirmation of parameters
        INPUT:      coding
                    sequence number
                    data structure with name, unit, history #, temp, fio2, test select, etc
        RETURN:     next operation of controlling case statement
*/
display_confirm_parameters(int handle, int coding, DATA *data, long count)
{
        int send_this_back = 0;
        char entry[0x10];
        touch(handle, "group all off", entry);
        sa_scrn(YELLOW, "Confirmation", LIGHTRED, "Confirm Patient data - place sample in port");
        puts("\377\377cr/");
        puts("\377\377esc/");
```

```
1    touch(handle, "group 8 on", entry);
     touch(handle, "group 15 on", entry);
2    /*
             display patient, ssn, seq #, unit headers
3    */
     textcolor(LIGHTGRAY);
4    gotoxy(10, 7);
     cprintf("Patient Name:");
5    gotoxy(10, 8);
     cprintf("SSN:");
6    gotoxy(10, 9);
     cprintf("Seq #:");
7    gotoxy(10, 10);
     cprintf("Unit:");
8    if(coding){
             gotoxy(42, 7);
9            textattr(LIGHTRED + BLINK);
             cputs("CODING");
10   }
     /*
11           display patient, ssn, seq #, unit values
     */
12   textcolor(YELLOW);
     gotoxy(25, 7);
13   cprintf("%s", data->pat);
     gotoxy(25, 8);
14   cprintf("%s", data->ssn);
     gotoxy(25, 9);
15   cprintf("%ld", count);
     gotoxy(25, 10);
16   cprintf("%s", data->unit);
     textcolor(LIGHTGRAY);
17   gotoxy (6, 13);
     cprintf ("Patient temperature:   ");
18   gotoxy (6, 15);
     cprintf ("Patient FiO2 (in %%):    ");
19   gotoxy (6, 17);
     cprintf ("Arterial or venous:    ");
20   /*
             display panel of tests selected
21   */
     gotoxy (6, 19);
22   cprintf ("Test Selected:         ");
     textcolor(sel_color[data->test_select]);
23   cprintf("%s", test_sel[data->test_select]);
     /*
24           display patient temperature
     */
25   textcolor(YELLOW);
     gotoxy (29, 13);
26   cprintf("%4.1f C", data->temp);
     gotoxy (29, 15);
27   if(data->fio2 = = -1) cprintf(" NFG");
     else cprintf(" %d %%", data->fio2);
28   /*
             display sample type venous,arterial
29   */
     gotoxy (29, 17);
30   if(!data->type){
             textcolor(LIGHTBLUE);
31           cprintf("venous ");
     }
32   else{
             textcolor(LIGHTRED);
33           cprintf ("arterial");
     }
34   if(touch_choice('F', entry, handle))          return(0);
     beep(800);
35   switch(entry[2]) {
             case 'X':
```

```
                        send_this_back = 3;
                        break;
                case '!':
                        if(coding) strcpy(data->errors,"{CP{");
                        clrscr();
                        sa_hdr(YELLOW, "Place sample in port");
                        send_this_back = 7;
                        break;
        }
        return(send_this_back);
}
/*
        NAME:     display_nova - displays nova screen buffer
        INPUT:    screen buffer
        RETURN:   none
*/
display_nova()
{
        unsigned char *scrn_str;
        int temp = (BLACK << 4) + LIGHTGRAY;
        textattr(temp);
        scrn_buf[0x344] = NULL;
        window(10, 6, 52, 25);
        scrn_str = &scrn_buf[45];
        while(*scrn_str){
                if(!(*scrn_str & 0x80)) putch(*scrn_str);
                else {
                        temp = (BLACK << 4) + LIGHTGRAY;
                        if(*scrn_str & 1) temp = (BLACK << 4) + WHITE;
                        else if(*scrn_str & 16) temp = (CYAN << 4) + YELLOW;
                        if(*scrn_str & 32) temp = (BLACK << 4) + LIGHTRED;
                        textattr(temp);
                        putch(' ');
                }
                scrn_str++;
        }
        window(1, 1, 80, 25);
}
/*
        NAME:     display_previous_results - displays previous patient sample results
        INPUT:    data structure with current sample data
        RETURN:   none
*/
display_previous_results(DATA *data, DATA *previous_data)
{
        TABLEHANDLE    tblhdl;
        /*
                clear previous_data structure for last 10 patient results
        */
        memset(previous_data, '\0', sizeof(DATA)*10);
        /*
                display patient demographics
        */
        clrscr();
        puts("\377\377prev/");
        puts("\377\377esc/");
        textbackground(BLACK);
        textcolor(LIGHTGRAY);
        gotoxy(10, 6);
        cprintf("%s", data->pat);
        gotoxy(10, 7);
        cprintf("%s", data->ssn);
        gotoxy(61, 7);
        cprintf("%s", data->devloc);
        gotoxy(30, 1);
        textcolor(LIGHTRED|BLINK);
        cprintf("SEARCHING FILES");
        textcolor(LIGHTGRAY);
        /*
                search raw and last 7 days worth of data for patient samples
```

```
1       */
        PXTblOpen("h:\\db\\uva_raw", &tblhdl, 0, 0);
2       if(!search_and_display(tblhdl, data, previous_data, 1)){
                previous_files(data, previous_data);
3       }
        PXTblClose(tblhdl);
4       gotoxy(30, 1);
        cprintf("                    ");
5       textbackground(BLACK);
        }
6       /*
                NAME:       display_results - display selected patient results with temperature cor-
7       rected blood gases
                INPUT:      data structure
8       RETURN:     none
        */
9       display_results(DATA *data, CALCULATED *cal)
        {
10              DATA       pt;
                textcolor(LIGHTGRAY);
11              textbackground(BLACK);
                /*
12                      patient demographics
                */
13              gotoxy(30, 3);
                cprintf("%s", data->pat);
14              gotoxy(63, 3);
                cprintf("%ld", data->sn);
15              gotoxy(10, 6);
                cprintf("%s", data->string_time);
16              gotoxy(6, 7);
                cprintf("%d/%d/%d", data->month, data->day, data->year);
17              /*
                        temperature correct
18              */
                pt.ph = data->ph;
19              pt.pco2 = data->pco2;
                pt.po2 = data->po2;
20              pt.temp = data->temp;
                pt.hct = data->hct;
21              pt.ca = data->ca;
                temp_correct(&pt);
22              calculated_results(&pt, cal);
                /*
23                      display ph, pco2, po2 if requested
                */
24              if(strcmp(data->profile, "Elec/Glu/Lac")){
                        gotoxy(30, 7);
25                      if(data->ph > 0.0) cprintf("%4.2f", data->ph);
                        else{
26                              if(data->ph == -2) cprintf("NA");
                                else cprintf("QNS");
27                      }
                        gotoxy(29, 8);
28                      if(data->pco2 > 0.0) cprintf("%4.1f  mmHg", data->pco2);
                        else{
29                              if(data->pco2 == -2) cprintf("NA");
                                else cprintf("QNS");
30                      }
                        gotoxy(28, 9);
31                      if(data->po2 > 0.0) cprintf("%4.1f  mmHg", data->po2);
                        else{
32                              if(data->po2 == -2) cprintf("NA");
                                else cprintf("QNS");
33                      }
                        gotoxy(38, 18);
34                      cprintf("%4.1f", data->temp);
                }
35              /*
                        display lytes + Glucose if requested
```

```
*/
if(strcmp(data->profile, "Blood gas")){
        gotoxy(28, 10);
        if(data->hct > 0.0) cprintf("%3.0f    %%", data->hct);
        else{
                if(data->hct == -2) cprintf("NA");
                else cprintf("QNS");
        }
        gotoxy(28, 11);
        if(data->na > 0.0) cprintf("%5.1f mmol/L", data->na);
        else{
                if(data->na == -2) cprintf("NA");
                else cprintf("QNS");
        }
        gotoxy(29, 12);
        if(data->k > 0.0) cprintf("%4.1f mmol/L", data->k);
        else{
                if(data->k == -2) cprintf("NA");
                else cprintf("QNS");
        }
        gotoxy(28, 13);
        if(data->cl > 0.0) cprintf("%5.1f mmol/L", data->cl);
        else{
                if(data->cl == -2) cprintf("NA");
                else cprintf("QNS");
        }
        gotoxy(29, 14);
        if(data->ca > 0.0) cprintf("%5.2f mmol/L", data->ca);
        else{
                if(data->ca == -2) cprintf("NA");
                else cprintf("QNS");
        }
        gotoxy(28, 15);
        if(data->gluc > 0.0){
                cprintf("%3.0f    mg/dl", data->gluc);
                if(data->gluc > 500.00) cprintf(" NOT");
        }
        else{
                if(data->gluc == -2) cprintf("NA");
                else cprintf("QNS");
        }
/*
        gotoxy(30, 16);
        if(data->lac > 0.0) cprintf("%3.1f mmol/L", data->lac);
        else{
                if(data->lac == -2) cprintf("NA");
                else cprintf("QNS");
        }
*/
}
/*
        calculated values display if requested
*/
if(strcmp(data->profile, "Elec/Glu/Lac")){
        gotoxy(59, 8);
        if ((data->ph > 0.0) && (data->pco2 > 0.0) && (data->hct > 0.0)){
                cprintf("%6.1f mmol/L", cal->bc_b);
        }
        else{
                cprintf(" N/A");
        }
        gotoxy(59, 9);
        if ((data->ph > 0.0) && (data->pco2 > 0.0)){
                cprintf("%6.1f mmol/L", cal->hco3);
        }
        else{
                cprintf(" N/A");
        }
        gotoxy(59, 10);
        if ((data->ph > 0.0) && (data->pco2 > 0.0)){
```

```
 1                          cprintf("%6.1f mmol/L", cal->tco2);
                    }
 2                  else{
                            cprintf("  N/A");
 3                  }
                    gotoxy(59, 11);
 4                  if ((data->ph > 0.0) && (data->po2 > 0.0) && (data->pco2 > 0.0)){
                            cprintf("%6.1f %%%%", cal->o2sat);
 5                  }
                    else{
 6                          cprintf("  N/A");
                    }
 7                  gotoxy(59, 12);
                    if ((data->ph > 0.0) && (data->po2 > 0.0) && (data->pco2 > 0.0) && (data->hct
 8           > 0.0)){
                            cprintf("%6.1f ml/dl", cal->o2ct);
 9                  }
                    else{
10                          cprintf("  N/A");
                    }
11          }
            if(strcmp(data->profile, "BG")){
12                  gotoxy(59, 13);
                    if ((data->ph > 0.0) && (data->ca > 0.0)){
13                          cprintf("%6.1f mmol/L", cal->nca);
14                  }
                    else{
                            cprintf("  N/A");
15                  }
                    gotoxy(59, 14);
16          }
            if(strcmp(data->profile, "Elec/Glu/Lac")){
17                  if (data->hct > 0.0){
                            cprintf("%6.1f g/dl", cal->hb);
18                          if(data->hct < 20.00) cprintf(" NOT");
                    }
19                  else{
                            cprintf("  N/A");
20                  }
            }
21          gotoxy(60, 15);
            if(data->fio2 > 0.0) cprintf(" %d %%%%", data->fio2);
22          else cprintf("NFG");
            if(strcmp(data->profile, "Elec")){
23                  /*
                            display temperture corrected if requested
24                  */
                    if(data->temp != 37.0){
25                          textcolor(WHITE);
                            gotoxy(31, 20);
26                          cprintf("pH:   ");
                            gotoxy(31, 21);
27                          cprintf("pco2: ");
                            gotoxy(31, 22);
28                          cprintf("po2:  ");
                            textcolor(LIGHTGRAY);
29                          gotoxy(40, 20);
                            if(data->ph > 0.0) cprintf("%4.2f    ",pt.ph);
30                          else{
                                    if(data->ph == -2) cprintf("NA");
31                                  else cprintf("QNS");
                            }
32                          gotoxy(38, 21);
                            if(data->pco2 > 0.0) cprintf("%5.1f    mmHg", pt.pco2);
33                          else{
                                    if(data->pco2 == -2) cprintf("NA");
34                                  else cprintf("QNS");
                            }
35                          gotoxy(38, 22);
                            if(data->po2 > 0.0) cprintf("%5.1f    mmHg", pt.po2);
```

```
                        else{
                                if(data->po2 = = -2) cprintf("NA");
                                else cprintf("QNS");
                        }
                }
        }
        textcolor(LIGHTGRAY);
        gotoxy(38, 18);
        cprintf("%4.1f", data->temp);
}
/*
        NAME:    display sample parameters - displays default patient parameters
        INPUT:   user touch entry
                 sequence number
                 data structure
        RETURN:  none
*/
display_sample_parameters(int handle, DATA *data, long count)
{
        char entry[0x10];
        clrscr();
        touch(handle, "group all off", entry);
        sa_hdr(YELLOW, "Patient Parameters");
        puts("\377\377ccr/");
        puts("\377\377params/");
        puts ("\377\377esc/");
        gotoxy(1,1);
        touch(handle, "group 9 on", entry);
        touch(handle, "group 15 on", entry);
        gotoxy(21, 7);
        cprintf("%s", data->pat);
        gotoxy(21, 8);
        cprintf("%s", data->ssn);
        gotoxy(21, 9);
        cprintf("%ld", count);
        gotoxy(21, 10);
        cprintf("%s", data->unit);
        textcolor(LIGHTGRAY);
        gotoxy (6, 13);
        cprintf("Patient temperature:   ");
        data->temp = 37.0;
        gotoxy (6, 15);
        cprintf ("Patient FiO2 (in %%):   ");
        data->fio2 = -1;
        gotoxy (6, 17);
        cprintf ("Arterial or venous:    ");
        textcolor(LIGHTRED);
        cprintf("arterial");
        gotoxy(6, 19);
        textcolor(LIGHTGRAY);
        cprintf("Selected Tests:        ");
        textcolor(sel_color[data->test_select]);
        cprintf("%s", test_sel[data->test_select]);
        textcolor(YELLOW);
        gotoxy (29, 13);
        cprintf("37.0 C");
        gotoxy (29, 15);
        cprintf("NFG   %%");
        data->type = 1;
}
/*
        NAME:    find_history_number - takes user input and searches uva_pats for
selected patient history number
                                                 displays patient name, location for
user confirmation of search
        INPUT:   user touch entry
                 data structure
        RETURN:  name, location, history number in data structure
*/
find_history_number(int handle, DATA *data)
```

```
{
    TABLEHANDLE    tblhdl;
    RECORDHANDLE   rechdl;
    int exit = 0, count = 0, row = 3, col = 64, length = 10;
    int send_this_back;
    char entry[0x10], fld[11];
    /*
            setup touch screen
    */
    sa_scrn(YELLOW, "Search Database by SSN", YELLOW, "Enter SS Number to be searched");
    puts("\377\377keys/");
    puts("\377\377esc/");
    touch(handle, "group all off", entry);
    touch(handle, "group 1 on", entry);
    touch(handle, "group 15 on", entry);
    textcolor(WHITE);
    /*
            user entry for selecting desired history number
    */
    do {
        do {    if(!touch_choice('F', entry, handle)){
                    switch(entry[2]) {
                        case '@':
                            /*
                                    clear entry
                            */
                            beep(850);
                            count = 0;
                            col = 64;
                            textbackground(BLACK);
                            gotoxy(56, row);
                            cprintf("          ");
                            strcpy(fld, "          ");
                            break;
                        case 'S':
                            /*
                                    search database selected
                            */
                            sa_scrn(YELLOW, "Search Database by SSN", YELLOW, "Enter SS Number to be searched");
                            beep(750);
                            puts("\377\377keys/");
                            puts("\377\377 esc/");
                            touch(handle, "group all off",entry);
                            touch(handle, "group 1 on",entry);
                            touch(handle, "group 15 on",entry);
                            count = 0;
                            col = 64;
                            strcpy(fld,"          ");
                            break;
                        case 'X':
                            /*
                                    escape
                            */
                            beep(800);
                            entry[2] = '!';
                            send_this_back = 0;
                            exit = 1;
                            break;
                        case 'A':
                            /*
                                    accept selected histroy number
                            */
                            beep(800);
                            entry[2] = '!';
                            send_this_back = 6;
                            exit = 1;
                            break;
```

```
                                    case '!':
                                            beep(800);
                                            break;
                                    default:
                                            /*
                                                    user input of a number
                                            */
                                            beep(700);
                                            if(count < length) {
                                                    gotoxy(col++, row);
                                                    cprintf("%c", fld[count++] = entry[2]);
                                            }
                                            else {
                                                    beep(550);
                                            }
                                            break;
                            }
                    }
                    else {
                            entry[2] = '!';
                            exit = 1;
                            send_this_back = 0;
                    }
            } while (entry[2] != '!');
            if(exit) return(send_this_back);
            fld[count] = NULL;
            /*
                    search database
            */
            PXTblOpen("h:\\db\\uva_pats", &tblhdl, 0, 0);
            PXRecBufOpen(tblhdl, &rechdl);
            PXPutAlpha(rechdl, 5, fld);
            if(!PXSrchFld(tblhdl, rechdl, 5, SEARCHFIRST)) {
                    PXRecGet(tblhdl, rechdl);
                    /*
                            get name, location, history
                    */
                    PXGetAlpha(rechdl, 2, 20, data->pat);
                    PXGetAlpha(rechdl, 5, 10, data->ssn);
                    PXGetAlpha(rechdl, 1, 10, data->unit);
                    sa_scrn(YELLOW, "Search Database by SSN", YELLOW, "SS Number Matched");
                    puts("\377\377his_acc/");
                    puts("\377\377his_srch/");
                    puts("\377\377esc/");
gotoxy(1, 1);
                    touch(handle, "group all off", entry);
                    touch(handle, "group 3 on", entry);
                    touch(handle, "group 4 on", entry);
                    touch(handle, "group 15 on", entry);
                    /*
                            display selected patinet name, history, unit
                    */
                    textcolor(LIGHTGRAY);
                    gotoxy(10, 10);
                    cprintf("Name:    ");
                    gotoxy(10, 12);
                    cprintf("SSN:     ");
                    gotoxy(10, 14);
                    cprintf("Unit:    ");
                    textcolor(YELLOW);
                    gotoxy(20, 10);
                    cprintf("%s",data->pat);
                    gotoxy(20, 12);
                    cprintf("%s",data->ssn);
                    gotoxy(20, 14);
                    cprintf("%s",data->unit);
            }
            else {
```

```
1       sa_scrn(YELLOW, "Search Database by SSN", LIGHTRED, "SS Number Not Matched");
2       puts("\377\377his_srch/");
        puts("\377\377esc/");
3       touch(handle, "group all off", entry);
        touch(handle, "group 4 on", entry);
4       touch(handle, "group 15 on", entry);
        gotoxy(64,3);
5       cprintf("%s",fld);
        }
6       PXRecBufClose(rechdl);
        PXTblClose(tblhdl);
7       } while(!exit);
        return(send_this_back);
8       }
        /*
9       NAME:    get_search_data - gets user data (access, name, unit, phone)
        INPUT:   database recordhandle
10               pic_data structure
        RETURN:  pertinent data in pic_data structure
11      */
        get_search_data(RECORDHANDLE rechdl, PIC_DATA *pic_data)
12      {
        PXGetAlpha(rechdl, 1, 10, pic_data->access);
13      PXGetAlpha(rechdl, 3, 20, pic_data->name);
        PXGetAlpha(rechdl, 6, 10, pic_data->unit);
14      PXGetAlpha(rechdl, 5, 10, pic_data->ssn);
        PXGetAlpha(rechdl, 7, 15, pic_data->phone);
15      }
        /*
16      NAME:    get_results gets the patient results from a database
        INPUT:   database table and record handle
17               data structure
        RETURN:  data structure loaded
18      */
        get_results(RECORDHANDLE rechdl, DATA *data)
19      {
        PXGetAlpha(rechdl, 1, 20, data->pat);
20      PXGetAlpha(rechdl, 2, 10, data->ssn);
        PXGetLong(rechdl, 5 , &data->sn);
21      PXGetAlpha(rechdl, 4, 10, data->access);
        PXGetDoub(rechdl, 6, &data->bp);
22      PXGetDoub(rechdl, 7, &data->temp);
        PXGetDoub(rechdl, 8, &data->ph);
23      PXGetDoub(rechdl, 9, &data->pco2);
        PXGetDoub(rechdl, 10, &data->po2);
24      PXGetDoub(rechdl, 11, &data->hct);
        PXGetDoub(rechdl, 12, &data->na);
25      PXGetDoub(rechdl, 13, &data->k);
        PXGetDoub(rechdl, 14, &data->cl);
26      PXGetDoub(rechdl, 15, &data->ca);
        PXGetDoub(rechdl, 16, &data->gluc);
27      /* PXGetDoub(rechdl, 27, &data->lac);*/
        PXGetShort(rechdl, 17, &data->type);
28      PXGetShort(rechdl, 18, &data->fio2);
        PXGetAlpha(rechdl, 19, 6, data->devloc);
29      PXGetAlpha(rechdl, 22, 10, data->string_time);
        PXGetDate(rechdl, 20, &data->date);
30      PXDateDecode(data->date, &data->month, &data->day, &data->year);
        PXGetAlpha(rechdl, 25, 20, data->profile);
31      PXGetAlpha(rechdl, 23, 10, data->status);
        }
32      /*
        NAME:    get_results_from_screen - retrieve analytes from nova screen
33      INPUT:   screen buffer
                 results_data structure
34      RETURN:  loaded results_data structure
        */
35      get_results_from_screen_buffer(RESULTS_DATA *results_data)
        {
```

```
1     char           *point_to_here, temp_data[10];
      char           *end;
2     register       count;
      int            i = 2, status = 0;
3     double         *data_p;
      /*
4          find appropriate header
      */
5     while(scrn_header[i]){
          switch(i){
6             case 0:
              case 1:
7                 break;
              case 2:
8                 data_p = &results_data->bp;
                  break;
9             case 3:
                  data_p = &results_data->ph;
10                break;
              case 4:
11                data_p = &results_data->pco2;
                  break;
12            case 5:
                  data_p = &results_data->po2;
13                break;
              case 6:
14                data_p = &results_data->hct;
                  break;
15            case 7:
                  data_p = &results_data->na;
16                break;
              case 8:
17                data_p = &results_data->k;
                  break;
18            case 9:
                  data_p = &results_data->cl;
19                break;
              case 10:
20                data_p = &results_data->ca;
                  break;
21            case 11:
                  data_p = &results_data->gluc;
22                break;
      /*
23            case 12:
                  data_p = &results_data->lac;
24                break;
      */
25        }
          /*
26            find selected header in buffer
          */
27        point_to_here = strstr(scrn_buf, scrn_header[i]);
          if(point_to_here == NULL){
28            status = 1;
              count = 20;
29            point_to_here = scrn_buf;
          }
30        else{
              point_to_here += 4;
31            count = 0;
          }
32        while(!isdigit(*point_to_here) && (*point_to_here != 'u') &&
                count < 15){
33            point_to_here++;
              count++;
34        }
          /*
35            results not available
          */
```

```
             if(count > = 15){
                     strcpy(temp_data, "-1");
             }
             else {
                     /*
                             get results
                     */
                     for(count = 0; (*point_to_here != ' ') &&
                                     (*point_to_here < '@'); point_to_here++){
                             if (*point_to_here <= '9'){
                                     temp_data[count++] = *point_to_here;
                                     temp_data[count] = NULL;
                             }
                     }
                     /*
                             analyte uncalibrated
                     */
                     if(*point_to_here == 'u') strcpy(temp_data, "-2");
             }
             *data_p = strtod(temp_data, &end);
             i++;
     }
     return(status);
}
/*
     NAME:       get_unit_auth - get unit authority gets the user's authority code
     INPUT:      pic_data structure
     RETURN:     pic_data authority set
*/
get_unit_auth(RECORDHANDLE rechdl, PIC_DATA *pic_data)
{
     PXGetAlpha(rechdl, 4, 10, pic_data->auth);
     PXGetAlpha(rechdl, 6, 10, pic_data->unit);
}
/*
     NAME:       idle_screen - screen saver for sa with user activation
     INPUT:      none
     RETURN:     none
*/
idle_screen(int handle)
{
     char entry[0x10];
     if(handle){
             touch(handle, "group all off", entry);
             touch(handle, "group 10 on", entry);
     }
     /*
             wait for user touch
     */
     do {
             scrn_save(handle);
             touch(handle, "mode pad", entry);
     } while(entry[0] != 'F');
     beep(700);
     return(0);
}
/*
     NAME:       initialize_instrument - prepares instrument for sample analysis
     INPUT:      screen buffer
                 pic_data authority
     RETURN:     next operation for main case
*/
initialize_instrument(int *send_Nova_MIS_number, PIC_DATA *pic_data)
{
     unsigned    char *pointer;
     time_t      start_time, present_time;
     int         i;
     *send_Nova_MIS_number = 0;
     /*
             send analyze request
```

```
 1    */
      outportb(0x3f8, 'A');
 2    sleep(1);
      display_nova();
 3    if(!strstr(scrn_buf, "Press ANALYZE When Ready")){
              if(strstr(scrn_buf, "READY FOR ANALYSIS")){
 4                    window(10, 6, 62, 25);
                      clrscr();
 5                    textcolor(WHITE);
                      gotoxy(5,9);
 6                    cprintf("INSTRUMENT IS PRIMING - PLEASE WAIT");
                      window(1, 1, 80, 25);
 7                    sleep(10);
              }
 8            outportb(0x3f8, 'A');
              sleep(1);
 9            if(!strstr(scrn_buf, "Press ANALYZE When Ready")){
                      nova_screen_reset();
10                    return(0);
              }
11    }
      /*
12            go to service menu
      */
13    outportb(0x3f8,'H');
      delay(100);
14    outportb(0x3f8,'3');
      delay(500 * 3);
15    if(pic_data->auth[0] = = 3) display_nova();
      if(!strstr(scrn_buf, "SERVICE MENU")){
16            nova_screen_reset();
              outportb(0x3f8,'H');
17            delay(100);
              outportb(0x3f8,'3');
18            delay(500 * 2);
              if(!strstr(scrn_buf, "SERVICE MENU")){
19                    nova_screen_reset();
                      return(1);
20            }
      }
21    /*
              goto system test
22    */
      outportb(0x3f8, '1');
23    delay(1500);
      if(pic_data->auth[0] = = 3) display_nova();
24    if(!strstr(scrn_buf, "SYSTEM TEST")){
              outportb(0x3f8, '1');
25            delay(500 * 2);
              if(!strstr(scrn_buf, "SYSTEM_TEST")){
26                    nova_screen_reset();
                      return(1);
27            }
      }
28    /*
              find probe position
29    */
      pointer = strstr(scrn_buf, "Sampler Position");
30    pointer += 19;
      time(&start_time);
31    while(*pointer != '9'){
              if(time(&present_time) - start_time > 20) {
32                    nova_screen_reset();
                      outportb(0x3f8, 0x7f);
33                    return(1);
              }
34            if(pic_data->auth[0] = = '3') display_nova();
      }
35    if(pic_data->auth[0] = = '3') display_nova();
      /*
```

```
                send second request for analysis
        */
        outportb(0x3f8, 'A');
        delay(100);
        *send_Nova_MIS_number = 1;
        for(i = 0; i < 30 ; i++){
                outportb(0x3f8, 0x7f);
                sleep(1);
                if(strstr(scrn_buf, "Press ANALYZE When Ready")) break;
        }
        return(8);
}
/*
        NAME:       irq_func - interrupt function for nova communications
        INPUT:      screen buffer
        RETURN:     screen buffer loaded
*/
void interrupt irq_func()
{
        static in_cnt = 0, flag = 0x80;
        static unsigned char temp[3];
        switch(flag){
                case 0x00:
                {
                        /*
                                data within the string
                        */
                        temp[0] = temp[1];
                        temp[1] = scrn_buf[in_cnt];
                        switch(scrn_buf[in_cnt++] = inportb(0x3f8)){
                                case NULL:
                                        /*
                                                end of string
                                        */
                                        scrn_buf[--in_cnt] = temp[1];
                                        scrn_buf[--in_cnt] = temp[0];
                                        flag = 0x80;
                                        break;
                                case 0x0c:
                                        /*
                                                clear screen buffer
                                        */
                                        setmem(scrn_buf, 0x344, 0x20);
                                        flag = 0x80;
                                        break;
                        }
                        break;
                }
                case 0x40:
                        /*
                                command string follows
                        */
                        if(inportb(0x3f8) != 'C') { flag = 0x80;}
                        else {flag++;}
                        break;
                case 0x41:
                        /*
                                y axis position
                        */
                        in_cnt = inportb(0x3f8) * 0x2b;
                        flag++;
                        break;
                case 0x42:
                        /*
                                x axis position
                        */
                        in_cnt += inportb(0x3f8);
                        flag = 0x00;
                        break;
                case 0x80:
```

```
                        /*
                                clear screen
                        */
                        if(inportb(0x3f8) == 0x0b) flag = 0x40;
                        break;
                }
        outportb(0x20, 0x20);
}
/*
        NAME:       linear_display - displays the previous 10 patient samples
        INPUT:      data structure with patient data
                    row of screen to be displayed
        RETURN:     none
*/
linear_display(DATA *data, int row)
{
        /*
                display ph,pco2,po2 if requested
        */
        if(strcmp(data->profile, "Elec/Glu/Lac")){
                gotoxy(2, row);
                if(data->ph > 0.0) cprintf("%4.3f", data->ph);
                else{
                        if(data->ph == -2) cprintf("NA");
                        else cprintf("QNS");
                }
                gotoxy(10, row);
                if(data->pco2 > 0.0) cprintf("%5.1f",data->pco2);
                else{
                        if(data->pco2 == -2) cprintf("NA");
                        else cprintf("QNS");
                }
                gotoxy(18, row);
                if(data->po2 > 0.0) cprintf("%5.1f",data->po2);
                else{
                        if(data->po2 == -2) cprintf("NA");
                        else cprintf("QNS");
                }
        }
        /*
                display lytes + gluc if requested
        */
        if(strcmp(data->profile, "Blood gas")){
                gotoxy(24, row);
                if (data->hct > 0.0){
                        if(data->hct > 19.9) cprintf("%3.0f", data->hct);
                        else cprintf(" NOT");
                }
                else{
                        if(data->hct == -2) cprintf("NA");
                        else cprintf("QNS");
                }
                gotoxy(29, row);
                if (data->na > 0.0) cprintf("%5.1f", data->na);
                else{
                        if(data->na == -2) cprintf("NA");
                        else cprintf("QNS");
                }
                gotoxy(35, row);
                if (data->k > 0.0) cprintf("%4.1f", data->k);
                else{
                        if(data->k == -2) cprintf("NA");
                        else cprintf("QNS");
                }
                gotoxy(40, row);
                if (data->cl > 0.0) cprintf("%4.0f", data->cl);
                else{
                        if(data->cl == -2) cprintf("NA");
                        else cprintf("QNS");
                }
```

```
                gotoxy(46, row);
                if (data->ca > 0.0) cprintf("%5.2f", data->ca);
                else{
                        if(data->ca == -2) cprintf("NA");
                        else cprintf("QNS");
                }
                gotoxy(53, row);
                if (data->gluc > 0.0){
                        if(data->gluc < 500.0) cprintf("%4.0f",data->gluc);
                        else cprintf(" NOT");
                }
                else{
                        if(data->gluc == -2) cprintf("NA");
                        else cprintf("QNS");
                }
/*
                gotoxy(60, row);
                if (data->lac > 0.0) cprintf("%4.1f",data->lac);
                else{
                        if(data->lac == -2) cprintf("NA");
                        else cprintf("QNS");
                }
*/
        }
/*
                display date and time
*/
        gotoxy(67, row);
        data->string_time[5] = '\0';
        cprintf("%s", data->string_time);
        gotoxy(75, row++);
        cprintf("%d/%d", data->month, data->day);
}
/*
        NAME:   load_abort - loads results with aborted sample indicators
        INPUT:  results_data structure
        RETURN: loaded results
*/
load_abort(RESULTS_DATA *results)
{
        results->bp = -1;
        results->ph = -1;
        results->pco2 = -1;
        results->hct = -1;
        results->po2 = -1;
        results->na = -1;
        results->k = -1;
        results->cl = -1;
        results->ca = -1;
        results->gluc = -1;
        results->lac = -1;
}
/*
        NAME:   load_unit_array - loads the unit array with valid units within given
floors
        INPUT:  unit structure
                data structure
        RETURN: unit structure loaded
*/
load_unit_array(UNITS *units, DATA *data)
{
        static int max_unit_cnt = 0;
        TABLEHANDLE     tblhdl;
        RECORDHANDLE    rechdl;
        short flr;
        PXTblOpen("h:\\db\\uva_unit", &tblhdl, 0, 0);
        PXRecBufOpen(tblhdl, &rechdl);
        max_unit_cnt = 0;
        PXPutAlpha(rechdl, 1, data->unit);
        if(!PXSrchFld(tblhdl, rechdl, 1, SEARCHFIRST)){
```

```
                strcpy((units+max_unit_cnt++)->location, data->unit);
        }
        else{
                PXPutAlpha(rechdl, 1, "TCVPO");
                if(!PXSrchFld(tblhdl, rechdl, 1, SEARCHFIRST)){
                        strcpy((units+max_unit_cnt++)->location, "TCVPO");
                }
                else{
                        strcpy((units+max_unit_cnt++)->location, "QC");
                }
        }
        PXRecFirst(tblhdl);
        do{
                PXRecGet(tblhdl, rechdl);
                PXGetShort(rechdl, 2, &flr);
                if(flr > 2 || flr < 5){
                        PXGetAlpha(rechdl, 1, 20, (units+max_unit_cnt)->location);
                        if(strcmp((units+max_unit_cnt)->location, units->location))
max_unit_cnt++;
                }
        } while(!PXRecNext(tblhdl));
        PXRecBufClose(rechdl);
        PXTblClose(tblhdl);
        return(max_unit_cnt);
}
/*
        NAME:       logscrn - allows user to login to system taking access and verify code
for checking
        INPUT:      data structure
                    pic_data structure
        RETURN:     access and verify codes
*/
logscrn(int handle, DATA *data, PIC_DATA *pic_data)
{
        char entry[0x10], fld[10];
        int x = 1, count = 0, row = 3, col = 65, length = 9;
        /*
                display main screen
        */
        textbackground(BLACK);
        clrscr();
        puts("\377\377header/");
        textcolor(YELLOW);
        gotoxy(4, 3);
        cprintf("     UVa HSC - Standalone System");
        textcolor(YELLOW);
        puts("\377\377 keys/");
        puts("\377\377 alphakey/");
        touch(handle,"group all off", entry);
        touch(handle,"group 1 on", entry);
        touch(handle,"group 18 on", entry);
        strset(fld,'\0');
        do{
                do{
                        if(touch_choice('F', entry, handle)) return(12);
                        switch(entry[2]){
                        case '@':
                                /*
                                        clear entry
                                */
                                beep(850);
                                gotoxy(64, 3);
                                cprintf("         ");
                                col -= count;
                                count = 0;
                                strset (fld, '\0');
                                break;
                        case '!':
                                /*
                                        accept entry
```

```
                        */
            beep(800);
            fld[count] = NULL;
            break;
    default:
            /*
                    user input
            */
            beep(700);
            if(count < length){
                    gotoxy(col++, row);
                    cprintf("%c", (fld[count++] = entry[2]));
            }
            else beep(550);
            break;
    }
} while(entry[2] != '!');
/*
        test access code for validity
*/
strcpy(pic_data->access, fld);
if(count <= length) verify_scrn(handle, pic_data);
x = access_search(pic_data);
if(x){
        puts("\377\377 clr_hdr/");
        sa_hdr(LIGHTRED|BLINK, "Not a Valid Access Code - Reenter");
        beep(1000);
        beep(500);
        sleep(2);
        puts("\377\377 clr_hdr/");
        sa_hdr(LIGHTRED, "Enter Access Code");
        gotoxy(65, 3);
        cprintf("        ");
        strset(fld, '\0');
        col = 65;
        count = 0;
        textcolor(YELLOW);
}
} while(x);
strcpy(data->access, fld);
return(1);
}
/*
        NAME:    long_time_to_date - converts seconds into a date and time
        INPUT:   number of seconds
                 time string
                 date string
        RETURN:  loaded date and time strings
*/
char *long_to_time_and_date(time_t *time_in_seconds, char *time_string,
                                        char *date_string)
{
    struct tm           *time_structure;
    char    *time_point, *date_point;
    char    *months[] = {"Jan","Feb","Mar","Apr","May","Jun","Jul",
                                        "Aug","Sep","Oct","Nov","Dec"};
    time_structure = localtime(time_in_seconds);
    time_point = time_string;
    date_point = date_string;
    if(time_structure->tm_hour < 10){
            *time_point++ = '0';
            itoa(time_structure->tm_hour,time_point,10);
            time_point--;
    }
    else {
            itoa(time_structure->tm_hour,time_point,10);
    }
    strcat(time_string,":");
    time_point += 3;
    if(time_structure->tm_min < 10){
```

```
            *time_point++ = '0';
            itoa(time_structure->tm_min,time_point,10);
            time_point--;
        }
        else {
            itoa(time_structure->tm_min,time_point,10);
        }
        strcat(time_string,":");
        time_point += 3;
        if(time_structure->tm_sec < 10){
            *time_point++ = '0';
        }
        itoa(time_structure->tm_sec,time_point,10);
        strcpy(date_point,months[time_structure->tm_mon]);
        strcat(date_point," ");
        date_point += 4;
        if(time_structure->tm_mday < 10){
            *date_point++ = '0';
            itoa(time_structure->tm_mday,date_point,10);
            date_point--;
        }
        else
            itoa(time_structure->tm_mday,date_point,10);
        date_point++;
        strcat(date_point,", ");
        date_point += 3;
        itoa((time_structure->tm_year + 1900),date_point,10);
        return(time_string);
}
/*
        NAME:       main_dis_nova - maintenance display nova. used to display the nova
screen in the proper location during maintenance
        INPUT:      screen buffer
        RETURN:     none
*/
main_dis_nova()
{
        unsigned char *scrn_str;
        int temp = (BLACK < 4) + LIGHTGRAY;
        textattr(temp);
        scrn_buf[0x344] = NULL;
        /*
                size window to nova screen size
        */
        window(20, 7, 62, 25);
        scrn_str = &scrn_buf[45];
        /*
                display char's
        */
        while(*scrn_str){
            if(!(*scrn_str & 0x80)) putch(*scrn_str);
            else {
                    temp = (BLACK << 4) + LIGHTGRAY;
                    if(*scrn_str & 1) temp = (BLACK << 4) + WHITE;
                    else if(*scrn_str & 16) temp = (CYAN << 4) + YELLOW;
                    if(*scrn_str & 32) temp = (BLACK << 4) + LIGHTRED;
                    textattr(temp);
                    putch(' ');
            }
            scrn_str++;
        }
        window(1, 1, 80, 25);
}
/*
        NAME:       no_sample_results - display to the user that no results were available
for that patient
        INPUT:      data structure
        RETURN:     none
*/
no_sample_data(int handle, DATA *data)
```

```
1    {
            char entry[10];
2        /*
                display patient name, location, history # and no results
3        */
            sa_scrn(YELLOW, "Patient Results Search", LIGHTRED, "No results for selected
4    patient");
            puts("\377\377esc/");
5        touch(handle,"group all off",entry);
            touch(handle,"group 15 on",entry);
6        textcolor(LIGHTGRAY);
            gotoxy(10, 10);
7        cprintf("Name:    ");
            gotoxy(10, 12);
8        cprintf("SSN:    ");
            gotoxy(10, 14);
9        cprintf("Unit:    ");
            textcolor(YELLOW);
10       gotoxy(20, 10);
            cprintf("%s", data->pat);
11       gotoxy(20, 12);
            cprintf("%s", data->ssn);
12       gotoxy(20, 14);
            cprintf("%s", data->unit);
13       /*
                touch exit
14       */
            if(touch_choice('F', entry, handle))        return;
15       if(entry[2] == 'X'){
                beep(600);
16           return;
            }
17   }
     /*
18       NAME:       nova_ctl - nova control used during maintenance to control nova
     analyzer
19       INPUT:      user touch entry
            RETURN:   none
20   */
     nova_ctl(int handle)
21   {
            int i;
22       char entry[0x10];
            time_t start_time,now_time;
23       /*
                display maintenance screen
24       */
            puts("\377\377monitor/");
25       puts("\377\377escape/");
            touch(handle, "group all off", entry);
26       touch(handle, "group 11 on", entry);
            /*
27           user input of nova control
            */
28       do {
                time(&start_time);
29           do {
                    main_dis_nova();
30               touch(handle,"mode Pad",entry);
                    if(time(&now_time) > (start_time + 300)) {
31                   for(i = 0; i < 4; i++) {
                            outportb(0x3f8,0x7f);
32                       delay(200);
                        }
33                   sleep(1);
                        if((!strstr(scrn_buf, "SEQUENCE ABORTED") == NULL)) {
34                       outportb(0x3f8, 0x7f);
                            delay(200);
35                   }
                    return(0);
```

```
                    }
            } while(entry[0] != 'F');
            if(strncmp(&entry[2], "NONE", 4)) beep(700);
            if(entry[2] == 'E')     outportb(0x3f8, 0x0d);
            else if(entry[2] == 'R') outportb(0x3f8, 0x7f);
            else if(entry[2] == 'X'){
                    /*
                            exit routine
                    */
                    for(i = 0; i < 4; i++) {
                            outportb(0x3f8, 0x7f);
                            delay(200);
                    }
                    sleep(1);
                    if((!strstr(scrn_buf, "SEQUENCE ABORTED") == NULL)) {
                            outportb(0x3f8, 0x7f);
                            delay(200);
                    }
            }
            else outportb(0x3f8, entry[2]);
    } while(entry[2] != 'X');
    return(0);
}
/*
    NAME:       nova_print - print patient results
    INPUT:      data structure
                calculated structure
    RETURN:     none
*/
nova_print(DATA *data, CALCULATED *cal)
{
        DATA        pt;
        struct date date;
        struct time dtime;
        int prn_status;
        /*
            test printer
        */
        if((prn_status = printer_status()) != 0x90) {
                return(prn_status);
        }
        gettime(&dtime);
        getdate(&date);
        fprintf(stdprn,"University of Virginia Medical Center\n");
        fprintf(stdprn, "Charlottesville, Virginia\n");
        fprintf(stdprn, "Remote Standalone System\n\n");
        fprintf (stdprn,"Report Time:     %02d/%02d/%d    %02d:%02d:%02d\n",
                date.da_mon, date.da_day, date.da_year,
                dtime.ti_hour, dtime.ti_min, dtime.ti_sec);
        fprintf (stdprn,"Patient name:    ");
        fprintf (stdprn,"%s\n", data->pat);
        fprintf (stdprn,"SSN:             %s\n", data->ssn);
        fprintf (stdprn,"Sample number:   %ld\n", data->sn);
        fprintf (stdprn,"Analysis time:   ");
        fprintf (stdprn,"%s\n", data->string_time);
        fprintf (stdprn,"Analysis Date:   %02d/%02d/%d\n", data->month,
                                                data->day, data->year);
        fprintf(stdprn,"Location:        %s\n",data->devloc);
        fprintf(stdprn,"Sample Type:    ");
        data->type ? fprintf(stdprn,"Arterial\n\n"):
                                                fprintf(stdprn,"Venous\n\n");
        /*
            print ph, pco2, po2 if requested
        */
        if(strcmp(data->profile, "Elec/Glu/Lac")){
                fprintf(stdprn,"    pH:         ");
                if(data->ph > 0.0) fprintf(stdprn,"%4.2f\n",data->ph);
                else{
                        if(data->ph == -2) fprintf(stdprn,"NA\n");
                        else fprintf(stdprn,"QNS\n");
```

```c
        }
        fprintf(stdprn,"     pCO2:    ");
        if(data->pco2 > 0.0) fprintf(stdprn, "%5.1f    mmHg\n",data->pco2);
        else{
                if(data->pco2 == -2) fprintf(stdprn,"NA\n");
                else fprintf(stdprn,"QNS\n");
        }
        fprintf(stdprn,"     pO2:     ");
        if(data->po2 > 0.0) fprintf(stdprn,"%5.1f    mmHg\n",data->po2);
        else{
                if(data->po2 == -2) fprintf(stdprn,"NA\n");
                else fprintf(stdprn,"QNS\n");
        }
}
/*
        print Lytes + Gluc if requested
*/
if(strcmp(data->profile, "Blood gas")){
        fprintf (stdprn,"     Hct:     ");
        if(data->hct > 0.0) fprintf(stdprn, "%3.0f     %\n",data->hct);
        else{
                if(data->hct == -2) fprintf(stdprn,"NA\n");
                else fprintf(stdprn,"QNS\n");
        }
        fprintf (stdprn,"     Na:      ");
        if(data->na > 0.0) fprintf(stdprn, "%4.0f     mmol/L\n",data->na);
        else{
                if(data->na == -2) fprintf(stdprn,"NA\n");
                else fprintf(stdprn,"QNS\n");
        }
        fprintf (stdprn,"     K:       ");
        if(data->k > 0.0) fprintf(stdprn, "%4.1f    mmol/L\n",data->k);
        else{
                if(data->k == -2) fprintf(stdprn,"NA\n");
                else fprintf(stdprn,"QNS\n");
        }
        fprintf (stdprn,"     Cl:      ");
        if(data->cl > 0.0) fprintf(stdprn, "%4.0f     mmol/L\n",data->cl);
        else{
                if(data->cl == -2) fprintf(stdprn,"NA\n");
                else fprintf(stdprn,"QNS\n");
        }
        fprintf (stdprn,"     Ca++:    ");
        if(data->ca > 0.0) fprintf(stdprn, "%5.2f    mmol/L\n",data->ca);
        else{
                if(data->ca == -2) fprintf(stdprn,"NA\n");
                else fprintf(stdprn,"QNS\n");
        }
        fprintf (stdprn,"     Glucose:");
        if(data->gluc > 0.0) fprintf(stdprn, "%4.0f     mg/dl\n",data->gluc);
        else{
                if(data->gluc == -2) fprintf(stdprn,"NA\n");
                else fprintf(stdprn,"QNS\n");
        }
/*
        fprintf (stdprn,"     Lactate: ");
        if(data->lac > 0.0) fprintf(stdprn, "%3.1f    mmol/L\n\n",data->lac);
        else{
                if(data->lac == -2) fprintf(stdprn,"NA\n");
                else fprintf(stdprn,"QNS\n");
        }
*/
}
fprintf (stdprn,"Patient temp:  %4.1f %cC\n", data->temp, 0xf8);
fprintf (stdprn,"FiO2:          ");
if(data->fio2 == -1) fprintf(stdprn,"NFG\n");
else fprintf(stdprn, "%d\n", data->fio2);
pt.ph = data->ph;
pt.pco2 = data->pco2;
pt.po2 = data->po2;
```

```
1     pt.ca = data->ca;
      pt.hct = data->hct;
2     pt.temp = data->temp;
      temp_correct(&pt);
3     /*
              print temp corrected if requested
4     */
      if(strcmp(data->profile, "Elec/Glu/Lac")){
5             if (data->temp != 37.0) {
                      fprintf (stdprn, "\n\n%c%c%c%c%c%c",0x1b,0x34,0x1b,0x2d,0x31);
6                     fprintf (stdprn,"Temperature Correction: %4.1f %cC\n\n",
                                                                      data->temp, 0xf8);
7                     fprintf (stdprn, "%c%c%c%c%c%c",0x1b,0x35,0x1b,0x2d,0x30);
                      fprintf (stdprn,"pH:       ");
8                     if(data->ph > 0.0) fprintf(stdprn, "%4.2f\n", pt.ph);
                      else{
9                             if(data->ph == -2) fprintf(stdprn,"NA\n");
                              else fprintf(stdprn,"QNS\n");
10                    }
                      fprintf (stdprn,"pCO2: ");
11                    if(data->pco2 > 0.0) fprintf(stdprn, "%5.1f  mmHg\n", pt.pco2);
                      else{
12                            if(data->pco2 == -2) fprintf(stdprn,"NA\n");
                              else fprintf(stdprn,"QNS\n");
13                    }
                      fprintf (stdprn,"pO2:  ");
14                    if(data->po2 > 0.0) fprintf(stdprn, "%5.1f  mmHg\n", pt.po2);
                      else{
15                            if(data->po2 == -2) fprintf(stdprn,"NA\n");
                              else fprintf(stdprn," ONS\n");
16                    }
              }
17    }
      /*
18            print calculated results if requested
      */
19    if(strcmp(data->profile, "Elec/Glu/Lac")){
              calculated_results(&pt, cal);
20            fprintf (stdprn, "%c%c%c%c%c%c",0x1b,0x2d,0x31,0x1b,0x34);
              fprintf (stdprn,"\nCalculated Values\n\n");
21            fprintf (stdprn, "%c%c%c%c%c%c",0x1b,0x2d,0x30,0x1b,0x35);
              if(data->ph > 0.0){
22                    if(data->pco2 > 0.0){
                              if(data->hct > 0.0)
23                                    fprintf (stdprn,"BE_b:   %5.1f mmol/L\n",cal->be_b);
                              fprintf (stdprn,"Hco3:   %5.1f  mmol/L\n",cal->hco3);
24                            fprintf (stdprn,"Tco2:   %5.1f  mmol/L\n",cal->tco2);
                              if(data->po2 > 0.0)
25                                    fprintf (stdprn,"O2sat:  %5.1f  %\n",cal->o2sat);
                              if(data->po2 > 0.0 && data->hct > 0.0)
26                                    fprintf (stdprn,"O2ct:   %5.1f  ml/dl\n",cal-
      >o2ct);
27                    }
                      else{
28                            fprintf (stdprn,"BE_b:   N/A\n");
                              fprintf (stdprn,"Hco3:   N/A\n");
29                            fprintf (stdprn,"Tco2:   N/A\n");
                              fprintf (stdprn,"O2sat:  N/A\n");
30                            fprintf (stdprn,"O2ct:   N/A\n");
                      }
31            if((strcmp(data->profile, "Blood gas")) &&
                              (strcmp(data->profile, "Elec/Glu/Lac"))){
32                    if(data->ca > 0.0)
                              fprintf (stdprn,"nCa:    %5.1f  mmol/L\n",cal->nca);
33                    else
                              fprintf (stdprn,"nCa:    N/A\n");
34            }
              }
35    }
      if(strcmp(data->profile, "Elec/Glu/Lac")){
```

```
           if(data->hct > 0.0)
                       fprintf (stdprn,"hb:     %5.1f  g/dl\n",cal->hb);
                else
                       fprintf (stdprn,"hb:     N/A\n");
           }
           fprintf (stdprn,"\n\n\n\n\n\n\n");
           return(prn_status);
}
/*
           NAME:       nova_scrn - assigns screen numbers to nova displays
           INPUT:      screen buffer
                       scrn_id
           RETURN:     scrn_id
*/
nova_scrn(char *scrn_buf, char *scrn_id)
{
           strcpy(scrn_id, "*******");
           if (strstr(scrn_buf, "SENSOR STATUS")){
                       scrn_id[0] = 'S';
                       scrn_id[1] = '1';
           }
           else if (strstr(scrn_buf, "AIR DETECTOR STATUS")){
                       scrn_id[0] = 'S';
                       scrn_id[1] = '2';
           }
           else if (strstr(scrn_buf, "SEQUENCE ERRORS")){
                       scrn_id[0] = 'S';
                       scrn_id[1] = '3';
           }
           else if (strstr(scrn_buf, "SYSTEM ERRORS")){
                       scrn_id[0] = 'S';
                       scrn_id[1] = '4';
           }
           else if (strstr(scrn_buf, "SYSTEM STATUS")){
                       scrn_id[0] = 'S';
                       scrn_id[1] = '5';
           }
}
/*
           NAME:       nova_screen_reset - returns to ready/not ready screen
           INPUT:      screen buffer
           RETURN:     none
*/
nova_screen_reset()
{
           do{
                       if(strstr(scrn_buf, "READY FOR ANALYSIS")) return;
                       else if(strstr(scrn_buf, "NOT READY")) return;
                       else if(strstr(scrn_buf, "Press CLEAR to Abort")) return;
                       else{
                                  outportb(0x3f8, 0x7f);
                                  delay(200);
                       }
           } while(1);
}
/*
           NAME:       open_touch - opens the touch handle for use
           INPUT:      none
           RETURN:     none
*/
open_touch()
{
           char inbuf[0x20];
           int    handle;

if((handle = open("TCH_SCRN", O_BINARY|O_RDWR, S_IWRITE)) == -1)
           return(0);
           touch(handle, "reset", inbuf);
           return(handle);
}
```

```
1   /*
        NAME:       previous_files - concatenates strings that describe previous file names
2                                     finds previous patient results for give day
        INPUT:      data structure
3                   previous_data structure
        RETURN:     previous_data structure loaded with day names
4   */
    previous_files(DATA *data, DATA *previous_data){
5       char    string_time[26], date[5][25];
        time_t  long_time;
6       int     exist = 0, day, n;
        TABLEHANDLE prev_tables[5];
7       time(&long_time);
        long_time -= 86400L;
8       strcpy(string_time, ctime(&long_time));
        strcpy(date[0], "h:\\db\\");
9       strncat(date[0], &string_time[4],3);
        date[0][11] = '\0';
10      strncat(date[0], &string_time[8],2);
        n = PXTblExist(date[0], &exist);
11      if(n) printf("\nPXTblExist had error: %d\n", n);
        else {
12          if(exist) day = 1;
                else day = 2;
13      }
        for(n = 0; n < 6; n++) {
14          time(&long_time);
            long_time -= (86400L * day++);
15          strcpy(string_time, ctime(&long_time));
            strcpy(date[n], "h:\\db\\");
16          strncat(date[n], &string_time[4],3);
            date[n][11] = '\0';
17          strncat(date[n], &string_time[8],2);
        }
18      for(n = 0; n < 6; n++){
            PXTblExist(date[n], &exist);
19          if(exist){
                /*
20                  open previous days database and search for patient
                */
21              PXTblOpen(date[n], &prev_tables[n], 0, 0);
                if(search_and_display(prev_tables[n], data, previous_data, 0)){
22                  PXTblClose(prev_tables[n]);
                    break;
23              }
                PXTblClose(prev_tables[n]);
24          }
            prev_tables[n] = 0;
25      }
        return(0);
26  }
    /*
27      NAME:       print_previous_results - print the previous results for the selected
    patient up to 10
28      INPUT:      data structure
        RETURN:     none
29  */
    print_previous_results(DATA *data, CALCULATED *cal)
30  {
        struct date date;
31      struct time dtime;

32      DATA            *pt;
        int prn_status, i = 1;
33      /*
            test printer
34      */
        if((prn_status = printer_status()) != 0x90) return(prn_status);
35      pt = data;
        gettime(&dtime);
```

```
    getdate(&date);
    fprintf(stdprn,"University of Virginia Medical Center\n");
    fprintf(stdprn, "Charlottesville, Virginia\n");
    fprintf(stdprn, "Remote Standalone System\n\n");
    fprintf (stdprn,"Report Time:     %02d/%02d/%d        %02d:%02d:%02d\n",
             date.da_mon, date.da_day, date.da_year,
                 dtime.ti_hour, dtime.ti_min, dtime.ti_sec);
    fprintf (stdprn,"Patient name:    ");
    fprintf (stdprn,"%c%c",0x1b,0x45);
    fprintf (stdprn,"%s\n", pt->pat);
    fprintf (stdprn,"%c%c",0x1b,0x46);
    fprintf (stdprn,"SSN:            %s\n", pt->ssn);
    fprintf (stdprn,"Location:       %s\n\n", pt->devloc);
        fprintf (stdprn,"%c%c",0x1b,0x45);
        fprintf (stdprn,"     pH     pCO2     pO2     Hct\n");
        fprintf (stdprn,"%c%c",0x1b,0x46);
        fprintf (stdprn,"            mmHg     mmHg    %%\n\n");
        while(*pt->string_time && i < 10) {
                temp_correct(pt);
                fprintf (stdprn, "%d   ", i++);
                /*
                        print ph, poc2, po2 if requested
                */
                if(!strcmp(pt->status, "ACCEPT")){
                        if(strcmp(pt->profile, "Elec/Glu/Lac")){
                                if(pt->ph > 0.0){
                                        fprintf(stdprn,"%4.2f   ", pt->ph);
                                }
                                else {
                                        if(pt->ph == -2) fprintf(stdprn," NA    ");
                                        else fprintf(stdprn," QNS   ");
                                }
                                if(pt->pco2 > 0.0){
                                        fprintf (stdprn,"%5.1f   ", pt->pco2);
                                }
                                else {
                                        if(pt->pco2 == -2) fprintf(stdprn," NA    ");
                                        else fprintf(stdprn," QNS   ");
                                }
                                if(pt->po2 > 0.0){
                                        fprintf (stdprn,"%5.1f  ", pt->po2);
                                }
                                else {
                                        if(pt->po2 == -2) fprintf(stdprn," NA    ");
                                        else fprintf(stdprn," QNS   ");
                                }
                                /*
                                        print Lytes + Gluc if requested
                                */
                                if(strcmp(pt->profile, "Blood gas"))
                                        if(pt->hct > 0.0){
                                                fprintf (stdprn," %3.0f\n", pt->hct);
                                        }
                                        else {
                                                if(pt->hct == -2) fprintf(stdprn," NA    ");
                                                else fprintf(stdprn," QNS   ");
                                        }
                                else{
                                        fprintf(stdprn,"45.0\n");
                                }
                        }
                        else{
                                fprintf(stdprn,">\n");
                        }
                }
                else{
                        if(!strcmp(pt->status, "DONE")){
                                fprintf(stdprn, "PENDING Tech Review\n");
                        }
```

```
        else if(!strcmp(pt->status, "FAIL")){
                fprintf(stdprn, "FAILED by Tech call the Lab\n");
        }
    }
    pt++;
}
fprintf (stdprn,"\n\n%c%c",0x1b,0x45);
fprintf (stdprn,"     Na+     K+      Cl-      Ca++\n");
fprintf (stdprn,"%c%c",0x1b,0x46);
fprintf (stdprn," mmol/L  mmol/L  mmol/L   mmol/l\n\n");
i = 1;
pt = data;
while(*pt->string_time && i < 10) {
        fprintf (stdprn, "%d  ", i++);
        /*
                print Lytes + Gluc if requested
        */
        if(!strcmp(pt->status, "ACCEPT")){
                if(strcmp(pt->profile, "Blood gas")){
                        if(pt->na > 0.0){
                                fprintf (stdprn,"%4.0f    ", pt->na);
                        }
                        else {
                                if(pt->na == -2) fprintf(stdprn," NA   ");
                                else fprintf(stdprn," QNS  ");
                        }
                        if(pt->k > 0.0){
                                fprintf (stdprn,"%4.1f    ", pt->k);
                        }
                        else {
                                if(pt->k == -2) fprintf(stdprn," NA   ");
                                else fprintf(stdprn," QNS  ");
                        }
                        if(pt->cl > 0.0){
                                fprintf (stdprn,"%5.1f    ", pt->cl);
                        }
                        else {
                                if(pt->cl == -2) fprintf(stdprn," NA   ");
                                else fprintf(stdprn," QNS  ");
                        }
                        if(pt->ca > 0.0){
                                fprintf (stdprn,"  %5.2f", pt->ca);
                        }
                        else {
                                if(pt->ca == -2) fprintf(stdprn," NA   ");
                                else fprintf(stdprn," QNS  ");
                        }
                }
        }
        fprintf(stdprn, "\n");
        pt++;
}
fprintf (stdprn,"%c%c",0x1b,0x45);
fprintf (stdprn,"\n\n   Gluc    Lac      Fio2    SAMPLE #\n");
fprintf (stdprn,"%c%c",0x1b,0x46);
fprintf(stdprn,"    mg/dl  mmol/L    %%\n\n");
pt = data;
i = 1;
while(*pt->string_time && i < 10) {
        fprintf (stdprn,"%d  ", i++);
        /*
                print Lytes + Gluc if requested
        */
        if(!strcmp(pt->status, "ACCEPT")){
                if(strcmp(pt->profile, "Blood gas")){
                        if(pt->gluc > 0.0){
                                fprintf (stdprn,"%4.0f    ", pt->gluc);
                        }
                        else {
                                if(pt->gluc == -2) fprintf(stdprn," NA   ");
```

```
                                        else fprintf(stdprn," QNS  ");
                                }
                        }
                        else{
                                fprintf (stdprn,"           ");
                        }
        /*
                        if(pt->lac > 0.0){
                                fprintf (stdprn,"%4.1f  ", pt->lac);
                        }
                        else {
                                if(pt->lac == -2) fprintf(stdprn," NA   ");
                                        else fprintf(stdprn," QNS  ");
                        }
        */
                        if(pt->fio2 <= 0.0) fprintf (stdprn," NFG    ");
                        else    fprintf (stdprn," %d    ", pt->fio2);
                        fprintf (stdprn," %ld", pt->sn);
                }
                fprintf(stdprn, "\n");
                pt++;
        }
                        fprintf (stdprn,"\n\n   %c%c  Be-b    Hco3    Tco2%c%c\n",
0x1b,0x45,0x1b,0x46);
                        fprintf (stdprn,"     mmol/L  mmol/L  mmol/L\n\n");
                        pt = data;
                        i = 1;
                while(*pt->string_time && i < 10) {
                        calculated_results(pt, cal);
                        fprintf (stdprn,"%d", i++);
                        /*
                                print ph, pco2, po2 if requested
                        */
                        if(!strcmp(pt->status, "ACCEPT")){
                                if(strcmp(pt->profile, "Elec/Glu/Lac")){
                                        if(data->ph && data->pco2 && data->hct)
                                                fprintf (stdprn,"   %5.1f", cal->be_b);
                                        else
                                                fprintf (stdprn," N/A   ");
                                        if(data->ph && data->pco2)
                                                fprintf (stdprn,"   %5.1f", cal->hco3);
                                        else
                                                fprintf (stdprn," N/A   ");
                                        if(data->ph && data->pco2)
                                                fprintf (stdprn,"   %5.1f\n", cal->tco2);
                                        else
                                                fprintf (stdprn," N/A   ");
                                }
                        }
                        fprintf(stdprn, "\n");
                        pt++;
                }
                fprintf(stdprn,"\n\n%c%c   O2sat   O2ct    nCa     Hb%c%c\n",
                                0x1b,0x45,0x1b,0x46);
                fprintf (stdprn,"    %%      ml/dl   mmol/L  g/dl\n\n");
                pt = data;
                i = 1;
                while(*pt->string_time && i < 10) {
                        fprintf (stdprn, "%d", i++);
                        /*
                                print calculated values if requested
                        */
                        if(!strcmp(pt->status, "ACCEPT")){
                                if(strcmp(pt->profile, "Elec/Glu/Lac")){
                                        calculated_results(pt, cal);
                                        if(data->ph && data->pco2 && data->po2)
                                                fprintf (stdprn,"   %5.1f", cal->o2sat);
                                        else
                                                fprintf (stdprn," N/A");
```

```
                        if(data->ph && data->pco2 && data->po2 && data->hct)
                                fprintf (stdprn,"    %5.1f", cal->o2ct);
                        else
                                fprintf (stdprn,"     N/A");
                }
                if((strcmp(pt->profile, "Blood gas")) &
                        (strcmp(pt->profile, "Elec/Glu/Lac"))){
                        if(data->ph && data->ca)
                                fprintf (stdprn,"    %5.1f", cal->nca);
                        else
                                fprintf (stdprn,"     N/A");
                }
                else{
                        fprintf (stdprn,"          ");
                }
                if(strcmp(pt->profile, "Elec/Glu/Lac")){
                        if(data->hct)
                                fprintf (stdprn,"    %5.1f\n", cal->hb);
                        else
                                fprintf (stdprn,"     N/A");
                }
        }
        fprintf(stdprn, "\n");
        pt++;
    }
    fprintf(stdprn,"\n\n%c%c  Run Time      Run Date       Type%c%c\n\n",
                        0x1b,0x45,0x1b,0x46);
    pt = data;
    i = 1;
    while(*pt->string_time && i < 10) {
            fprintf (stdprn, "%d  ", i++);
            fprintf (stdprn,"%-10s ",&pt->string_time);
            fprintf (stdprn,"  %d/%d/%d   ",pt->month, pt->day, pt->year);
            pt->type ? fprintf(stdprn," Arterial\n"):
                                                    fprintf(stdprn,"  Venous\n");
            pt++;
    }
    fprintf (stdprn,"\n\n\n\n\n\n\n");
    calculated_results(data, cal);
    return(prn_status);
}
/*
        NAME:       printer_status - checks printer for operation
                                 alerts user to possible error
        INPUT:      none
        RETURN:     0 if OK
                    1 if errored
*/
printer_status()
{
int printer_status;
    printer_status = biosprint(2,' ',0);
    if (printer_status != 0x90) {
            /*
                        alert user to error
            */
            gotoxy(10,1);
            textcolor(LIGHTRED|BLINK);
            textbackground(BLACK);
            cprintf("Printer Error - %x", printer_status);
            textcolor(LIGHTRED);
            cprintf("  Check printer function - retry print or escape");
            textcolor(BLACK);
            textbackground(LIGHTGRAY);
    }
    else {
            textcolor(LIGHTGRAY);
            textbackground(BLACK);
            gotoxy(10,1);
            clreol();
```

```
        }
        textcolor(BLACK);
        textbackground(LIGHTGRAY);
        return(printer_status);
}
/*
        NAME:     put_results_into_database - puts measured and collected data into
the uva_raw database
        INPUT:    results database
                  data structure
                  sequence number
        RETURN:   none
*/
put_results_into_database(RESULTS_DATA *results, DATA *data, long count)
{
        TABLEHANDLE     tblhdl;
        RECORDHANDLE    rechdl;
        struct date dt;
        long date;
        PXTblOpen("h:\\db\\uva_raw", &tblhdl, 0, 0);
        PXRecBufOpen(tblhdl, &rechdl);
        PXPutAlpha(rechdl, 1, data->pat);
        PXPutAlpha(rechdl, 2, data->ssn);
        PXPutAlpha(rechdl, 3, data->unit);
        PXPutAlpha(rechdl, 4, data->access);
        PXPutLong(rechdl, 5, count);
        PXPutDoub(rechdl, 6, results->bp);
        PXPutDoub(rechdl, 7, data->temp);
        PXPutDoub(rechdl, 8, results->ph);
        PXPutDoub(rechdl, 9, results->pco2);
        PXPutDoub(rechdl, 10, results->po2);
        PXPutDoub(rechdl, 11, results->hct);
        PXPutDoub(rechdl, 12, results->na);
        PXPutDoub(rechdl, 13, results->k);
        PXPutDoub(rechdl, 14, results->cl);
        PXPutDoub(rechdl, 15, results->ca);
        PXPutDoub(rechdl, 16, results->gluc);
        PXPutShort(rechdl, 17, data->type);
        PXPutShort(rechdl, 18, data->fio2);
        PXPutAlpha(rechdl, 19, "TCVPO");
        pxtime(&ttime);
        getdate(&dt);
        PXDateEncode(dt.da_mon, dt.da_day, dt.da_year, &date);
        PXPutDate(rechdl, 20, date);
        PXPutAlpha(rechdl, 21, ttime.time);
        PXPutAlpha(rechdl, 23,"DONE");
        PXPutAlpha(rechdl, 25, test_sel[data->test_select]);
        PXPutAlpha(rechdl, 26, data->errors);
  /*    PXPutDoub(rechdl, 27, results->lac);*/
        PXRecAppend(tblhdl, rechdl);
        PXRecBufClose(rechdl);
        PXTblClose(tblhdl);
}
/*
        NAME:     pxtime - converts seconds into a time for the database
        INPUT:    ttime structure
        RETURN:   time string in ttime structure
*/
long pxtime(TTIME *ttime)
{
        char temp[4];
        long total;
        gettime(&ttime->dtime);
        memset(ttime->time, '\0', 10);
        itoa(ttime->dtime.ti_hour, temp, 10);
        if(ttime->dtime.ti_hour < 10){
                strcpy(ttime->time, "0");
                strcat(ttime->time, temp);
        }
        else{
```

```c
            strcpy(ttime->time, temp);
    }
    strcat(ttime->time,":");
    itoa(ttime->dtime.ti_min, temp, 10);
    if(ttime->dtime.ti_min < 10){
            strcat(ttime->time, "0");
    }
    strcat(ttime->time, temp);
    strcat(ttime->time,":");
    itoa(ttime->dtime.ti_sec, temp, 10);
    if(ttime->dtime.ti_sec < 10){
            strcat(ttime->time, "0");
    }
    strcat(ttime->time, temp);
    total = (ttime->dtime.ti_hour * 3600l) +
                         (ttime->dtime.ti_min * 60) +
                                    ttime->dtime.ti_sec;
    return(total);
}
/*
    NAME:       rec_irq_enable - set nova irq vector and enable comm port UART
    INPUT:      none
    RETURN:     none
*/
rec_irq_enable()
{
    unsigned status;
    disable();
    setvect(0x0c, irq_func);
    enable();
    status = inportb(0x3fc);
    outportb(0x3fc, status | 0x0b);
    status = inportb(0x3f9);
    outportb(0x3f9, status | 0x01);
    status = inportb(0x21);
    outportb(0x21, status & 0xE0);
}
/*
    NAME:       rec_irq_disable - disable comm port nova irq
    INPUT:      none
    RETURN:     none
*/
rec_irq_disable()
{
    int status;
    status = inportb(0x21);
    outportb(0x21, status | 0x10);
    status = inportb(0x3fc);
    outportb(0x3fc, status | 0xfc);
}
/*
    NAME:       results_screen - displays current results and allows user to view previ-
ous results or print
    INPUT:      data structure
                sequence number
    RETURN:     none
*/
results_screen(int handle, DATA *data, CALCULATED *cal, long count)
{
    char    entry[0x10], temp_status[10];
    int     function_choice, x = 1, exit = 1;
    DATA                previous_data[10];
    puts("\377\377cal_res/");
    puts("\377\377csc/");
    touch(handle,"group all off",entry);
    touch(handle,"group 12 on",entry);
    status_check(cal, data, count);
    strcpy(temp_status, data->status);
    do{
            if(touch_choice('F', entry, handle))        return(0);
```

```
switch(entry[2]){
    case 'P':
        /*
            print results
        */
        beep(440);
        if(!strcmp(data->status, "ACCEPT")) nova_print(data, cal);
        else{
            gotoxy(30, 20);
            textcolor(LIGHTRED|BLINK);
            cprintf("Cannot print results");
            textcolor(LIGHTGRAY);
        }
        break;
    case 'X':
        /*
            escape
        */
        beep(700);
        function_choice = 0;
        x = 0;
        break;
    case 'R':
        /*
            previous results display
        */
        beep(800);
        display_previous_results(data, previous_data);
        touch(handle, "group all off", entry);
        touch(handle, "group 13 on", entry);
        do{
            if(touch_choice('F', entry, handle)) return(0);
            switch(entry[2]){
                case 'P':
                    /*
                        print previous results
                    */
                    beep(440);
                    print_previous_results(previous_data, cal);
                    exit = 1;
                    break;
                case 'X':
                    /*
                        escape
                    */
                    beep(700);
                    exit = 0;
            }
        } while(exit);
        /*
            redisplay results
        */
        puts ("\377\377cal_res/");
        puts("\377\377esc/");
        touch(handle, "group all off", entry);
        touch(handle, "group 12 on", entry);
        strcpy(data->status, temp_status);
        status_check(cal, data, count);
        break;
}
} while (x);
return(function_choice);
}
/*
    NAME:    role - gets the list of valid patients for selected unit
                    selected desired patient
    INPUT:   demographics structure
    RETURN:  demo structure loaded with selected patient demo's
*/
```

```
1    role(int handle, DATA *data, DEMOGRAPHICS *pat_rec)
     {
2        int dsplyend, window_end, record_begin, window_begin, record_end;
         int send_this_back, counter, bar;
3        int exit = 0, freq = 0, patient_num = 0;
         char entry[0x10];
4        TABLEHANDLE    tblhdl;
         RECORDHANDLE   rechdl;
5        /*
                 search for selected unit patients
6        */
         PXTblOpen("h:\\db\\uva_pats", &tblhdl, 0, 0);
7        PXRecBufOpen(tblhdl, &rechdl);
         PXPutAlpha(rechdl, 1, data->unit);
8        if(!PXSrchFld(tblhdl, rechdl, 1, SEARCHFIRST)){
                 PXRecGet(tblhdl, rechdl);
9                /*
                         get name, history #
10               */
                 PXGetAlpha(rechdl, 2, 20, (pat_rec + patient_num)->nme);
11               PXGetAlpha(rechdl, 5, 10, (pat_rec + patient_num)->ssn);
                 patient_num++;
12               /*
                         get next patient
13               */
                 while(!PXSrchFld(tblhdl, rechdl, 1, SEARCHNEXT)){
14                       PXRecGet(tblhdl, rechdl);
                         PXGetAlpha(rechdl, 2, 20, (pat_rec + patient_num)->nme);
15                       PXGetAlpha(rechdl, 5, 10, (pat_rec + patient_num)->ssn);
                         patient_num++;
16               }
         }
17       PXRecBufClose(rechdl);
         PXTblClose(tblhdl);
18       window_begin = record_begin = bar = counter = 0;
         record_end = patient_num;
19       dsplyend = window_end = 15;
         if(!patient_num){
20               sa_stat(LIGHTRED|BLINK, "No Patients in selected Unit");
                 beep(1000);
21               beep(500);
                 sleep(2);
22               return(2);
         }
23       else{
                 /*
24                       select patient from roster
                 */
25               touch(handle, "group all off", entry);
                 sa_scrn(YELLOW, "Patient Select", LIGHTRED, "Scroll to desired Patient");
26               puts("\377\377updwn/");
                 puts("\377\377esc/");
27               touch(handle, "group 6 on", entry);
                 touch(handle, "group 15 on", entry);
28               gotoxy(65, 3);
                 textcolor(YELLOW);
29               cprintf("%s", data->unit);
                 roledsp(record_begin, dsplyend, record_end, bar, pat_rec);
30       }
         do{
31               if(touch_choice('R', entry, handle)) return(2);
                 switch(entry[2]){
32               case 'D':
                         /*
33                               scroll down
                         */
34                       freq = 680;
                         if(counter >= record_end - 1)      beep(550);
35                       else{
                                 if(counter++ > window_end - 1){
```

```
                                        window_begin++;
                                        window_end++;
                                }
                                bar++ ;
                                roledsp(window_begin,window_end,record_end,bar,pat_rec);
                        }
                        break;
                case 'H':
                        /*
                                history search
                        */
                        beep(550);
                        return(4);
                case 'U':
                        /*
                                scroll up
                        */
                        freq = 700;
                        if(counter <= 0) beep(550);
                        else{
                                if(counter-- <= window_begin){
                                        window_begin--;
                                        window_end--;
                                }
                                bar--;
                                roledsp(window_begin, window_end, record_end, bar, pat_rec);
                        }
                        break;
                case '!':
                        /*
                                enter
                        */
                        beep(800);
                        strcpy(data->pat, (pat_rec + bar)->nme);
                        strcpy(data->ssn, (pat_rec + bar)->ssn);
                        send_this_back = 6;
                        exit = 1;
                        break;
                case 'X':
                        /*
                                escape
                        */
                        beep(800);
                        send_this_back = 0;
                        exit = 1;
                        break;
                }
                if(freq){
                        sound(freq);
                        delay(200);
                        nosound();
                        freq = 0;
                }
        } while (!exit);
        return (send_this_back);
}
/*
        NAME:       roledsp - displays list of patient for selected unit
        INPUT:      bar location
                    start (b) and stop (e) if list
                    demographics structure with data
        RETURN:     none
*/
roledsp(int b,int e,int recend,int bar,DEMOGRAPHICS *pat_rec)
{
        int x, count = 0, row = 6;
        for (x = b; x <= e; x++){
                if(x == bar) textcolor (YELLOW);
                else textcolor(LIGHTGRAY);
```

```
                if(count++ > recend - 1) break;
                gotoxy(5, row++);
                cprintf("  %-20s    %-10s",(pat_rec + x)->nme,(pat_rec + x)->ssn);
        }
}
/*
        NAME:       sa_hdr - sa header displays text centered in box
        INPUT:      color to display text
                    string pointer
        RETURN:     none
*/
sa_hdr(int hdr_color, char *hdr)
{
        int length;
        length = strlen(hdr);
        textcolor(hdr_color);
        puts("\377\377 sa_hdr/");
        gotoxy(30 - length/2, 3);
        cprintf(hdr);
}
/*
        NAME:       sa_stat - displays sa status as a line of text
        INPUT:      st_color of text
                    status pointer
        RETURN:     none
*/
sa_stat(int st_color, char *status)
{
        int length;
        length = strlen(status);
        textcolor(st_color);
        puts("\377\377 sa_stat/");
        gotoxy(27 - length/2, 23);
        cprintf(status);
}
/*
        NAME:       sa_scrn - displays sa screen with header and status
        INPUT:      header & status color
                    header & status char pointers
        RETURN:     none
*/
sa_scrn(int hdr_color, char *hdr, int st_color, char *status)
{
        textbackground(BLACK);
        clrscr();
        sa_hdr(hdr_color, hdr);
        sa_stat(st_color, status);
}
/*
        NAME:       save_unit - puts last requested unit into the uva_acc.db
        INPUT:      data structure
        RETURN:     unit loaded to db
*/
save_unit(DATA *data)
{
        PIC_DATA    pic;
        TABLEHANDLE     tblhdl;
        RECORDHANDLE    rechdl;
        strcpy(pic.access, data->access);
        PXTblOpen("h:\\db\\uva_acc", &tblhdl, 0, 0);
        PXRecBufOpen(tblhdl, &rechdl);
        /*
                find user in db
        */
        if(search_access(tblhdl, rechdl, &pic) != PXSUCCESS){
                PXRecBufClose(rechdl);
                PXTblClose(tblhdl);
                return(1);
        }
        PXRecGet(tblhdl, rechdl);
```

```
                PXPutAlpha(rechdl, 6, data->unit);
                PXRecUpdate(tblhdl, rechdl);
                PXRecBufClose(rechdl);
                PXTblClose(tblhdl);
                return(0);
        }
        /*
                NAME:      scrn_save - puts to screen messages for user help and protects screen
                INPUT:     none
                RETURN:    none
        */
        scrn_save(int handle)
        {
                int x, y;
                static time_t last_ti = 0;
                time_t ti;
                char *notes[] = {"*** SA System Idle ***",
                                        "Minimum Sample Volume - 0.5 ml",
                                        "Need Help? - call the Lab", NULL};
                int status_colors[] = {LIGHTRED, YELLOW, LIGHTGREEN, LIGHTCYAN,
                                        LIGHTBLUE, LIGHTMAGENTA, WHITE};
                if(time(&ti) > last_ti + 1){
                        time(&last_ti);
                        window(1, 1, 80, 25);
                        clrscr();
                        gotoxy((x = random(40) + 1), (y = random(22) + 1));
                        textcolor(status_colors[(random(40) + 1) % 6]);
                        cprintf(notes[abs((int)last_ti%3)]);
                        if(!handle){
                                gotoxy(x, y + 1);
                                cprintf("Press any key to activate system");
                        }
                }
        }
        /*
                NAME:      search_access - search uva_acc.db for valid access code
                INPUT:     open table handle
                           open table record handle
                           pic_data structure with access code
                RETURN:    0 if OK
                           1 if not
        */
        search_access(TABLEHANDLE tblhdl, RECORDHANDLE rechdl, PIC_DATA *pic_data)
        {
                PXPutAlpha(rechdl, 1, pic_data->access);
                if(PXSrchFld(tblhdl, rechdl, 1, SEARCHFIRST) != PXSUCCESS) return(1);
                return(0);
        }
        /*
                NAME:      search_and_display - searches selected database for specific history
        number
                                        displays previous patient data
                INPUT:     open table handle
                           open table record handle
                           data structure with patient demo's
                RETURN:    loads previous data structure
        */
        search_and_display(TABLEHANDLE tblhdl, DATA *data, DATA *previous_data, int
        re_zero){
                static int i = 0, row = 10;
                char temp_ssn[10];
                RECORDHANDLE rechdl;
                if(re_zero){
                        i = 0;
                        row = 10;
                }
                /*
                        start search at end of db
                */
                PXRecBufOpen(tblhdl, &rechdl);
```

```
1       PXRecLast(tblhdl);
        do{
2               PXRecGet(tblhdl, rechdl);
                PXGetAlpha(rechdl, 2, 10, temp_ssn);
3               if(!strcmp(data->ssn, temp_ssn)){
                        PXGetAlpha(rechdl, 23, 7, data->status);
4                       get_results(rechdl, &previous_data[i]);
                        /*
5                                display data or pending status
                        */
6                       switch(various_status(data->status)) {
                                case 0:
7                                       linear_display(&previous_data[i++], row++);
                                        break;
8                               case 1:
                                        gotoxy(1, row);
9                                       textcolor(LIGHTRED);
                                        cprintf(" Sample FAILED - call the Lab");
10                                      date_time(row++, &previous_data[i++]);
                                        textcolor(LIGHTGRAY);
11                                      break;
                                case 2:
12                                      gotoxy(1, row);
                                        textcolor(CYAN);
13                                      cprintf(" Pending review ");
                                        date_time(row++, &previous_data[i++]);
14                                      textcolor(LIGHTGRAY);
                                        break;
15                              default:
                                        break;
16                      }
                        if(i >= 10) return(1);
17              }
        } while(!PXRecPrev(tblhdl));
18
        PXRecBufClose(rechdl);
19      return(0);
}
20      /*
        NAME:       search_ssn - search uva_acc for valid history #
21      INPUT:      open table handle
                    open table record handle
22                  pic_data structure with patient demo's
        RETURN:     0 if OK
23                  1 if not
        */
24      search_ssn(TABLEHANDLE tblhdl, RECORDHANDLE rechdl, PIC_DATA *pic_data)
        {
25              PXPutAlpha(rechdl, 5, pic_data->access);
                if(!PXSrchFld(tblhdl, rechdl, 5, SEARCHFIRST)){
26                      PXRecGet(tblhdl, rechdl);
                        PXGetAlpha(rechdl, 1, 10, pic_data->access);
27                      PXGetAlpha(rechdl, 2, 10, pic_data->verify);
                        return(0);
28              }
                return(1);
29      }
        /*
30      NAME:       sequence_errors - retrieval routine for analyzer errors
                                placed in a string for database storage
31      INPUT:      screen buffer
                    scrn_id
32      RETURN:     error string loaded with errors
        */
33      sequence_errors(char *scrn_id, char *errors, char *scrn_buf)
        {
34              int         i, j, count;
                unsigned    char *temp_pt, *scrn_pos;
35              if(errors[0] == NULL){
                        errors[0] = '{';
```

```
1                errors[1] = NULL;
         }
2         outportb(0x3f8, 0x7f);
          delay(100);
3         /*
                 goto status screen
4         */
          for(i = 0, j = 0; i <= 2; i++){
5                outportb(0x3f8,'S');
                 do{
6                        nova_scrn(scrn_buf, scrn_id);
                         j++;
7                }while(scrn_id[1] != i+0x30 && j < 10);
          }
8         sleep(3);
          /*
9                get errors
          */
10        if((scrn_pos = strstr(scrn_buf, "Others")) != NULL){
                 scrn_pos += sizeof("Others") + 6;
11               temp_pt = scrn_pos;
                 for(count = 0; *scrn_pos++ == ' '; count++);
12               if(count <= 5){
                         while(*scrn_pos != ' '){
13                               strncat(errors, scrn_pos, 2);
                                 strcat(errors,"{");
14                               scrn_pos += 43;
                         }
15               }
                 strcat(errors,"}");
16               scrn_pos = temp_pt + 21;
                 for(count = 0; *scrn_pos++ == ' '; count++)
17                       ;
                 if(count <= 5){
18                       while(*scrn_pos != ' '){
                                 strncat(errors, scrn_pos, 2);
19                               strcat(errors,"}");
                                 scrn_pos += 43;
20                       }
                 }
21        }
          else return(1);
22        /*
                 return to ready
23        */
          outportb(0x3f8,0x7f);
24        delay(100);
          return(0);
25  }
    /*
26        NAME:      srch_prev_results - search previous results searches selected table for
    matching results
27        INPUT:     table name to search
                     data structure with history #
28        RETURN:    matching results in data structure
    */
29  srch_prev_results(char *tbl_name, DATA *data)
    {
30        TABLEHANDLE    tblhdl;
          RECORDHANDLE   rechdl;
31        char temp_ssn[10];
          PXTblOpen(tbl_name, &tblhdl, 0, 0);
32        PXRecBufOpen(tblhdl, &rechdl);
          PXRecLast(tblhdl);
33        do{
                 PXRecGet(tblhdl, rechdl);
34               PXGetAlpha(rechdl, 2, 10, temp_ssn);
                 if(!strcmp(data->ssn, temp_ssn)){
35                       PXGetAlpha(rechdl, 23, 7, data->status);
                         PXRecGet(tblhdl, rechdl);
```

```
                get_results(rechdl, data);
                PXRecBufClose(rechdl);
                PXTblClose(tblhdl);
                return(11);
            }
        } while(!PXRecPrev(tblhdl));
        PXRecBufClose(rechdl);
        PXTblClose(tblhdl);
        return(0);
}
/*
        NAME:       check_status - checks status of the results and displays appropriate response
        INPUT:      sequence number
                    data structure
                    calculated structure
        RETURN:     none
*/
status_check(CALCULATED *cal, DATA *data, long count)
{
        if(!strcmp(data->status, "ACCEPT")) display_results(data, cal);
        else if(!strcmp(data->status, "DONE")){
                data_header(data, count);
                window(20, 7, 60, 20);
                clrscr();
                textcolor(CYAN);
                gotoxy(1, 5);
                cprintf("Results Pending Review by Technologist");
                textcolor(LIGHTGRAY);
                window(1, 1, 80, 25);
        }
        else if(!strcmp(data->status, "FAIL")){
                data_header(data, count);
                window(20, 7, 60, 20);
                clrscr();
                textcolor(LIGHTRED);
                gotoxy(1, 5);
                cprintf("Results Failed by Technologist\n\r");
                cprintf("         call the Lab");
                textcolor(LIGHTGRAY);
                window(1, 1, 80, 25);
        }
        return(0);
}
/*
        NAME:       tch_scale - set touch screen scale
        INPUT:      driver handle
                    pointer to scale size
        RETURN:     0 if OK
                    error otherwise
*/
tch_scale(int handle, char *scale)
{
        char    ibuf[0xff];
        int err;
        touch(handle, "init", ibuf);
        err = touch(handle, scale, ibuf);
        return(err);
}
/*
        NAME:       temp_correct - temperature correction routine
        INPUT:      data structure
        RETURN:     temperature corrected data in data structure
*/
temp_correct(DATA *data)
{
        double x, y, z;
        if(data->ph > 0.0) data->ph -= (0.015 * (data->temp - 37.0));
        if(data->pco2 > 0.0)
                data->pco2 = data->pco2 * pow(10, (0.019 * (data->temp - 37.0)));
```

```
1       if(data->po2 > 0.0){
                z = exp(3.88 * log(data->po2));
2               x = 5.49e-11 * z + 0.071;
                y = 9.72e-09 * z + 2.30;
3               data->po2 = data->po2 * exp(2.303 * (data->temp - 37.0) * x / y);
        }
4   }
    /*
5       NAME:       touch - interacts with the touch driver and keyboard to allow user in-
    put
6       INPUT:      touch driver handle
                    operation of function (str)
7       RETURN:     inbuf string from driver
    */
8   touch(int handle, char *str, char *inbuf)
    {
9       char    term[2] = {0x0d, NULL}, *pt;
        pt = inbuf;
10      if(bioskey(1)){
                strset(inbuf, 'F');
11              inbuf[2] = bioskey(0);
                if(inbuf[2] > 0x60) inbuf[2] = inbuf[2] & 0xdf;
12              return(1);
        }
13      else if(!handle){
                strcpy(inbuf, "  NONE");
14              return(0);
        }
15      if(write(handle, str, strlen(str)) == -1){
                perror("touch write");
16              close(handle);
                exit(0);
17      }
        if(write(handle, term, strlen(term)) == -1){
18              perror("touch write");
                close(handle);
19              exit(0);
        }
20      if(read(handle, inbuf, 0x20) == -1){
                perror("touch read");
21              close(handle);
                exit(0);
22      }
        while (*pt++ != 0x0d);
23      *pt = NULL;
        if (inbuf[0] == 'E'){
24              fprintf(stdprn, "ERROR - %s\n\t%s\n", str, inbuf);
                return(1);
25      }
        return(0);
26  }
    /*
27      NAME:       touch_choice - performs a time limited touch. If no response within
    given time
28                              a timeout occurs
        INPUT:      choice - f first, r repeat, l last
29                  touch handle
        RETURN:     entry buffer
30  */
    touch_choice(char choice, char *entry, int handle)
31  {
        time_t start_time, now_time;
32      do {
                time(&start_time);
33              do {
                        if(touch(handle, "mode pad", entry)){
34                              entry[0] = choice;
                        }
35                      if(time(&now_time) > (start_time + 30)) {
                                return(1);
```

```
                        }
        } while(entry[0] != choice);
} while(!(strncmp(&entry[2], "NONE", 4)));
/*
        delay if repeat touch
*/
if(choice == 'R') delay(200);
else delay(75);
return(0);
}
/*
        NAME:       various_status - check status of patient results
        INPUT:      status of results
        RETURN:     -1 if an error
                     0 accept
                     1 fail
                     2 done
*/
various_status(char *status){
        char status_number[3], *ptr;
        char various_status[] = {"ACCEPT  0 FAIL    1 DONE    2 "};
        ptr = strstr(various_status, status);
        if(*ptr){
                strncpy(status_number, (ptr + 8), 2);
                status_number[2] = NULL;
                return(atoi(status_number));
        }
        return(-1);
}
/*
        NAME:       verify_scrn - allows entry of the verify code
        INPUT:      pic_data structure
        RETURN:     verify code in pic_data structure
*/
verify_scrn(int handle, PIC_DATA *pic_data)
{
        char entry[0x10];
        int count = 0, row = 3, col = 65, length = 9;
        puts("\377\377 clr_hdr/");
        sa_hdr(YELLOW, "Enter Verification Number");
        textcolor(YELLOW);
        puts("\377\377 keys/");
        strset(pic_data->verify,'\0');
        do{
                if(touch_choice('F', entry, handle)) return(0);
                switch(entry[2]){
                        case '@':
                                /*
                                        clear
                                */
                                beep(850);
                                gotoxy(64, 3);
                                cprintf("         ");
                                col -= count;
                                count = 0;
                                strset (pic_data->verify, '\0');
                                break;
                        case '!':
                                /*
                                        enter
                                */
                                beep(800);
                                pic_data->verify[count] = NULL;
                                break;
                        default:
                                /*
                                        alphanumeric entry
                                */
                                beep(700);
                                if(count < length){
```

```
                        gotoxy(col++, row);
                        pic_data->verify[count++] = entry[2];
                        cprintf("*");
                }
                else beep(550);
                break;
            }
        } while(entry[2] != '!');
        return(0);
}
/*
        NAME:     view_results - searchs for selected unit and patient to display current
and previous data
        INPUT:    demo's structure
                  data structure
        RETURN:   next main case operation
*/
view_results(int handle, DEMOGRAPHICS *pat_rec, DATA *data, UNITS *units)
{
        char tbl[30];
        int choice;
        do{
                /*
                        get valid units
                */
                choice = wrole(handle, data, units);
                switch (choice){
                        case 0:
                                return(0);
                        case 3:
                                /*
                                        get valid patients
                                */
                                choice = role(handle, data, pat_rec);
                                if(!choice) return(0);
                                if(choice != 4) break;
                        case 4:
                                /*
                                        search by histroy #
                                */
                                choice = find_history_number(handle, data);
                                if(!choice) choice = 2;
                                break;
                }
        } while (choice == 2);
        /*
                search for previous data
        */
        if(!srch_prev_results( "h:\\db\\uva_raw", data)){
                if(yesterdays_date(tbl)){
                        if(srch_prev_results(tbl, data)) return(11);
                }
                no_sample_data(handle, data);
                return(0);
        }
        return(11);
}
/*
        NAME:     wrole - valid unit list displayed and allows a user selection of unit
        INPUT:    user input
        RETURN:   selected unit
*/
wrole(int handle, DATA *data, UNITS *unit)
{
        char entry[0x10];
        int     window_begin, window_end, record_begin, record_end, counter,bar;
        int     send_this_back, exit = 0, freq = 0;
        /*
                load unit array
        */
```

```
1       record_end = load_unit_array(unit, data);
        record_begin = window_begin = counter = bar = 0;
2       window_end = 10;
        sa_scrn(YELLOW, "Unit Select", YELLOW, "Scroll to desired Unit");
3       puts("\377\377updwn/");
        puts("\377\377esc/");
4       touch(handle, "group all off", entry);
        touch(handle, "group 6 on", entry);
5       touch(handle, "group 15 on", entry);
        /*
6               display valid units
        */
7       wroledsp(record_begin, window_end, record_end, bar, unit);
        do{
8               if(touch_choice('R', entry, handle)) return(0);
                switch(entry[2]){
9                       case 'D':
                                /*
10                                      scroll down
                                */
11                              freq = 680;
                                if(counter >= record_end - 1)       beep(550);
12                              else{
                                        if(counter++ >= window_end){
13                                              window_begin++;
                                                window_end++;
14                                      }
                                        bar++;
15                                      wroledsp(window_begin, window_end, record_end, bar, unit)
16              ;
                                }
                                break;
17                      case 'U':
                                /*
18                                      scroll up
                                */
19                              freq = 700;
                                if(counter <= 0) beep(550);
20                              else{
                                        if(counter-- <= window_begin){
21                                              window_begin--;
                                                window_end--;
22                                      }
                                        bar--;
23                                      wroledsp(window_begin, window_end, record_end, bar,
        unit);
24                              }
                                break;
25                      case 'H':
                                /*
26                                      history search
                                */
27                              beep(800);
                                send_this_back = 4;
28                              exit = 1;
                                break;
29                      case '!':
                                /*
30                                      enter
                                */
31                              beep(800);
                                strcpy(data->unit, (unit+bar)->location);
32                              save_unit(data);
                                send_this_back = 3;
33                              exit = 1;
                                break;
34                      case 'X':
                                /*
35                                      escape
                                */
```

```
                    beep(800);
                    send_this_back = 0;
                    exit = 1;
                    break;
            }
            if(freq){
                    sound(freq);
                    delay(200);
                    nosound();
                    freq = 0;
            }
    } while(!exit);
    return(send_this_back);
}
/*
    NAME:       wroledsp - valid unit list display
    INPUT:      bar location
                begin (b) and end (e) of window
                unit array
    RETURN:     none
*/
wroledsp(int b, int e, int recend, int bar, UNITS *unit)
{
    int count = 0, x, row = 6;
    for (x = b; x <= e; x++){
            if(x == bar) textcolor (YELLOW);
            else textcolor(LIGHTGRAY);
            if(count++ > recend - 1){
                    break;
            }
            gotoxy(5 , row++);
            cprintf(" %-7s", (unit+x)->location);
    }
}
/*
    NAME:       yesterdays_date - finds yesterdays database name
    INPUT:      none
    RETURN:     date pointer with previous date db
*/
yesterdays_date(char *date){
        char    string_time[26];
        time_t  long_time;
        int     exist;
        time(&long_time);
        long_time -= 86400L;
        strcpy(string_time, ctime(&long_time));
        strcpy(date, "h:\\db\\uv_");
        strncat(date, &string_time[4], 3);
        date[11] = '\0';
        strncat(date, &string_time[8],2);
        PXTblExist(date, &exist);
        if(!exist) return(0);
        return(1);
}
```

The code for the automated robotic station has been disclosed in the aforenoted application.

Compared to providing services in a central laboratory facility, there are considerable cost benefits of unmanned satellite laboratories. The advantages of reduced labor costs for sample transportation and laboratory staff, and reduced sample turnaround time outweigh the increased costs of equipment required for many laboratories. Our studies of the cost-saving of the University of Virginia unmanned satellite robotic laboratory showed that it saved $19,900 per year in messenger time, $22,750 per year in nursing time, and $3900 per year in supplies. If the cost for additional laboratory technologist time required for quality control and maintenance of the unit was subtracted from these savings, the net operational savings were $38,650 per year. Compared with equipment purchase costs of $85,750, the system will pay for itself over three years. Preliminary data indicate that the average test turnaround from time of physician request to reported results is 10 minutes when using the satellite robotic laboratory compared with 72 minutes when the sample is sent "stat" to the central laboratory.

One obvious alternative to an unmanned satellite laboratory is a satellite facility. The expense of such an approach is excessive requiring at least 4–5 full time equivalents for 24 hour per day/7 days per week operation. Without a very high workload, the manned satellite laboratory is not an economically sound approach to critical care testing.

The automated remote laboratory provides rapid turnaround of critical care tests, eliminates the labor costs associated with specimen processing, reduces the risks from contact with contaminated specimens, has less staff training than other on-site testing approaches, and provides improved patient care.

What is claimed is:

1. A method of interactively analyzing sample specimens and exchanging the analysis results between a plurality of user initiated remote analytical instruments having dedicated computers and a central laboratory to permit an operator at the laboratory to view and accept or reject the analysis results, said method comprising:

initiating analysis of said specimen at said dedicated computer by said user, analyzing said specimen, observing the said analysis results at said central laboratory by said operator, accepting or rejecting said analysis results by said operator, observing said acceptance or rejection at said dedicated computer by said user.

2. The method of claim 1 wherein initiating said analysis comprises the steps of:

a. checking the system hardware for the existence of monitor equipment, b. establishing database file access and reading the database for Patient sample number, c. establishing serial connection with the analytical equipment, d. initializing analyzer to standby mode e. aborting the remaining sequence if any of steps (a)–(d) fail, f. requesting user ID, g. verifying ID codes for correctness, and remaining at (g) until correct codes entered, h. displaying Mode Selection based upon the user's ID codes, engineer or medical technologist codes initiating step (ii), user codes proceeding to (i), i. displaying the analyze/review screen, an entry of Analysis proceeds to (j) and entry of review proceeds to (aa).

j. checking the analyzer to confirm that the instrument is ready for analysis and activating an alarm if not ready, k. displaying analysis screen, enabling relevant commands, l. displaying a list of valid units from the database, m. selecting the desired unit proceeds to (n), selecting the ID option proceeds to (y).

n. searching the patient roster database, for patients in the given unit, o. displaying the "Select Patient" screen and enabling relevant commands, p. displaying a list of valid patients for the selected unit, q. selecting the desired patient thereby causing the patient demographics to be displayed with relevant commands enabled, r. displaying the selected patient, ID number and location, and waiting for the user to select the desired demographics, s. prompting the user to place valid sample in the docking port, t. proceeding with sample aspiration and upon completion alerting the user to remove the sample, u. assigning and storing a sample ID number, v. analyzing the sample in the analytical instrument and querying the instrument for results and errors, w. storing the results, patient demographics, and instrument errors in a results database, x. choosing to search by patient ID displays the Search by ID screen and enables relevant commands, y. entering the Patient ID and commencing with step m, z. returning to initialization, aa. displaying the "review results" screen and enabling relevant commands, bb. displaying valid units in a database, cc. selecting the desired unit and searching the patient roster database for patients in the given unit, dd. displaying the "Select Patient" screen and enabling relevant commands, ee. displaying a list of valid patients for the selected unit and selecting the desired patient, ff. displaying the patient results screen and enabling relevant commands, gg. displaying patient results and demographics giving analysis results, pending or failed, hh. clearing system and returning to initialization, system waits for user input, ii. displaying instrument maintenance screen with relevant commands jj. waiting for and responding to Operator input.

3. The method of claim 1 wherein observing and accepting or rejecting said analysis results at said central laboratory comprises the steps of:

a. checking for existence of monitoring equipment, b. establishing access to the database, c. aborting the system if 1 or 2 above do not meet the predetermined standards, d. periodically checking the server to determine if unprocessed analysis results have been received from the analytical instrument, e. recognizing and retrieving an unprocessed test result, f. displaying the units where the sample originated and activating an alarm to alert an Operator, g. deactivating the alarm upon Operator's input and the commencement of program activation, h. displaying the test results on the monitor in the programmed format, i. requesting and verifying Operator's ID codes, j. remaining idle until an indication of acceptance or rejection is received, k. returning the accepted results to the appropriate database within the server, thereby making them available to the user upon request, l. transmitting the accepted test results to a main computer database for storage, m. returning rejected test results to the server and saving until manual or global deletion.

n. resetting the system, returning to step (d).

* * * * *

UNITED STATES PATENT AND TRADEMARK OFFICE
CERTIFICATE OF CORRECTION

PATENT NO. : 5,631,844
DATED : May 20, 1997
INVENTOR(S) : Keith S. Margrey et al.

It is certified that error appears in the above-identified patent and that said Letters Patent is hereby corrected as shown below:

Column 1,
Line 11, the following paragraph is inserted:
-- U.S. Government Rights
This invention was made with United States Government support under Grant No. HL62211, awarded by the National Institutes of Health. The United States Government has certain rights in the invention. --

Signed and Sealed this

Twenty-ninth Day of June, 2004

JON W. DUDAS
*Acting Director of the United States Patent and Trademark Office*